(12) United States Patent
Ellington et al.

(10) Patent No.: US 11,155,804 B2
(45) Date of Patent: Oct. 26, 2021

(54) RECOMBINANT POLYPEPTIDES COMPRISING SELENOCYSTEINE AND METHOD FOR PRODUCING THE SAME

(71) Applicant: BOARD OF REGENTS, THE UNIVERSITY OF TEXAS SYSTEM, Austin, TX (US)

(72) Inventors: Andrew D. Ellington, Austin, TX (US); Ross Thyer, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 109 days.

(21) Appl. No.: 16/316,768

(22) PCT Filed: Jul. 10, 2017

(86) PCT No.: PCT/US2017/041373
§ 371 (c)(1),
(2) Date: Jan. 10, 2019

(87) PCT Pub. No.: WO2018/013481
PCT Pub. Date: Jan. 18, 2018

(65) Prior Publication Data
US 2019/0316110 A1    Oct. 17, 2019

Related U.S. Application Data

(60) Provisional application No. 62/360,745, filed on Jul. 11, 2016.

(51) Int. Cl.
*C12N 9/86* (2006.01)
*C12N 15/11* (2006.01)
*C07H 21/02* (2006.01)
*A61K 38/00* (2006.01)

(52) U.S. Cl.
CPC .............. *C12N 9/86* (2013.01); *C07H 21/02* (2013.01); *C12N 15/11* (2013.01); *A61K 38/00* (2013.01)

(58) Field of Classification Search
None
See application file for complete search history.

(56) References Cited

U.S. PATENT DOCUMENTS

| | | |
|---|---|---|
| 9,464,288 B2 | 10/2016 | Soll et al. |
| 10,023,893 B2 | 7/2018 | Soll et al. |
| 10,240,158 B2 | 3/2019 | Soll et al. |
| 10,557,160 B2 | 2/2020 | Ellington et al. |
| 2008/0254512 A1 | 10/2008 | Capon |
| 2009/0087852 A1 | 4/2009 | Gladyshev et al. |
| 2009/0155255 A1 | 6/2009 | Glaser et al. |
| 2010/0298212 A1 | 11/2010 | Miao et al. |
| 2013/0303406 A1 | 11/2013 | Kim et al. |
| 2014/0154744 A1 | 6/2014 | Soll et al. |
| 2014/0303084 A1 | 10/2014 | Thorn et al. |
| 2015/0050682 A1 | 2/2015 | Hondal et al. |
| 2016/0060301 A1 | 3/2016 | Jewett et al. |
| 2016/0115232 A1 | 4/2016 | Kim et al. |
| 2016/0229920 A1 | 8/2016 | Ward et al. |
| 2017/0166945 A1 | 6/2017 | Ellington et al. |
| 2018/0105854 A1 | 4/2018 | Söli et al. |
| 2019/0194713 A1 | 6/2019 | Mandell et al. |

FOREIGN PATENT DOCUMENTS

| | | |
|---|---|---|
| JP | H10309193 A | 11/1998 |
| JP | 2010509222 A | 10/2008 |
| WO | WO 2016/172269 | 10/1916 |
| WO | WO 2018/014091 | 1/1918 |
| WO | WO 01/12657 | 2/2001 |
| WO | WO 01/12657 A2 * | 2/2001 |
| WO | WO 2003/029469 | 4/2003 |
| WO | WO 2007/075438 | 7/2007 |
| WO | WO 2009/067636 | 5/2009 |
| WO | WO 2013/009868 | 1/2013 |

OTHER PUBLICATIONS

Aldag, Caroline, et al. "Rewiring Translation for Elongation Factor Tu-Dependent Selenocysteine Incorporation." *Angewandte Chemie International Edition* 52.5 (2013): 1441-1445.
Anderson, J. C. et al. An expanded genetic code with a functional quadruplet codon. Proc. Natl. Acad. Sci. U. S. A. 101, 7566-7571 (2004).
Arai, Kenta, et al. "Preparation of selenoinsulin as a long-lasting insulin analogue." *Angewandte Chemie* 129.20 (2017): 5614-5618.
Armishaw et al., Alpha-selenoconotoxins, a new class of potent alpha7 neuronal nicotinic receptor antagonists. *J Biol Chem* 281, 14136-43 (2006).
Chatterjee, A., Lajoie, M. J., Xiao, H., Church, G. M. & Schultz, P. G. A Bacterial Strain with a Unique Quadruplet Codon Specifying Non-native Amino Acids. Chembiochem, n/a-n/a (2014).
Chatterjee, A., Sun, S. B., Furman, J. L., Xiao, H. & Schultz, P. G. A Versatile Platform for Single- and Multiple-Unnatural Amino Acid Mutagenesis in *Escherichia coli*. Biochemistry 52, 1828-1837, doi:10.1021/bi4000244 (2013).
Database ENA, Accession No. ENG64632, "*Escherichia coli* p0305293.4 cysteine synthase A", dated Apr. 10, 2013.
Database ENA, Accession No. KJJ77964, "*Escherichia coil* glutamyl tRNA reductase", dated May 12, 2016.
Database UniProt, Accession No. B1ITB1, "RecName: Full= Peptide chain release factor 2", dated May 20, 2008.
Database UniProt, Accession No. F4VHX6, "RecName: Full=7-carboxy-7-deazaguanine synthase", dated Jun. 28. 2011.
Database UniProt, Accession No. G5QQB8, "RecName: Full =Aerobic respiration control sensor protein", dated Jan. 25, 2012.

(Continued)

*Primary Examiner* — Kagnew H Gebreyesus
(74) *Attorney, Agent, or Firm* — Parker Highlander PLLC

(57) ABSTRACT

Composition comprising purified recombinant selenoproteins, such an antibodies and enzymes, are provided. Method of producing such recombinant polypeptides and bacterial strains for the same are likewise provided.

10 Claims, 9 Drawing Sheets

Specification includes a Sequence Listing.

(56) References Cited

OTHER PUBLICATIONS

Extended European Search Report and Written Opinion issued in European Application No. 17847457.3, dated Jun. 12, 2020.
Extended European Search Report and Written Opinion issued in European Application No. 17828247.1, dated Jun. 29, 2020.
Ganther et al., Selenium metabolism, selenoproteins and mechanisms of cancer prevention: complexities with thioredoxin reductase. *Carcinogenesis* 20, 1657-1666 (1999).
International Search Report and Written Opinion issued in International Application No. PCT/US2017/041373, dated Nov. 17, 2017.
International Search Report and Written Opinion issued in International Application No. PCT/US17/49354, dated Jan. 25, 2018.
Invitation to Pay Additional Fees issued in International Application No. PCT/US17/49354, dated Nov. 17, 2017.
Lajoie, M. J. et al. Probing the limits of genetic recoding in essential genes. *Science* 342, 361-363, doi:10.1126/science.1241460 (2013).
Lajoie, Marc J., et al. "Genomically recoded organisms expand biological functions." *Science* 342.6156 (2013): 357-360.
Li, Xiuling, et al. "Site-specific dual antibody conjugation via engineered cysteine and selenocysteine residues." *Bioconjugate Chemistry* 26.11 (2015): 2243-2248.
Liu, C. C. & Schultz, P. G. Adding new chemistries to the genetic code. *An. Rev. Biochem.* 79, 413-444 (2010).
Liu, Hongcheng, and Kimberly May. "Disulfide bond structures of IgG molecules: structural variations, chemical modifications and possible impacts to stability and biological function." *MAbs*. vol. 4. No. 1. Taylor & Francis, 2012.
Mandell, Daniel J., et al. "Biocontainment of genetically modified organisms by synthetic protein design." *Nature* 518.7537 (2015): 55-60.
McDaniel, Timothy K., et al. "A genetic locus of enterocyte effacement conserved among diverse enterobacterial pathogens," *Proceedings of the National Academy of Sciences* 92.5 (1995): 1664-1668.
Miller, Corwin, et al. "A synthetic tRNA for EF-Tu mediated selenocysteine incorporation in vivo and in vitro," *FEBS letters* 589. 17 (2015): 2194-2199.
Moroder, Luis, et al. "Synthesis of single-and multiple-stranded cystine-rich peptides." *Peptide Science: Original Research on Biomolecules* 80.2-3 (2005): 85-97.
Mueller, Sabine, et al. "The formation of diselenide bridges in proteins by incorporation of selenocysteine residues: biosynthesis and characterization of (Se) 2-thioredoxin." *Biochemistry* 33.11 (1994): 3404-3412.
Muttenthaler et al., Modulating oxytocin activity and plasma stability by disulfide bond engineering. *J Med Chem* 53, 8585-96 (2010).
Neumann, H., Wang, K., Davis, L., Garcia-Alai, M. & Chin, J. W. Encoding multiple unnatural amino acids via evolution of a quadruplet-decoding ribosome. Nature 464, 441-444, (2010).
Neumann, H., Wang, K., Davis, L., Garcia-Alai, M. & Chin, J. W. Encoding multiple unnatural amino acids via evolution of a quadruplet-decoding ribosome. Nature 464, 441-444, (2010). Supplemental Information.
Ostrov, Nili, et al. "Design, synthesis, and testing toward a 57-codon genome." *Science* 353.6301 (2016): 819-822.
Partial European Search Report and Written Opinion issued in European Application No. 17847457.3, dated Mar. 12, 2020.
Partial European Search Report and Written Opinion issued in European Application No. 17828247.1, dated Jan. 31. 2020.
Rengby, Olle, and Elias SJ Arnér. "Titration and conditional knockdown of the prfB gene in *Escherichia coli*: effects on growth and overproduction of the recombinant mammalian selenoprotein thioredoxin reductase." *Applied and Environmental Microbiology* 73.2 (2007): 432-441.
Safavi-Hemami, Helena, et al. "Specialized insulin is used for chemical warfare by fish-hunting cone snails." *Proceedings of the National Academy of Sciences* 112.6 (2015): 1743-1748.
Score result for US 2014-0154744, SEQ ID No. 18, dated 2014. Downloaded from internet on Oct. 31, 2018, in U.S. Appl. No. 15/380,560.
Score result for WO 2013/009868, dated 2013. Downloaded from internet on Jun. 3, 2019, in U.S. Appl. No. 15/380,560.
Thyer, Ross, et al. "Evolving tRNA.Sec for efficient canonical incorporation of selenocysteine." *Journal of the American Chemical Society* 137.1 (2015): 46-49.
Wang, Fei, Jana M. Carabino, and Cunegundo M. 'Vergara. "insulin glargine: a systematic review of a long-acting insulin analogue." *Clinical Therapeutics* 25.6 (2003): 1541-1577.
Wang, L., Brock, A., Herberich, B. & Schultz, P. G. Expanding the genetic code of *Escherichia coli*. Science 292, 498-500 (2001).
Weil-Ktorza, Orit, et al. "Substitution of an internal disulfide bridge with a Diselenide enhances both Foldability and stability of human insulin." *Chemistry—A European Journal* 25.36 (2019): 8430-8430.
Young, T. S., Ahmad, I., Yin, J. A. & Schultz, P. G. An enhanced system for unnatural amino acid mutagenesis in *E. coli*. Journal of Molecular Biology 395, 361-374 (2009).
Database GenBank, Accession No. AQAP01000376, "*Escherichia coli* P0304777.5 gecP03047775.contig.386, whole genome shotgun sequence", dated Apr. 8, 2013.
Office Communication issued in corresponding Japanese Application No. 2019-500781, dated May 12, 2021. Original with Machine Translation.

* cited by examiner

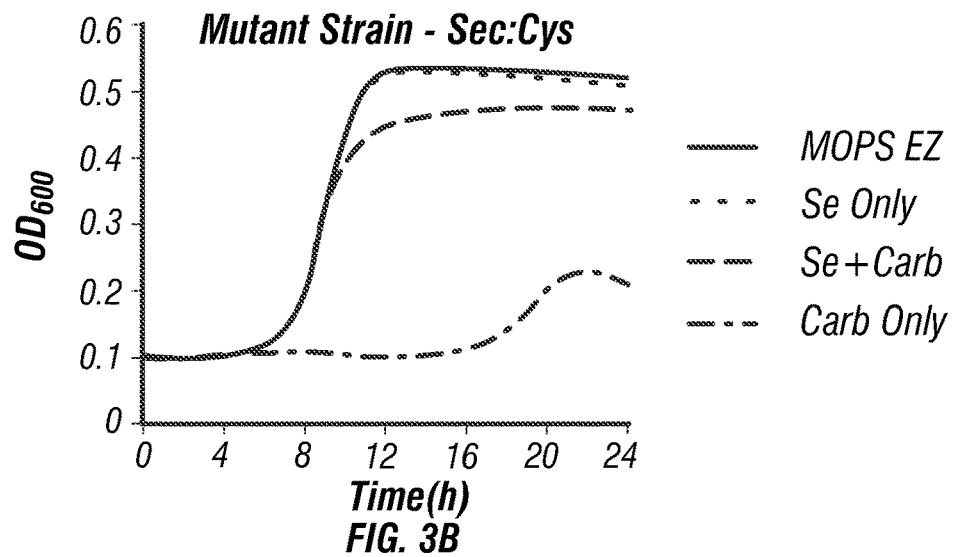
FIG. 3B
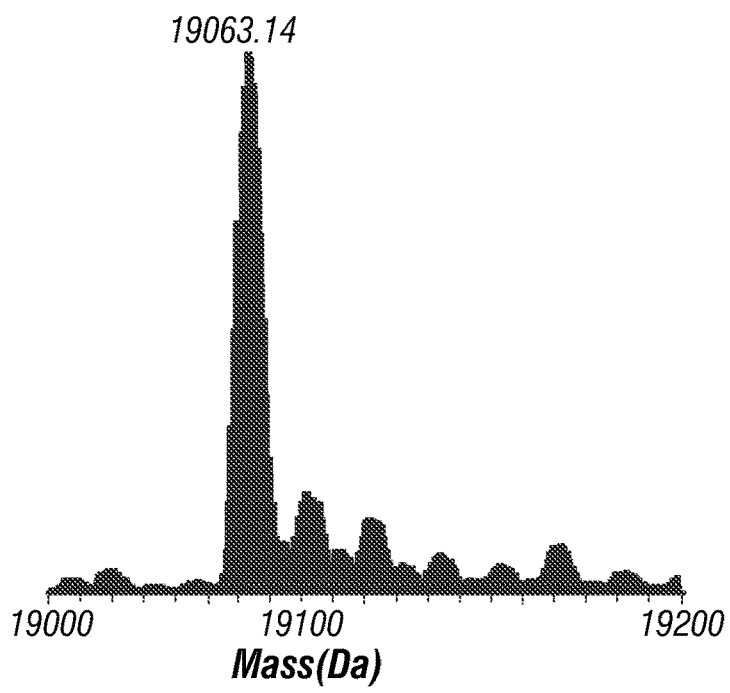
FIG. 4A
```
N   M U S L I  A A L A V D R V I G M E N A M P W N L P   25
26  A D L A W F K R N T L N K U V I M G R H T W E S I   50
51  G R P L P G R K N I I L S S Q P G T D D R V T W V   75
76  K S V D E A I A A U G D V P E I M V I G G R V Y   100
101 E Q F L P K A Q K L Y L T H I D A E V E G D T H F   125
126 P D Y E P D D W E S V F S E F H D A D A Q N S H S   150
151 Y C F E I L E R R G S H H H H H H C
```
FIG. 4B

| | Theoretical Monoisotopic Mass(Da) | Experimental Monoisotopic Mass(Da) | Mass Accuracy (ppm) |
|---|---|---|---|
| anti-MS2 scFv (Ser) | 31603.40 | | |
| anti-MS2 scFv (2xU, No Crosslink) | 31855.10 | 31851.08 | -125.57 |
| anti-MS2 scFv (2xU, Crosslink) | 31851.06 | 31851.08 | +0.6 |

NM EVQLLESGGGLAKPGGSLRLSCAA 25
26 SGFTFTDYYMDWVRQAPGKGLEWVS 50
51 RISPGGDVTWYADSVKGRFTISRDN 75
76 AQNTLYLMNSLRAEDTAVYYCARD 100
101 DIVVSRIFDDWGQGVLLTVSSGGGG 125
126 SGGGSGGGGSELQMTQSPSSLSAS 150
151 VGDRVTITCRASQSIRSYLAWYQQK 175
176 PGKAPKLLIYDAAHLQSGVPSRFSG 200
201 SGSGTEFSLTISSLQPEDFAVYYCQ 225
226 QRNSYPLLTFGGGTKVEIKRGSHHHH 250
251 HHC

RECOMBINANT POLYPEPTIDES COMPRISING SELENOCYSTEINE AND METHOD FOR PRODUCING THE SAME

This application is a national phase application under 35 U.S.C. § 371 of International Application No. PCT/US2017/041373, filed Jul. 10, 2017, which claims the benefit of U.S. Provisional Patent Application No. 62/360,745, filed Jul. 11, 2016, the entirety of each of which is incorporated herein by reference.

This invention was made with government support under Grant No. CHE1402753 awarded by the National Science Foundation and Grant no. K99 CA207870 awarded by the National Institutes of Health. The government has certain rights in the invention.

BACKGROUND OF THE INVENTION

1. Field of the Invention

The present invention relates generally to the field of molecular biology. More particularly, it concerns polypeptides comprising non-canonical amino acids.

2. Description of Related Art

Selenium is used by certain organisms for the expression of selenoproteins.

Selenoproteins are a unique group of polypeptides that are found in both prokaryotes and eukaryotes and contain the non-canonical amino acid, selenocysteine. Selenocysteine has a significantly lower $pK_a$ than cysteine (5.2 vs 8.5 for free amino acid) and much stronger nucleophilic properties, making it an attractive target for altering protein chemistry and function. Unfortunately, most selenoproteins have proven difficult to produce in *E. coli*, the standard host for recombinant protein production. This is due to the inherently low efficiency of selenocysteine incorporation in bacteria (4-5% vs termination of protein synthesis). In addition, the requirement that the SECIS element immediately follows the UGA codon, forming part of the coding sequence, greatly limits which proteins are amenable to selenocysteine insertion.

Recently, an evolved *E. coli* tRNA$^{Sec}$ that is compatible with the canonical translation machinery and can suppress amber stop codons to incorporate selenocysteine with high efficiency was also developed. However, there is an unmet need for systems allow for efficient incorporate selenocysteine to produce commercially relevant amounts of recombinant selenoproteins.

SUMMARY OF THE INVENTION

A first embodiment of the present disclosure provides a composition comprising purified recombinant polypeptides, said polypeptides comprising at least one selenocysteine residue at a selected position not found in a wild type version of the polypeptide, wherein at least 80% of the recombinant polypeptides in the composition comprise the selenocysteine residue at the selected position. In certain aspects, the recombinant polypeptides comprise an antibody or an enzyme. In certain aspects, the composition comprises at least 10 µg, 50 µg, 100 µg, 500 µg or 1 mg of the purified recombinant polypeptides. In some aspects, the purified recombinant polypeptides are 95%-99.9% pure, e.g., at least about 95%, 96%, 97%, 98%, 99% or 99.5% pure.

In some aspects, 80%-99.9% of the recombinant polypeptides in the composition comprise the selenocysteine residue at the selected position. In certain aspects, 90%-99% of the recombinant polypeptides in the composition comprise the selenocysteine residue at the selected position. In some aspects, at least 90%, 91%, 92%, 93%, 94%, 95%, 96%, 97%, 98% or 99% of the recombinant polypeptides in the composition comprise the selenocysteine residue at the selected position. In still further aspects, a composition comprises recombinant polypeptides having at least two selenocysteine residues at selected positions and 80%-99.9% (e.g., at least 90%, 91%, 92%, 93%, 94%, 95%, 96%, 97%, 98% or 99%) of the recombinant polypeptides in the composition comprise both of the selenocysteine residues at the selected positions. In yet further aspects, a composition comprises recombinant polypeptides having at least two selenocysteine residues at selected positions that form a diselenide bond and 80%-99.9% (e.g., at least 90%, 91%, 92%, 93%, 94%, 95%, 96%, 97%, 98% or 99%) of the recombinant polypeptides in the composition comprise the diselenide bond between the selenocysteine residues at the selected positions.

In some aspects, the recombinant polypeptides are at least 85%, 90%, 91%, 92%, 93%, 94%, 95%, 96%, 97%, 98% or 99% identical to a human polypeptide. In certain aspects, the human polypeptide is a polypeptide involved in a disease. In some aspects, the human polypeptide is an enzyme, a chemokine, a cytokine, an antibody or T-cell receptor. In some aspects, the antibody is an aglycosylated antibody. In still further aspects, the human polypeptide is a polypeptide that comprises a disulfide bond and the recombinant polypeptide comprises a diselenide bond in place of the disulfide bond.

In certain aspects, the polypeptide comprises 2, 3, 4, 5, 6, 7, 8, 9 or 10 selenocysteine residues at selected positions. In further aspects, at least about 80%-99.9% (e.g., at least 90%, 91%, 92%, 93%, 94%, 95%, 96%, 97%, 98% or 99%) of the recombinant polypeptides in the composition comprise selenocysteine residues at each of the selected positions. In still further aspects, the polypeptides comprise at least two selenocysteine residues at selected positions. In certain aspects, the two selenocysteine residues at the selected positions form a diselenide bond.

A further embodiment provides a pharmaceutical composition comprising a composition of the embodiments comprising purified recombinant polypeptides, said polypeptides comprising at least one selenocysteine residue at a selected position not found in a wild type version of the polypeptide, wherein at least 80%-99.9% (e.g., at least 90%, 91%, 92%, 93%, 94%, 95%, 96%, 97%, 98% or 99%) of the recombinant polypeptides in the composition comprise the selenocysteine residue at the selected position.

Further embodiments provide a method of treating a subject comprising administering an effective amount of a pharmaceutical composition of the embodiments comprising purified recombinant polypeptides, said polypeptides comprising at least one selenocysteine residue at a selected position not found in a wild type version of the polypeptide, wherein at least 80%-99.9% (e.g., at least 90%, 91%, 92%, 93%, 94%, 95%, 96%, 97%, 98% or 99%) of the recombinant polypeptides in the composition comprise the selenocysteine residue at the selected position.

In yet a further embodiment, there is provided a nucleic acid molecule encoding a polypeptide comprising an amino acid sequence at least 85%, 90%, 91%, 92%, 93%, 94%, 95%, 96%, 97%, 98% or 99% identical to: (a) SEQ ID NO:1 and having an amino acid substitution or deletion at a position corresponding to position 344 of SEQ ID NO:1; (b) SEQ ID NO:2 and having an amino acid substitution or deletion at a position corresponding to position 702 of SEQ ID NO:2; (c) SEQ ID NO:3 and having an amino acid substitution or deletion at a position corresponding to position 655 of SEQ ID NO:3; (d) SEQ ID NO:4 and having an amino acid substitution or deletion at a position corresponding to position 73 of SEQ ID NO:4; (e) SEQ ID NO:5 and having an amino acid substitution or deletion at a position corresponding to position 781 of SEQ ID NO:5; (0 SEQ ID NO:6 and having an amino acid substitution or deletion at a position corresponding to position 136 of SEQ ID NO:6; (g) SEQ ID NO:7 and having an amino acid substitution or deletion at a position corresponding to position 183 of SEQ ID NO:7; (h) SEQ ID NO:8 and having an amino acid substitution or deletion at a position corresponding to position 1 of SEQ ID NO:8; (i) SEQ ID NO:9 and having an amino acid substitution or deletion at a position corresponding to position 102 of SEQ ID NO:9; (j) SEQ ID NO:10 and having an amino acid substitution or deletion at a position corresponding to position 105 of SEQ ID NO:10; (k) SEQ ID NO:11 and having an amino acid substitution or deletion at a position corresponding to position 673 of SEQ ID NO:11; (1) SEQ ID NO:12 and having an amino acid substitution or deletion at a position corresponding to position 69 of SEQ ID NO:12; (m) SEQ ID NO:13 and having an amino acid substitution or deletion at a position corresponding to position 107 of SEQ ID NO:13; (n) SEQ ID NO:17 and having an amino acid substitution or deletion at a position corresponding to position 246 of SEQ ID NO:17; (o) SEQ ID NO:18 and having an amino acid substitution or deletion at a position corresponding to position 545 of SEQ ID NO:18; and/or (p) SEQ ID NO:19 and having an amino acid substitution or deletion at a position corresponding to position 124 of SEQ ID NO:19.

A further embodiment provides a recombinant polypeptide comprising an amino acid sequence at least 85%, 90%, 91%, 92%, 93%, 94%, 95%, 96%, 97%, 98% or 99% identical to: (a) SEQ ID NO:1 and having an amino acid substitution or deletion at a position corresponding to position 344 of SEQ ID NO:1; (b) SEQ ID NO:2 and having an amino acid substitution or deletion at a position corresponding to position 702 of SEQ ID NO:2; (c) SEQ ID NO:3 and having an amino acid substitution or deletion at a position corresponding to position 655 of SEQ ID NO:3; (d) SEQ ID NO:4 and having an amino acid substitution or deletion at a position corresponding to position 73 of SEQ ID NO:4; (e) SEQ ID NO:5 and having an amino acid substitution or deletion at a position corresponding to position 781 of SEQ ID NO:5; (0 SEQ ID NO:6 and having an amino acid substitution or deletion at a position corresponding to position 136 of SEQ ID NO:6; (g) SEQ ID NO:7 and having an amino acid substitution or deletion at a position corresponding to position 183 of SEQ ID NO:7; (h) SEQ ID NO:8 and having an amino acid substitution or deletion at a position corresponding to position 1 of SEQ ID NO:8; (i) SEQ ID NO:9 and having an amino acid substitution or deletion at a position corresponding to position 102 of SEQ ID NO:9; (j) SEQ ID NO:10 and having an amino acid substitution or deletion at a position corresponding to position 105 of SEQ ID NO:10; (k) SEQ ID NO:11 and having an amino acid substitution or deletion at a position corresponding to position 673 of SEQ ID NO:11; (1) SEQ ID NO:12 and having an amino acid substitution or deletion at a position corresponding to position 69 of SEQ ID NO:12; (m) SEQ ID NO:13 and having an amino acid substitution or deletion at a position corresponding to position 107 of SEQ ID NO:13; (n) SEQ ID NO:17 and having an amino acid substitution or deletion at a position corresponding to position 246 of SEQ ID NO:17; (o) SEQ ID NO:18 and having an amino acid substitution or deletion at a position corresponding to position 545 of SEQ ID NO:18; or (p) SEQ ID NO:19 and having an amino acid substitution or deletion at a position corresponding to position 124 of SEQ ID NO:19. In still further aspects, there is provided a nucleic acid molecule encoding one of the foregoing polypeptides.

In some aspects, the polypeptide in accordance with the foregoing paragraph comprises a Pro substitution at a position corresponding to position 344 of SEQ ID NO:1. In certain aspects, the polypeptide comprises a His substitution at a position corresponding to position 702 of SEQ ID NO:2. In some aspects, the polypeptide comprises an Ala substitution at a position corresponding to position 655 of SEQ ID NO:3. In some aspects, the polypeptide comprises an Ala substitution at a position corresponding to position 73 of SEQ ID NO:4. In certain aspects, the polypeptide comprises a Gly substitution at a position corresponding to position 781 of SEQ ID NO:5. In some aspects, the polypeptide comprises a Val substitution at a position corresponding to position 136 of SEQ ID NO:6. In some aspects, the polypeptide comprises an Ala substitution at a position corresponding to position 183 of SEQ ID NO:7. In certain aspects, the polypeptide comprises an Arg substitution at a position corresponding to position 1 of SEQ ID NO:8. In some aspects, the polypeptide comprises a Cys substitution at a position corresponding to position 102 of SEQ ID NO:9. In some aspects, the polypeptide comprises a Cys substitution at a position corresponding to position 105 of SEQ ID NO:10. In certain aspects, the polypeptide comprises a Leu substitution at a position corresponding to position 673 of SEQ ID NO:11. In some aspects, the polypeptide comprises a Gly substitution at a position corresponding to position 69 of SEQ ID NO:12. In certain aspects, the polypeptide comprises a Ser substitution at a position corresponding to position 107 of SEQ ID NO:13. In some aspects, the polypeptide comprises an Ala substitution at a position corresponding to position 246 of SEQ ID NO:17. In certain aspects, the polypeptide comprises an Ile substitution at a position corresponding to position 545 of SEQ ID NO:18. In some aspects, the polypeptide comprises a Pro substitution at a position corresponding to position 124 of SEQ ID NO:19. In still further aspects, there is provided a nucleic acid molecule encoding one of the foregoing polypeptides.

In some aspects, the polypeptide further comprises an amino acid sequence at least 85%, 90%, 91%, 92%, 93%, 94%, 95%, 96%, 97%, 98% or 99% identical to SEQ ID NO:1 and a Thr substitution at a position corresponding to position 999, a Thr substitution at a position corresponding to position 457, a Pro substitution at a position corresponding to position 591, a Thr substitution at a position corresponding to position 183, a Leu substitution at a position corresponding to position 358, a Arg substitution at a position corresponding to position 23, a Ile substitution at a position corresponding to position 902, a Val substitution at a position corresponding to position 889, a Cys substitution at a position corresponding to position 620, and/or a Gly substitution at a position corresponding to position 174 of SEQ ID NO:1. In still further aspects, there is provided a nucleic acid molecule encoding one of the foregoing polypeptides.

In certain aspects, the polypeptide further comprises an amino acid sequence at least 85%, 90%, 91%, 92%, 93%, 94%, 95%, 96%, 97%, 98% or 99% identical to SEQ ID NO:3 and a Cys substitution at a position corresponding to position 398, an Ala substitution at a position corresponding to position 652, a Cys substitution at a position corresponding to position 264, and/or an Ala substitution at a position corresponding to position 21 of SEQ ID NO:3. In still further aspects, there is provided a nucleic acid molecule encoding one of the foregoing polypeptides.

In some aspects, the polypeptide further comprises an amino acid sequence at least 85%, 90%, 91%, 92%, 93%, 94%, 95%, 96%, 97%, 98% or 99% identical to SEQ ID NO:4 and an Asn substitution at a position corresponding to position 45, a Leu substitution at a position corresponding to position 290, a Asp substitution at a position corresponding to position 271, a Tyr substitution at a position corresponding to position 153, a Val substitution at a position corresponding to position 45, a Pro substitution at a position corresponding to position 284, an Ile substitution at a position corresponding to position 73, a Leu substitution at a position corresponding to position 68, an Ile substitution at a position corresponding to position 69, a Cys substitution at a position corresponding to position 305, a Ser substitution at a position corresponding to position 144, and/or a Val substitution at a position corresponding to position 281 of SEQ ID NO:4. In still further aspects, there is provided a nucleic acid molecule encoding one of the foregoing polypeptides.

In certain aspects, the polypeptide further comprises an amino acid sequence at least 85%, 90%, 91%, 92%, 93%, 94%, 95%, 96%, 97%, 98% or 99% identical to SEQ ID NO:5 and a Gly substitution at a position corresponding to position 916, a His substitution at a position corresponding to position 938, a His substitution at a position corresponding to position 860, a Asp substitution at a position corresponding to position 925, and/or a Met substitution at a position corresponding to position 470 of SEQ ID NO:5. In still further aspects, there is provided a nucleic acid molecule encoding one of the foregoing polypeptides.

In some aspects, the polypeptide further comprises an amino acid sequence at least 85%, 90%, 91%, 92%, 93%, 94%, 95%, 96%, 97%, 98% or 99% identical to SEQ ID NO:6 and an Ala substitution at a position corresponding to position 115, an Arg substitution at a position corresponding to position 386, an Arg substitution at a position corresponding to position 155, a Ser substitution at a position corresponding to position 98, an Ala substitution at a position corresponding to position 201, a Thr substitution at a position corresponding to position 294, a Tyr substitution at a position corresponding to position 159, and/or an Ile substitution at a position corresponding to position 112 of SEQ ID NO:6. In still further aspects, there is provided a nucleic acid molecule encoding one of the foregoing polypeptides.

In some aspects, the polypeptide further comprises an amino acid sequence at least 85%, 90%, 91%, 92%, 93%, 94%, 95%, 96%, 97%, 98% or 99% identical to SEQ ID NO:18 and a Gly substitution at a position corresponding to position 76, a Val substitution at a position corresponding to position 293, a Thr substitution at a position corresponding to position 637, a Val substitution at a position corresponding to position 3, a Ser substitution at a position corresponding to position 311, a Thr substitution at a position corresponding to position 471, a Val substitution at a position corresponding to position 228, a Ser substitution at a position corresponding to position 311, and/or a Thr substitution at a position corresponding to position 257 of SEQ ID NO:18. In still further aspects, there is provided a nucleic acid molecule encoding one of the foregoing polypeptides.

In certain aspects, the polypeptide further comprises an amino acid sequence at least 85%, 90%, 91%, 92%, 93%, 94%, 95%, 96%, 97%, 98% or 99% identical to SEQ ID NO:7 and a Val substitution at a position corresponding to position 173, a Leu substitution at a position corresponding to position 196, a Phe substitution at a position corresponding to position 180, an Ala substitution at a position corresponding to position 249, a Val substitution at a position corresponding to position 5, a Leu substitution at a position corresponding to position 273, and/or an Asn substitution at a position corresponding to position 176 of SEQ ID NO:7. In still further aspects, there is provided a nucleic acid molecule encoding one of the foregoing polypeptides.

In some aspects, the polypeptide further comprises n amino acid sequence at least 85%, 90%, 91%, 92%, 93%, 94%, 95%, 96%, 97%, 98% or 99% identical to SEQ ID NO:9 and a Cys substitution at a position corresponding to position 15 and/or a substitution at a position corresponding to position 30 of SEQ ID NO:9. In still further aspects, there is provided a nucleic acid molecule encoding one of the foregoing polypeptides.

In certain aspects, the polypeptide further comprises n amino acid sequence at least 90% identical to SEQ ID NO:19 and a Ile substitution at a position corresponding to position 193, a Thr substitution at a position corresponding to position 233, an Ala substitution at a position corresponding to position 300, and/or an Arg substitution at a position corresponding to position 199 of SEQ ID NO:19.

In some aspects, the polypeptide further comprises an amino acid sequence at least 85%, 90%, 91%, 92%, 93%, 94%, 95%, 96%, 97%, 98% or 99% identical to SEQ ID NO:17 and an Ala substitution at a position corresponding to position 246 of SEQ ID NO:17. In still further aspects, there is provided a nucleic acid molecule encoding one of the foregoing polypeptides.

In some aspects, the polypeptide further comprises an amino acid sequence at least 85%, 90%, 91%, 92%, 93%, 94%, 95%, 96%, 97%, 98% or 99% identical to SEQ ID NO:11 and a Val substitution at a position corresponding to position 119, a Pro substitution at a position corresponding to position 535, an Arg substitution at a position corresponding to position 373, a Ser substitution at a position corresponding to position 535, a Thr substitution at a position corresponding to position 119, an Ala substitution at a position corresponding to position 601, a Lys substitution at a position corresponding to position 103, an Asp substitution at a position corresponding to position 31, an Ile substitution at a position corresponding to position 662, a Lys substitution at a position corresponding to position 359, and/or an Asp substitution at a position corresponding to position 519 of SEQ ID NO:11. In still further aspects, there is provided a nucleic acid molecule encoding one of the foregoing polypeptides.

Another embodiment provides a nucleic acid molecule encoding a polypeptide comprising: (i) an amino acid sequence at least 85%, 90%, 91%, 92%, 93%, 94%, 95%, 96%, 97%, 98% or 99% identical to SEQ ID NO:14, and (ii) an Ile substitution at a position corresponding to position 212, an Asn substitution at a position corresponding to position 162, an Ala substitution at a position corresponding to position 299, and/or a Arg substitution at a position corresponding to position 220. In still further aspects, there is provided a nucleic acid molecule encoding one of the foregoing polypeptides.

In yet another embodiment, there is provided a recombinant polypeptide comprising: (i) an amino acid sequence at least 85%, 90%, 91%, 92%, 93%, 94%, 95%, 96%, 97%, 98% or 99% identical to SEQ ID NO:14, and (ii) an Ile substitution at a position corresponding to position 212, an Asn substitution at a position corresponding to position 162, an Ala substitution at a position corresponding to position 299, and/or a Arg substitution at a position corresponding to position 220. In still further aspects, there is provided a nucleic acid molecule encoding one of the foregoing polypeptides.

In a further embodiment, there is provided a nucleic acid molecule encoding a polypeptide comprising: (i) an amino acid sequence at least 85%, 90%, 91%, 92%, 93%, 94%, 95%, 96%, 97%, 98% or 99% identical to SEQ ID NO:15, and (ii) an Ala substitution at a position corresponding to position 184, an Asn substitution at a position corresponding to position 1730, an Asp substitution at a position corresponding to position 1888, a Thr substitution at a position corresponding to position 352, a Ser substitution at a position corresponding to position 374, an Arg substitution at a position corresponding to position 1423, a Glu substitution at a position corresponding to position 1502, a Gln substitution at a position corresponding to position 285, a Lys substitution at a position corresponding to position 470, a Thr substitution at a position corresponding to position 939, a Phe substitution at a position corresponding to position 1669, an Ile substitution at a position corresponding to position 2034, an Asn substitution at a position corresponding to position 1713, a Thr substitution at a position corresponding to position 704, and/or an Ile substitution at a position corresponding to position 1084.

In yet a further embodiment, there is provided a recombinant polypeptide comprising: (i) an amino acid sequence at least 85%, 90%, 91%, 92%, 93%, 94%, 95%, 96%, 97%, 98% or 99% identical to SEQ ID NO:15, and (ii) an Ala substitution at a position corresponding to position 184, an Asn substitution at a position corresponding to position 1730, an Asp substitution at a position corresponding to position 1888, a Thr substitution at a position corresponding to position 352, a Ser substitution at a position corresponding to position 374, an Arg substitution at a position corresponding to position 1423, a Glu substitution at a position corresponding to position 1502, a Gln substitution at a position corresponding to position 285, a Lys substitution at a position corresponding to position 470, a Thr substitution at a position corresponding to position 939, a Phe substitution at a position corresponding to position 1669, an Ile substitution at a position corresponding to position 2034, an Asn substitution at a position corresponding to position 1713, a Thr substitution at a position corresponding to position 704, and/or an Ile substitution at a position corresponding to position 1084.

In an embodiment, there is provided a nucleic acid molecule encoding a polypeptide comprising: (i) an amino acid sequence at least 85%, 90%, 91%, 92%, 93%, 94%, 95%, 96%, 97%, 98% or 99% identical to SEQ ID NO:16, and (ii) a Phe substitution at a position corresponding to position 112, an Ala substitution at a position corresponding to position 126, an Leu substitution at a position corresponding to position 978, a Gly substitution at a position corresponding to position 199, a Thr substitution at a position corresponding to position 476, and/or a Val substitution at a position corresponding to position 735.

A further embodiment provides a recombinant polypeptide comprising: (i) an amino acid sequence at least 85%, 90%, 91%, 92%, 93%, 94%, 95%, 96%, 97%, 98% or 99% identical to SEQ ID NO:16, and (ii) a Phe substitution at a position corresponding to position 112, an Ala substitution at a position corresponding to position 126, an Leu substitution at a position corresponding to position 978, a Gly substitution at a position corresponding to position 199, a Thr substitution at a position corresponding to position 476, and/or a Val substitution at a position corresponding to position 735.

An embodiment also provides a bacterial strain comprising at least one nucleic acid molecule of the embodiments or expressing at least one polypeptides of the embodiments (e.g., a polypeptide at least 85%, 90%, 91%, 92%, 93%, 94%, 95%, 96%, 97%, 98% or 99% identical to one of the polypeptides of SEQ ID NO: 1 and comprising one of the substitutions listed in Table 1). In some aspects, the bacterial strain comprises at least 2, 3, 4, 5, 6, 7, 8, 9, 10, 11, 12, 13, 14, 15, 16, 17, 18 or 19 nucleic acid molecules encoding the polypeptides of Table 1. In some aspects, the bacterial strain expresses the polypeptide encoded by at least 2, 3, 4, 5, 6, 7, 8, 9, 10, 11, 12, 13, 14, 15, 16, 17, 18 or 19 nucleic acid molecules.

In further aspects, the bacterial strain comprises a nucleic acid encoding a tRNA and an aminoacyl-tRNA synthetase for incorporation of selenocysteine. In some aspects, the tRNA recognizes a UAG codon. In some aspects, the bacterial strain comprises a nucleic acid that encodes a tRNA is at least 90% identical to SEQ ID NO: 20, SEQ ID NO: 21, or SEQ ID NO: 22. In some aspects, the bacterial strain further comprises one or more of the following features: (i) a G or C at a position corresponding to position 7; (ii) a T at a position corresponding to position 49; (iii) a A or C at a position corresponding to position 50; (iv) a T at a position corresponding to position 64; (v) a G or A at a position corresponding to position 65; and/or (vi) a G, T or C at a position corresponding to position 66. In some aspects, the molecule encodes a tRNA comprising the sequence at least about 90% identical to SEQ ID NO: 20; and comprises one or more of the following features: (i) a G at a position corresponding to position 7; (ii) a T at a position corresponding to position 49; (iii) a C at a position corresponding to position 50; (iv) a T at a position corresponding to position 64; (v) a G at a position corresponding to position 65; and/or (vi) a C at a position corresponding to position 66. In further aspects, the molecule encodes a tRNA comprising a sequence that is at least 85%, 90%, 91%, 92%, 93%, 94%, 95%, 96%, 97%, 98% or 99% identical to SEQ ID NO: 18, SEQ ID NO: 19, SEQ ID NO: 20 or SEQ ID NO: 4. In specific aspects, the molecule encodes a tRNA comprising SEQ ID NO: 18, SEQ ID NO: 19, SEQ ID NO: 20 or SEQ ID NO: 4.

In some aspects, the bacterial strain further comprises an expressible nucleic sequence encoding a polypeptide of interest having at least one position in the coding sequence with a TAG codon for selenocysteine incorporation. In certain aspects, the expressible nucleic sequence encodes a human polypeptide. In some aspects, the expressible nucleic sequence encodes an enzyme or an antibody. In certain aspects, the expressible nucleic sequence comprises a T7 RNA polymerase promoter. In some aspects, the bacterial strain further comprises a nucleic acid sequence encoding T7 RNA polymerase.

In further aspects, the bacterial strain is a gram negative bacteria, such as an *E. coli* strain. In a further embodiment provides an *E. coli* bacterial strain deposited at NCIMB under the accession no. 42595. In yet a further embodiment there is provided a recombinant polypeptide comprising at least one selenocysteine residue at a selected position produced by a expressing a nucleic acid encoding polypeptide in a bacterial strain according the embodiments and in the presence of selenium source and purifying the recombinant polypeptide from the bacteria.

A further embodiment provides a culture of bacteria comprising an expressed recombinant polypeptide in an amount of 5 to 100 mg/L of the culture. In certain aspects, the expressed recombinant polypeptide comprises at least one selenocysteine residue. In some aspects, the culture of bacteria comprises an expressed recombinant polypeptide in an amount of 10 to 40 mg/L of the culture, said expressed recombinant polypeptide comprising at least one selenocysteine residue. In certain aspects, the expressed recombinant polypeptide is present in an amount of 5 to 50 mg/L, 10 to 80 mg/L, 15 to 60 mg/L, 10 to 30 mg/L, 20 to 80 mg/L, 30 to 90 mg/L, 40 to 80 mg/L, 50 to 70 mg/L, 60 to 90 mg/L, 70 to 80 mg/L, or 90 to 100 mg/L of the culture. In certain aspects, the expressed recombinant polypeptide is present in an amount of 5 to 10 mg/L, 7 to 15 mg/L, 10 to 20 mg/L, 15 to 30 mg/L, 20 to 35 mg/L, 30 to 40 mg/L, 35 to 45 mg/L, 40 to 50 mg/L, 45 to 55 mg/L, 50 to 50 mg/L, 55 to 65 mg/L, 50 to 60 mg/L, 65 to 70 mg/L, 75 to 85 mg/L, 85 to 90 mg/L, 80 to 95 mg/L, 85 to 98 mg/L, or 95 to 100 mg/L of the culture. In certain aspects, the expressed recombinant polypeptide is in an amount of at least 1 mg/L, 5 mg/L, 10 mg/L, 15 mg/L, 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 85 mg/L, 90 mg/L, 95 mg/L, 100 mg/L or higher in the culture.

In some aspects, the expressed recombinant polypeptide is a polypeptide of the embodiments (e.g., a polypeptide at least 85%, 90%, 91%, 92%, 93%, 94%, 95%, 96%, 97%, 98% or 99% identical to one of the polypeptides of SEQ ID NO: 1 and comprising one of the substitutions listed in Table 1). In certain aspects, the expressed recombinant polypeptide comprises at least one selenocysteine residue at a selected position not found a wild type version of the polypeptide. In some aspects, at least 80% of the expressed recombinant polypeptides in the culture comprise the selenocysteine residue at the selected position. In certain aspects, 80%-99.9% of the recombinant polypeptides in the culture comprise the selenocysteine residue at the selected position. In some aspects, 90%-99% of the expressed recombinant polypeptides in the culture comprise the selenocysteine residue at the selected position. In some aspects, at least 95% of the expressed recombinant polypeptides in the culture comprise the selenocysteine residue at the selected position. In some aspects, at least 99% of the expressed recombinant polypeptides in the culture comprise the selenocysteine residue at the selected position. In some aspects, the expressed recombinant polypeptide is at least 90% identical to a human polypeptide. In certain aspects, the human polypeptide is a polypeptides involved in a disease. In some aspects, the expressed recombinant polypeptide comprises an antibody or an enzyme. In certain aspects, the polypeptide comprises at least two selenocysteine residues at selected positions. In some aspects, the two selenocysteine residues at the selected positions form a diselenide bond. In specific aspects, the polypeptide comprises 2, 3, 4, 5, 6, 7, 8, 9 or 10 selenocysteine residues at selected positions. An even further embodiment provides a polypeptide comprising at least a first selenocysteine residues purified from a culture of the embodiments. In yet another embodiment, there is provided a method of expressing a polypeptides comprising at least one selenocysteine residue comprising: (a) expressing a nucleic acid encoding the polypeptide in a bacterial strain of the embodiments and in the presence of a selenium source; and (b) purifying the recombinant polypeptide from the bacteria. In another embodiment, there is provided a recombinant polypeptide comprising at least one selenocysteine residue at a selected position produced by a method comprising: (a) expressing a nucleic acid encoding the polypeptide in a bacterial strain of the embodiments and in the presence of a selenium source; and (b) purifying the recombinant polypeptide from the bacteria.

In an even further embodiment, there is provided the use of a bacterial strain of the embodiments as a host for production of a polypeptide comprising at least one selenocysteine residue. In further aspects, the bacterial strain is cultured in a medium comprising a selenium source.

In a further embodiment there is provided a transgenic bacterial strain comprising heterologous nucleic acids encoding translation components for incorporation of at least a first non-canonical amino acid and a screenable or selectable marker polypeptide that exhibits enhanced activity when at least one position of the marker polypeptide is said first non-canonical amino acid. In specific aspects, the screenable marker is a fluorescent or luminescent polypeptide. In further aspects, the bacterial strain comprises at least one nucleic acid molecule of the embodiments or expressing at least one polypeptide of the embodiments (e.g., a polypeptide at least 90% identical to one of the polypeptides of SEQ ID NO: 1 and comprising one of the substitutions listed in Table 1).

In other aspects, the bacterial strain comprises a heterologous nucleic acid encoding a selectable marker that exhibits enhanced activity when at least one position of the marker polypeptide is said first non-canonical amino acid. In further aspects, the selectable marker is a polypeptide that provides antibiotic resistance. In particular aspects, the selectable marker is a beta-lactamase enzyme.

In some aspects, the bacterial stain is a Gram positive or a Gram negative bacterial cell. In some specific aspects, the bacterial cell is an *E. coli* cell. In other particular aspects, the bacterial cell is an *Enterobacter* or *Serratia* bacteria. In further aspects, the bacterial cell is an *Enterobacter cloacae* or *Serratia marcescens* bacterial cell.

In certain aspects, the translation components for incorporation of the first non-canonical amino acid comprise a nucleic acid encoding a tRNA and an aminoacyl-tRNA synthetase for the first non-canonical amino acid. In some aspects, the tRNA recognizes a UAG codon. In further aspects, the tRNA is at least 85%, 90%, 91%, 92%, 93%, 94%, 95%, 96%, 97%, 98% or 99% identical to SEQ ID NO: 20, SEQ ID NO: 21, SEQ ID NO: 22 or SEQ ID NO: 23. In specific aspects, the tRNA comprises SEQ ID NO: 20, SEQ ID NO: 21, SEQ ID NO: 22 or SEQ ID NO: 23.

In still further aspects, the translation components for incorporation of the first non-canonical amino acid further comprise a nucleic acid encoding an enzyme for synthesis for the first non-canonical amino acid. In a particular aspect, the non-canonical amino acid is selenocysteine. In other aspects, the cell comprises a nucleic acid encoding selA, selB and/or selC. In a specific aspect, the cell comprises a nucleic acid encoding selA. In some aspects, the bacterial cell comprises an inactivated or deleted prfA gene. In certain aspects, the cell has been engineered to lack endogenous Amber (TAG) codons. In some particular aspects, the cell is or is derived from a *E. coli* C321. ΔA.

In a further embodiment the invention provides a population of bacterial cells in accordance with the embodiments and aspects described above. In certain aspects, the population comprises $1\times10^3$ to $1\times10^{12}$ bacterial cells.

In still a further embodiment, there is provided a method of producing a commercial polypeptide comprising at least a first non-canonical amino acid comprising (i) obtaining a bacterial strain according to the embodiments and an expression cassette encoding the commercial polypeptide; and (ii)

incubating the bacterial strain in conditions that allow expression of the commercial polypeptide. In some aspects, the expression cassette encoding the commercial polypeptide is under the control of an inducible promoter. In certain aspects, the method further comprises isolating the expressed commercial polypeptide.

In yet still a further embodiment, the invention provides a method of screening for a polypeptide having a desired activity comprising (i) obtaining a population of bacterial cells according to the embodiments, said cells encoding a library of candidate polypeptides, said polypeptides comprising at least a first non-canonical amino acid position; and (ii) screening the population of bacteria to identify a candidate polypeptide having the desired biological activity. In specific aspects, the population of bacterial cells comprises nucleic acid constructs encoding 100 to 10,000,000 different candidate polypeptides.

In still a further embodiment, there is provided a recombinant nucleic acid molecule, wherein the molecule encodes a tRNA that is at least 85%, 90%, 91%, 92%, 93%, 94%, 95%, 96%, 97%, 98% or 99% identical to SEQ ID NO: 20, SEQ ID NO: 21, or SEQ ID NO: 22 and comprising one or more of the following features: a G or C at a position corresponding to position 7; a T at a position corresponding to position 49; an A or C at a position corresponding to position 50; a T at a position corresponding to position 64; a G or A at a position corresponding to position 65; and/or a G, T or C at a position corresponding to position 66. In some particular aspects, the molecule encodes a tRNA comprising the sequence at least about 90% identical to SEQ ID NO: 20; and comprises one or more of the features listed above. In further specific aspects, the molecule comprises 2, 3, 4, 5 or 6 of the features listed above. In certain aspects, the molecule encodes a tRNA comprising the sequence at least about 90% identical to SEQ ID NO: 21 or SEQ ID NO: 19. In particular aspects, the molecule encodes a tRNA comprising the sequence of SEQ ID NO: 20, SEQ ID NO: 21, or SEQ ID NO: 22.

In yet still a further embodiment there is provided a recombinant polypeptide, encoding a beta-lactamase enzyme, said enzyme comprising a disulfide bond between two cysteine positions that is required for activity of the enzyme, where at least one of said two cysteine positions is substituted with a selenocysteine. In some aspects, both of said cysteine residues are substituted with a selenocysteine. In further aspects, the beta-lactamase enzyme is a SME-type beta-lactamase or NMC-A beta-lactamase. For example, the beta-lactamase can comprises a sequence least 85%, 90%, 91%, 92%, 93%, 94%, 95%, 96%, 97%, 98% or 99% identical to SEQ ID NO: 24 and wherein the positions corresponding to C69 and/or C238 are selenocysteine. In certain aspects, the positions corresponding to C69 and C238 are selenocysteine.

Further embodiments of the invention provide a recombinant nucleic acid molecule encoding the polypeptide according to the embodiments and aspects described above. In some aspects, the codons corresponding to the selenocysteine position(s) is a UAG codon. In other aspects, the sequence is at least about 85%, 90%, 91%, 92%, 93%, 94%, 95%, 96%, 97%, 98% or 99% identical to SEQ ID NO: 25.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIGS. 1B and 1C, the lines, from top to bottom, at time 16 h represent MOPS EZ, Se Only, Se+Carb, and Carb Only.

In FIG. 2A, the lines, from top to bottom, at time 16 h represent LB, 100 Carb, 1000 Carb, and 10000 Carb with the lines for 1000 Carb and 10000 Carb being overlapping. In FIG. 2B, the lines, from top to bottom, at time 16 h represent LB, 100 Carb, 1000 Carb, and 10000 Carb with the lines for 100 Carb and 1000 Carb being overlapping.

FIGS. 3A-3B: *E. coli* strains for the production of selenoproteins contain a set of mutations which significantly enhances cell growth in defined media. The parental *E. coli* strain (FIG. 3A) has an extended lag phase and displays poor growth in a defined growth medium. An *E. coli* strain for the production of recombinant selenoproteins (FIG. 3B) containing a series of mutations has a higher growth rate, final cell density and selenocysteine dependent resistance to β-lactam antibiotics. For reproducibility and quality assurance, defined growth media are commonly used for the commercial production of recombinant proteins. In FIGS. 3A and 3B, the lines, from top to bottom, at time 20 h represent MOPS EZ, Se Only, Se+Carb, and Carb Only.

FIGS. 4A-4B: Intact mass spectrum and UVPD fragmentation map of *E. coli* dihydrofolate reductase containing a diselenide bond. The mass spectrum of *E. coli* DHFR (FIG. 4A, average masses shown) confirms incorporation of two selenocysteine residues with approximately 100% efficiency. No masses corresponding to the incorporation of either one or two serine residues were detected. UVPD fragmentation mapping (FIG. 4B, SEQ ID NO: 26) confirms incorporation of selenocysteine (U) at positions 39 and 85 and the formation of a diselenide bond. Diselenide bond formation is indicated by the lack of ions corresponding to fragmentation events between the two selenocysteine residues. Yield of DHFR was 8 mg/L. Other proteins containing a diselenide bond have been expressed at yields exceeding 40 mg/L.

FIGS. 5A-5C: Mass spectrum and UVPD fragmentation map of anti-MS2 scFv containing two essential diselenide bonds. An *E. coli* strain developed for the expression of recombinant selenoproteins enables the production of diselenide stabilized antibody fragments in the bacterial cytoplasm. Unlike the *E. coli* strains developed for the expression of proteins containing disulfide bonds, this strain does not require an elevated cytoplasmic redox potential. The experimentally determined monoisotopic mass (FIG. 5A) is consistent with a recombinant anti-MS2 scFv containing four selenocysteine residues which have formed two diselenide bonds. Diselenide bond formation is indicated by the loss of four protons (FIG. 5A, row 3 vs. row 2). Intact mass spectrum of the anti-MS2 scFv containing four selenocysteine residues (FIG. 5B) displayed as average masses. No masses corresponding to incorporation of serine residues were detected. UVPD fragmentation mapping (FIG. 5C, SEQ ID NO: 27) confirms incorporation of selenocysteine (U) at positions 42, 116, 179 and 249 and also diselenide bond formation. Diselenide bond formation is indicated by the lack of ions corresponding to fragmentation events between the pairs of selenocysteine residues, U42:U116 and U179:U249).

In FIGS. 6B and 6D, the lines, from top to bottom, at scFv conc 10 nM represent 0 mM DTT, 1 mM DTT, 10 mM DTT, and 50 mM DTT.

FIGS. 7A-7C: UVPD fragment maps of trastuzumab (Herceptin) scFvs produced in *E. coli* strains BL21DE3 (FIG. 7A, SEQ ID NO: 30), T7 Shuffle Express (FIG. 7B, SEQ ID NO: 30) and RTΔA-2X310K (FIG. 7C, SEQ ID NO: 31). For the 193 nm UVPD sequence information shown above, covalently bonded (or potentially bonded) cysteine residues (FIG. 7B) and covalently bonded selenocysteine residues (FIG. 7C) are shaded in gray. (FIG. 7A) Even fragmentation throughout the protein sequence in indicates no formation of disulfide bonds. (FIG. 7B) Lack of fragmentation in the second half of the sequence confirms formation of a disulfide bond in the VH region only. No disulfide bond formed in the VL region despite expression in oxidizing conditions. (FIG. 7C) Lack of fragmentation in both the VL and VH regions confirms formation of two diselenide bonds. Only the diselenide scFv adopted the native and expected covalent architecture.

DESCRIPTION OF ILLUSTRATIVE EMBODIMENTS

Figure 1A:
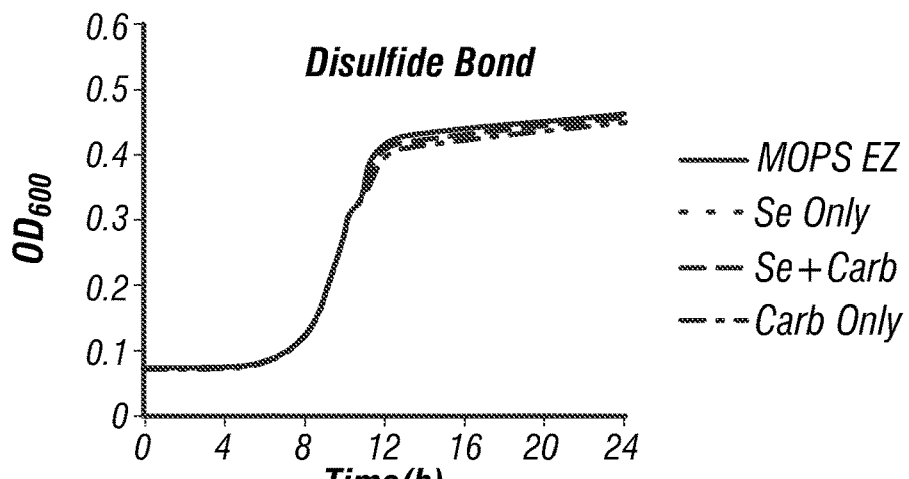
FIGS. 1A-1C: *E. coli* strains for production of selenoproteins are conditionally dependent on selenocysteine for growth and survival. An *E. coli* strain containing an integrated β-lactamase with the native disulfide bond (FIG. 1A) does not require selenium supplementation to survive in the presence of the β-lactam antibiotic carbenicillin. *E. coli* strains with either one (FIG. 1B) or two (FIG. 1C) essential selenocysteine residues, which form either a selenyl-sulfhydryl or diselenide bond, respectively, require selenium for resistance to β-lactam antibiotics. Conditional dependence on selenocysteine incorporation prevents loss or attenuation of the otherwise toxic selenocysteine biosynthesis and incorporation machinery.

The use of non-canonical amino acids in proteins offers the possibility of polypeptides having greatly expanded functionality that could be exploited for wide range of applications. For example, by incorporation of selenocysteine into polypeptides it may be possible to develop enzymes having enhanced levels of stability or activity and to produce highly active therapeutic polypeptides. However, these approaches have, to date, been hampered by the inability to produce organisms that stably retain translation pathways and that predictable and reliably incorporate selenocysteine into encoded polypeptides. Accordingly, the present disclosure overcomes challenges associated with current technologies by providing an evolved *E. coli* strain and advanced *E. coli* genes capable of efficient selenocysteine protein production. Particularly, for the first time commercially relevant amounts of selenoproteins showing essentially complete incorporation of encoded selenocysteine residues can be achieved. Bacterial strains and mutant genes that enable this production are also provided. For example, studies presented here have identified several point mutations in genes, including acrB, adhE, arcB, cysK, dnaE, ftsA, and ftsL, that optimize survival in selenium enriched media and contains pathways to ensure dependence on selenocysteine is maintained. One exemplary bacterial strain is the mutant RTΔA 2X310K *E. coli* strain which contains these core mutations providing enhanced growth rates, greater final cell density and approximately 100% incorporation of selenocysteine in polypeptides produced using this strain. Thus, methods and compositions are provided herein for the efficient incorporation of selenocysteine and for production of polypeptides that incorporate selenocysteine positions.

I. System for Selenocysteine Incorporation

Embodiments of the present disclosure provide a system for the incorporation of selenocysteine, such as for the production of selenoproteins. In one aspect, the system is a bacterial strain, such as an *E. coli* strain, which comprises one or more amino acid substitutions or deletions within one or more of the genes which enhance cell growth or selenocysteine incorporation. The bacterial strain may be *E. coli* strain K012 MG1655 (GenBank Accession No. U00096.3), E. coli stain C321ΔA (US2016/0060301), or E. coli strain RTΔA. In certain embodiments the bacterial strain is the RTΔA 2X310K strain.

In particular aspects, the system comprises evolved bacterial strains which are conditionally dependent on selenocysteine. In one example, the evolved bacterial strain is derived from a strain, such as the RTΔA strain, which comprises deletions of the genomic selA, selB and selC genes (encoding SelA, SelB and tRNA$^{Sec}$, respectively) and which lacks the prfA gene encoding release factor 1 (RF1) allowing for efficient incorporation of a range of unnatural amino acids. The deletion of these genes eliminated any crosstalk between a UAG suppressing tRNA (e.g., tRNA$^{SecUx}$) and the endogenous selenocysteine incorporation machinery. In addition, the RTΔA strain contains a reporter protein to selenocysteine, the NMC-A β-lactamase from *Enterobacter cloacae* with an essential selenyl-sulfhydryl or diselenide bond (ΔaphC::nmcA C69U C238 or C69U C238U) rendering conditional dependence on selenocysteine incorporation for resistance to β-lactam antibiotics. Conditional dependence on selenocysteine incorporation prevents loss or attenuation of the otherwise toxic selenocysteine biosynthesis and incorporation machinery. The efficiency of selenocysteine incorporation may be enhanced by the expression of an evolved tRNA for site specific incorporation of selenocysteine (e.g., for example, tRNA$^{SecUx}$; U.S. Patent App. Publn. 2017/0166945, incorporated herein by reference). Further enhancements may include expression of various genes including, but not limited to, a selD, selA and/or pstK gene. For example, a bacterial strain could express E. coli selD, E. coli selA and M. jannaschii pstK.

In certain embodiments, the selenocysteine-incorporating system encodes for one or more E. coli genes with one or more amino acid deletions or substitutions. The genes can include acrB (SEQ ID NO:1), adhE (SEQ ID NO:2), arcB (SEQ ID NO:3), cysK (SEQ ID NO:4), dnaE (SEQ ID NO:5), ftsA (SEQ ID NO:6), ftsL (SEQ ID NO:18), hemA (SEQ ID NO:7), mdfA (SEQ ID NO:8), ompR (SEQ ID NO:9), oxyR (SEQ ID NO:19), pcnB (SEQ ID NO:10), prfB (SEQ ID NO:17), pta (SEQ ID NO:11), queE (SEQ ID NO: 69), and/or ydiL (SEQ ID NO:13). Additional genes include pdxB (SEQ ID NO:14), yeeJ (SEQ ID NO:15), and yphG (SEQ ID NO:16). For example, a selenocysteine-incorporating bacterial strain could comprise a T246A mutation in the prfB gene in combination with at least one hemA mutation. As another example, a selenocysteine-incorporating bacterial strain could comprise a T246A mutation in the prfB gene in combination with at least one hemA mutation and at least one yeeJ mutation. Exemplary amino acid substitutions for these genes are depicted in Table 1.

TABLE 1

Mutations enriched in evolved strains.

| E. coli gene | Mutation(s) |
| --- | --- |
| AcrB (SEQ ID NO: 1) | A999T, A457T, L344P, L591P:A183T, F358L, G23R, M902I, L230R, A889V:R620C, D174G |
| AdhE (SEQ ID NO: 2) | R702H |
| ArcB (SEQ ID NO: 3) | T655A, R398C, T652A, R264C, V21A |
| CysK (SEQ ID NO: 4) | I45N, F290L, G271D, T73A, H153Y, I45V, L284P, T73I, P68L, T69I, R305C, F144S:A281V |
| DnaE (SEQ ID NO: 5) | E916G, Y938H, R860H, E781G, G925D, T470M |
| FtsA (SEQ ID NO: 6) | T115A, G386R, A136V, Q155R, P98S:E201A, A294T, H159Y, V112I |
| HemA (SEQ ID NO: 7) | A173V, V183A, P196L, L180F, D127A:S249A, A5V:P273L, A5V, I176N |
| MdfA (SEQ ID NO: 8) | M1R |
| OmpR (SEQ ID NO: 9) | Y102C, R15C, Q30R |
| PcnB (SEQ ID NO: 10) | R105C |
| Pta (SEQ ID NO: 11) | A119V, S535P, W373R, P673L, P673S, S535P, A119T, D601A, AS19T:P673L, E103K, G31D, T662I, E359K:N519D |
| QueE (SEQ ID NO: 12) | A69G |
| YdiK (SEQ ID NO: 13) | L107S |
| PdxB (SEQ ID NO: 14) | V212I, D162N, T299A, C220R |
| YeeJ (SEQ ID NO: 15) | S1467P, V1184A, S1730N, G1888D, A352T, G374S, S1423R, D1502E, R285Q, E470K, A939T, L1669F, V2034I, S1713N, D1233N, A704T, M1084I |
| YphG (SEQ ID NO: 16) | S112F, T126A, P978L, E199G, A476T, A735V |
| PrfB (SEQ ID NO: 17) | T246A |

TABLE 1-continued

Mutations enriched in evolved strains.

| E. coli gene | Mutation(s) |
|---|---|
| FtsI (SEQ ID NO: 18) | V545I, D76G:A293V, A537T, A3V:P311S, M471T, A228V:P311S, A257T |
| OxyR (SEQ ID NO: 19) | M193I, A233T, L124P, V300A, C199R |

Mutations in bold are core mutations in *E. coli* RTΔA 2X310K.

In additional aspects, the *E. coli* genes may be further modified by one or more other amino substitutions. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in selenocysteine-containing polypeptides and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the selenocysteine-containing polypeptides described herein may be modified by the substitution of an amino acid, for different, but homologous amino acid with a similar hydrophilicity value. Amino acids with hydrophilicities within +/−1.0, or +/−0.5 points are considered homologous.

II. Production of Recombinant Polypeptides Comprising Selenocysteine

The selenocysteine-incorporating system provided herein may be used for the production of polypeptides comprising selenocysteine, such as antibodies or disulfide-bonded proteins. In some cases a selenocysteine residue can be substituted for a naturally occurring cysteine, or at any site in which substitution of a selenocysteine residue does not alter the structure and function of the polypeptide, e.g., at a serine residue. In still further aspects, method according to the embodiments can be used to produce polypeptides that naturally comprise one or more selenocysteine residues, such a human selenoprotein (e.g., human TrxR).

In certain embodiments, a nucleic acid (e.g., plasmid) encoding the polypeptide can be introduced to the system and cultured in selenium-containing growth medium under conditions in which the cell incorporates at least one selenocysteine residue into the polypeptide. The resultant selenocysteine-containing polypeptide can then be isolated and analyzed such as by mass spectrometry or x-ray crystallography.

The nucleic acids can be introduced into and maintained in the cell in a recombinant vector that is capable of autonomously replicating in the cell according to standard techniques. The method of transformation, and the choice of expression vehicle, will depend on the nature of the polypeptide to be expressed and the host system selected. Transformation methods are described, e.g., in Ausubel et al. (eds.) Current Protocols in Molecular Biology (John Wiley & Sons, New York, 1994); expression vehicles can be chosen from those well-known in the art, e.g., in Cloning Vectors: A Laboratory Manual (P. H. Pouwels et al., 1985, Suppl. 1987). To induce expression of the heterologous polypeptide, the cell culture medium typically contains between 1 and 50 ng/ml, preferably 2 to 40 ng/ml, and most preferably 5 to 25 ng/ml of selenium. The selenium may be present as sodium selenite or another soluble, oxidized form of selenium, (e.g., 0.1 to 50 µM, particularly 5 to 25 µM $Na_2SeO_3$, can be used). By "heterologous" nucleic acid is meant a nucleic acid which is partly or entirely foreign to the cell or animal in which it is introduced, or a nucleic acid which is homologous to an endogenous gene of the cell or animal with the exception that the heterologous protein contains selenocysteine substituted for at least one amino acid.

In order to obtain expression of the nucleic acid sequences, the sequences may be incorporated in a vector having one or more control sequences operably linked to the nucleic acid to control its expression. The vectors may include other sequences such as promoters to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptides can then be obtained by transforming the vectors into host cells in which the vector is functional, culturing the host cells so that the polypeptide is produced and recovering the polypeptide from the host cells or the surrounding medium. Prokaryotic cells useful in embodiments of the present invention include *E. coli*, and strains which have T7 RNA polymerase may be preferred for ease of overexpression.

In some cases the selenocysteine residue can be substituted for a naturally occurring cysteine, or at any site in which substitution of a selenocysteine residue does not alter the structure and function of the polypeptide, e.g., at a serine residue. Such amino acids can be identified by means well known to those skilled in the art, and will usually occur at positions that are not involved in the catalytic or binding activity of the protein (as determined for example by mutational analysis), or at positions considered critical for the structural integrity of the polypeptide. In particular polypeptides, the selenocysteine residues may be incorporated in positions that normally would be occupied by two cysteine residues that form a disulfide bridge; thus, the selenocysteine residues will form a diselenide bond that is identifiable by mass spectrometry. Using standard techniques, the selenocysteine can also be modified to form a selenide, selenoxide, seleninic acid, selenonic acid, selenone, or a selenosulfur group.

In another embodiment, a selenocysteine residue is incorporated at a site in a polypeptide in which the substitution is known (or predicted) to alter the structure and/or function of the polypeptide. This may be to improve the function or characteristics of the polypeptide, to help determine the biological function of the polypeptide, to determine the structure of the polypeptide or for purification of the polypeptide, e.g., to aid in identification of a polypeptide domain, an active site, or a binding site for a drug or another polypeptide.

A. Antibodies with Selenocysteine

The recombinant polypeptide comprising selenocysteine can encode for an antibody, such as a monoclonal antibody. In some aspects, the selenocysteine residue can be substituted at a position that would be cysteine in the wild type antibody. The antibody may be an IgG, IgM, IgA or an antigen binding fragment thereof. In certain aspects, the antibody is a Fab', a F(ab')2, a F(ab')3, a monovalent scFv, a bivalent scFv, or a single domain antibody. The antibody may be a non-human antibody, a murine antibody, a human antibody, humanized antibody or de-immunized antibody. In some cases the antibody may be conjugated to an imaging agent, a chemotherapeutic agent, a toxin or a radionuclide. Also provided herein is a composition comprising an antibody of the embodiments and aspects described herein in a pharmaceutically acceptable carrier.

As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Thus, by known means and as described herein, polyclonal or monoclonal antibodies, antibody fragments, and binding domains and CDRs (including engineered forms of any of the foregoing) may be produced that contain at least one selenocysteine residue. In some aspects, the antibody comprises at least two selenocysteine residues that can form a diselenide bond.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Antibodies may be produced from any animal source, including birds and mammals. Preferably, the antibodies are bovine, ovine, murine, rat, rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

In some aspects an antibody having a selenocysteine residue can be an antibody for use as a therapeutic. For example, an antibody can comprise the CDR sequences of a commercial antibody therapeutic such as Cetuximab.

III. Deposit Information

A representative frozen deposit of *E. coli* strain RTΔA 2X310K has been made with the National Collections of Industrial, Food and Marine Bacteria (NCIMB), 23 St. Machar Drive, Aberdeen AB2 1RY, Scotland, United Kingdom on Jun. 22, 2016. Those deposited cells have been assigned Accession No. NCIMB 42595.

The foregoing deposit was made in accordance with the terms and provisions of the Budapest Treaty relating to deposit of microorganisms and were made for a term of at least thirty (30) years and at least five (05) years after the most recent request for the furnishing of a sample of the deposits is received by the depository, or for the effective term of the patent, whichever is longer, and will be replaced if it becomes non-viable during that period.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production and Characterization of RTΔA 2X310K

Several bacterial strains were produced for selenocysteine incorporation and then evolved. A previously described *E. coli* RTΔA stain (Thyer et al., 2015; incorporated herein by reference) was used for the derivation of more efficient selenocysteine incorporating strains. Briefly, the RTΔA strain comprises deletions of the selA, selB and selC genes (encoding SelA, SelB and tRNA$^{Sec}$, respectively) in strain C321.ΔA (Lajole et al., 2013) which lacks the prfA gene encoding release factor 1 (RF1) allowing for efficient incorporation of a range of unnatural amino acids. The deletion of these genes eliminated any crosstalk between the new tRNA$^{Sec}$ library and the endogenous selenocysteine incorporation machinery.

Figure 1B:
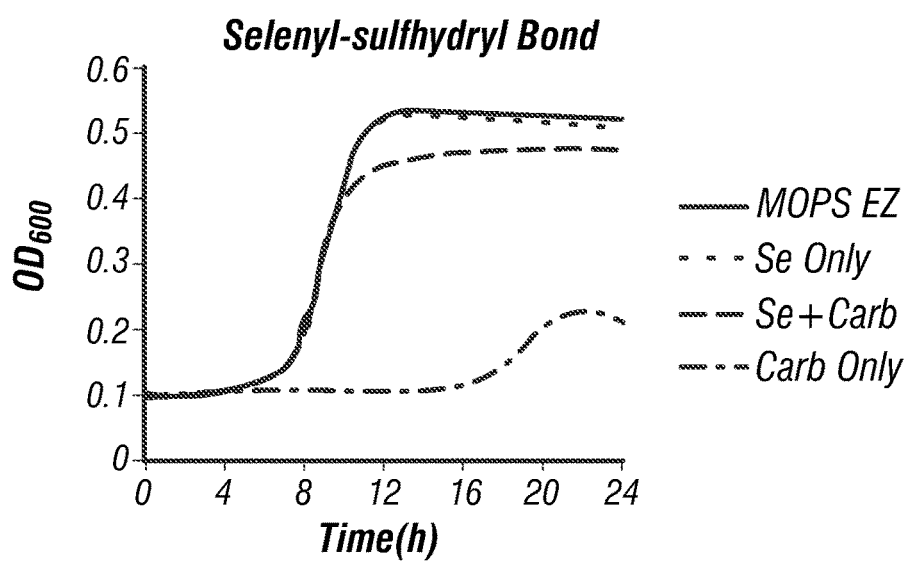
Figure 1C:
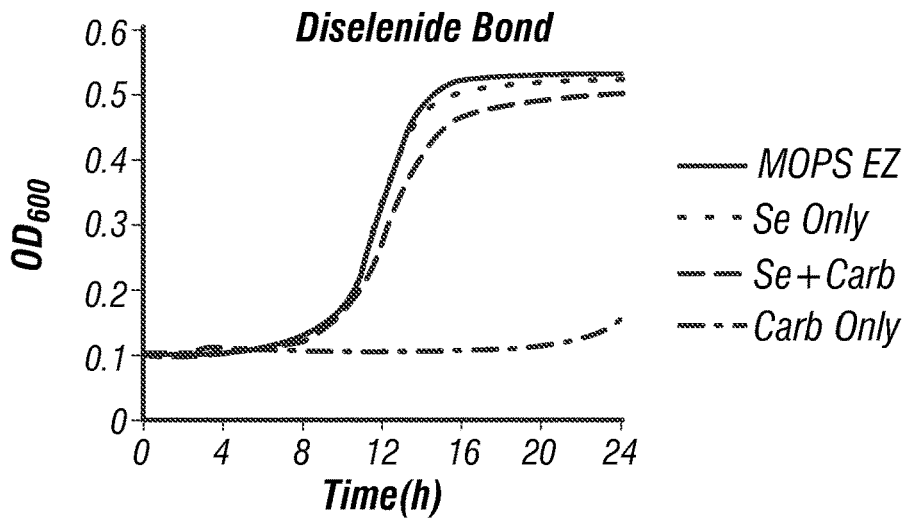

In addition, the RTΔA strain contains a selenocysteine dependent reporter protein, the NMC-A β-lactamase from *Enterobacter cloacae* with an essential selenyl-sulfhydryl or diselenide bond (ΔaphC::nmcA C69U C238 or C69U C238U) rendering conditional dependence on selenocysteine. This enzyme has high sequence similarity to the SME-1 β-lactamase from *Serratia marcescens*, an enzyme that has previously been shown to require a disulfide bond adjacent to the active site serine residue for activity, but that confers a significant fitness cost on *E. coli*. It was observed that an *E. coli* strain containing an integrated β-lactamase with the native disulfide bond did not require selenium supplementation to survive in the presence of the β-lactam antibiotic carbenicillin. *E. coli* strains with either one or two essential selenocysteine residues which form either a selenyl-sulfhydryl or diselenide bond respectively required selenium for resistance to β-lactam antibiotics (FIGS. 1A-1C). Conditional dependence on selenocysteine incorporation prevents loss or attenuation of the otherwise toxic selenocysteine biosynthesis and incorporation machinery.

Two plasmids were introduced which provide the machinery necessary for selenocysteine incorporation. The first plasmid contained a CloDF13 origin of replication and expressed the *E. coli* selD gene and an evolved tRNA for site specific incorporation of selenocysteine (tRNA$^{SecUX}$; U.S. Patent App. Publn. 2017/0166945). The second plasmid (containing a RSF1030 origin of replication) expressed the *E. coli* selA gene and the *M. jannaschii* pstK gene. Following transformation with these two plasmids, the NMC-A beta lactamase containing either zero, one or two selenocysteine residues in place of the essential disulfide bond forming cysteine residues was integrated into the genome at the aphC locus. This conferred selenocysteine dependent resistance to some beta-lactam antibiotics and served to set a minimum threshold for selenocysteine incorporation in the cells.

The resulting strains (in triplicate, along with control strains) were evolved for more than 2500 generations (205 passages to confluence) under two different conditions: increasing antibiotic concentration or increasing temperature. Following evolution, whole genome sequencing was performed on all strains. Strains contained between one and three hundred nonsynonymous mutations within coding regions. A subset of these mutations which were highly enriched (present in multiple independent lines) were introduced to the parental strain for characterization. These mutations (see, Table 1 above) conferred increased growth rate, viability, selenite resistance or other beneficial characteristics. All evolved strains showed dramatically improved growth compared to the parent strains in a variety of different conditions.

Figure 2A:
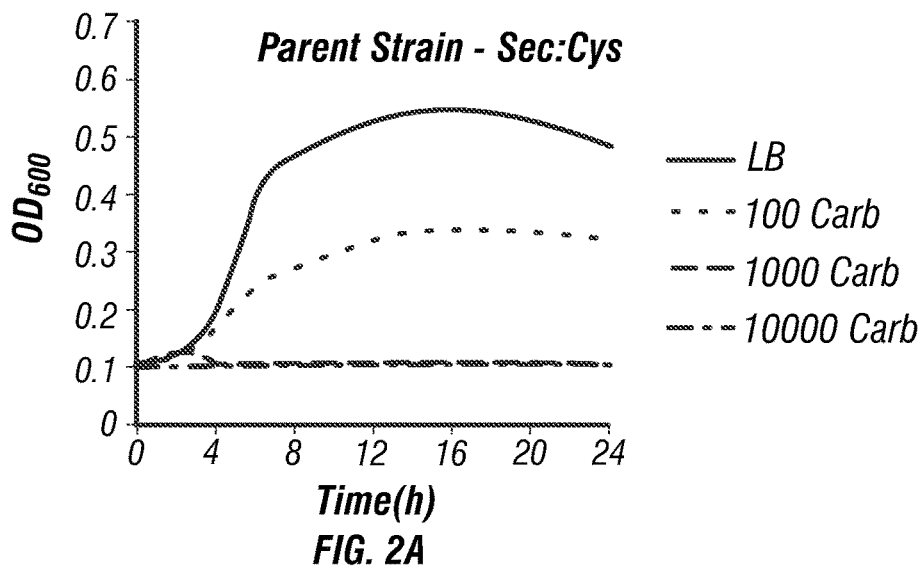
FIGS. 2A-2B: *E. coli* strains for the production of selenoproteins contain a set of mutations which significantly enhances cell growth and resistance to β-lactam antibiotics via selenocysteine dependent β-lactamase. A parental *E. coli* strain (FIG. 2A) has moderate resistance to β-lactam antibiotics mediated via a selenocysteine dependent β-lactamase during while growing in a rich medium. An *E. coli* strain for the production of recombinant selenoproteins (FIG. 2B) containing a series of mutations has a higher growth rate, final cell density and resistance to carbenicillin. This improved growth makes the mutant strain a superior host for the production of recombinant selenoproteins.
Figure 2B:
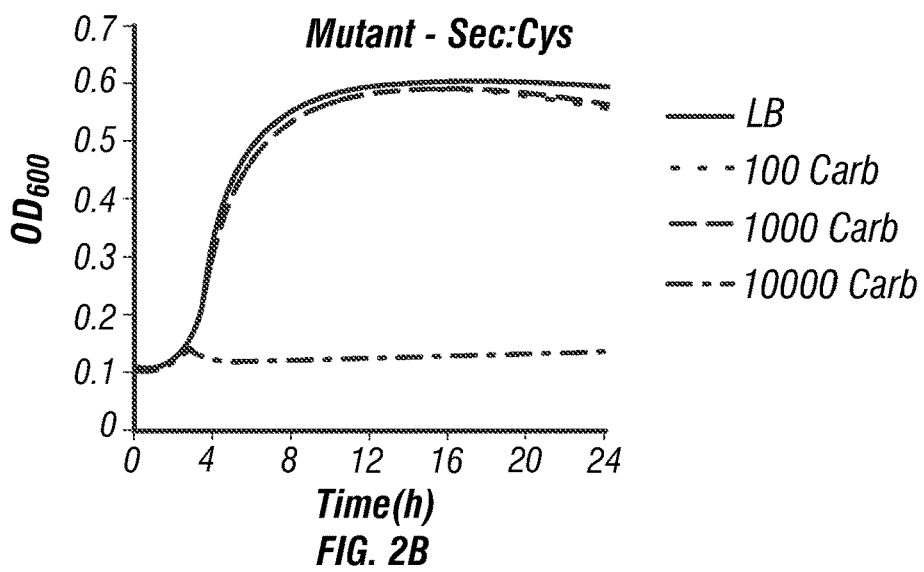
Figure 3A:
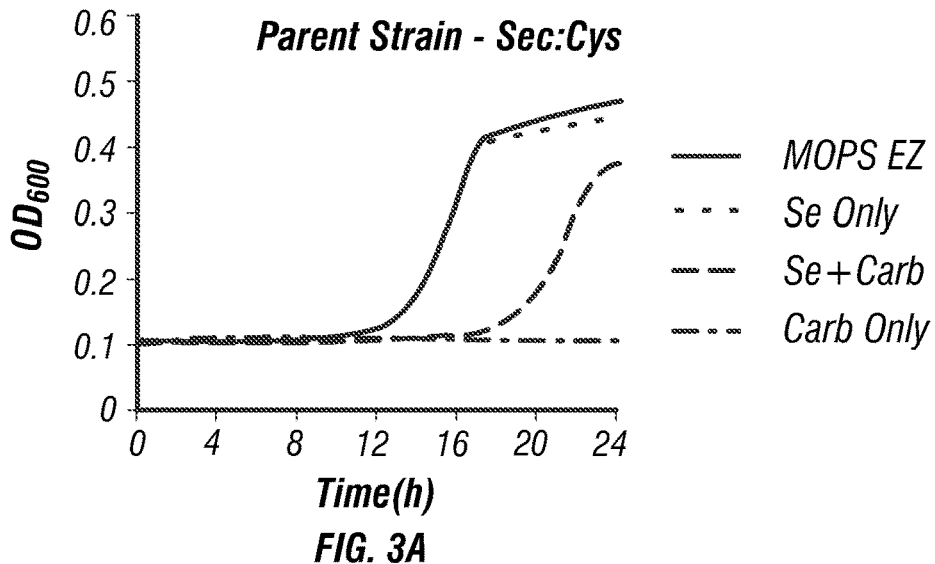

A single clone from one of the lines (designated 2X310K) was isolated and used to benchmark the potential of these evolved strains for recombinant selenoprotein production. This strain is capable of producing diselenide containing proteins with significant yields. While the parental RTΔA strain containing an integrated NMC-A beta lactamase with two selenocysteine residues showed moderate resistance to the β-lactam antibiotic carbenicillin, the mutant 2X310K strain showed a greater resistance to carbenicillin (FIGS. 2A-2B). This improved growth makes the mutant strain a superior host for the production of recombinant selenoproteins. In addition, while the parental strain showed an extended lag phase and poor growth in defined media, the mutant 2X310K strain showed a higher growth rate and final cell density (FIGS. 3A-3B).

To monitor the efficiency of selenocysteine incorporation and demonstrate the possibilities for protein engineering, *E. coli* dihydrofolate reductase (DHFR) was produced containing an engineered non-essential selenyl-sulfhydryl bond. Top down mass spectrometry showed close to 100% selenocysteine incorporation with no detectable background corresponding to DHFR containing serine. It was observed that the two selenocysteine residues were incorporated with approximately 100% efficiency at positions 39 and 85 (FIGS. 4A-4B). The analysis also confirmed the presence of a diselenide bond.

Figures 5A, 5B:
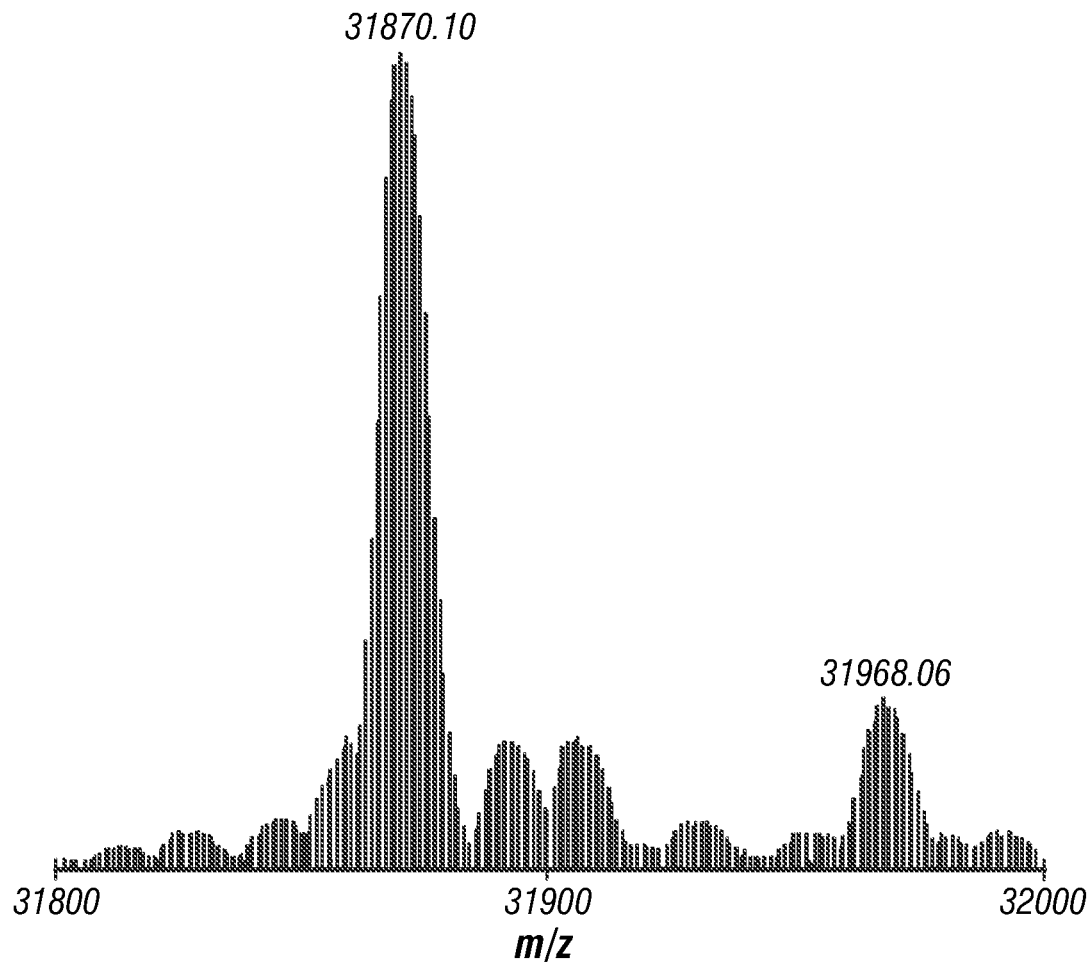

The mutant 2X310K strain was used to produce diselenide stabilized anti-MS2 antibody fragments in the bacterial cytoplasm. Unlike the *E. coli* strains developed for the expression of proteins containing disulfide bonds, this strain does not require an elevated cytoplasmic redox potential. The experimentally determined monoisotopic mass was consistent with a recombinant anti-MS2 scFv containing four selenocysteine residues which formed two diselenide bonds (FIGS. 5A-5C). Thus, the strain can efficiently produce stabilized selenoproteins. Further, the strain was engineered to contain the T7 RNA polymerase which will further increase the yield of recombinant selenoproteins.

Figures 6A, 6B:
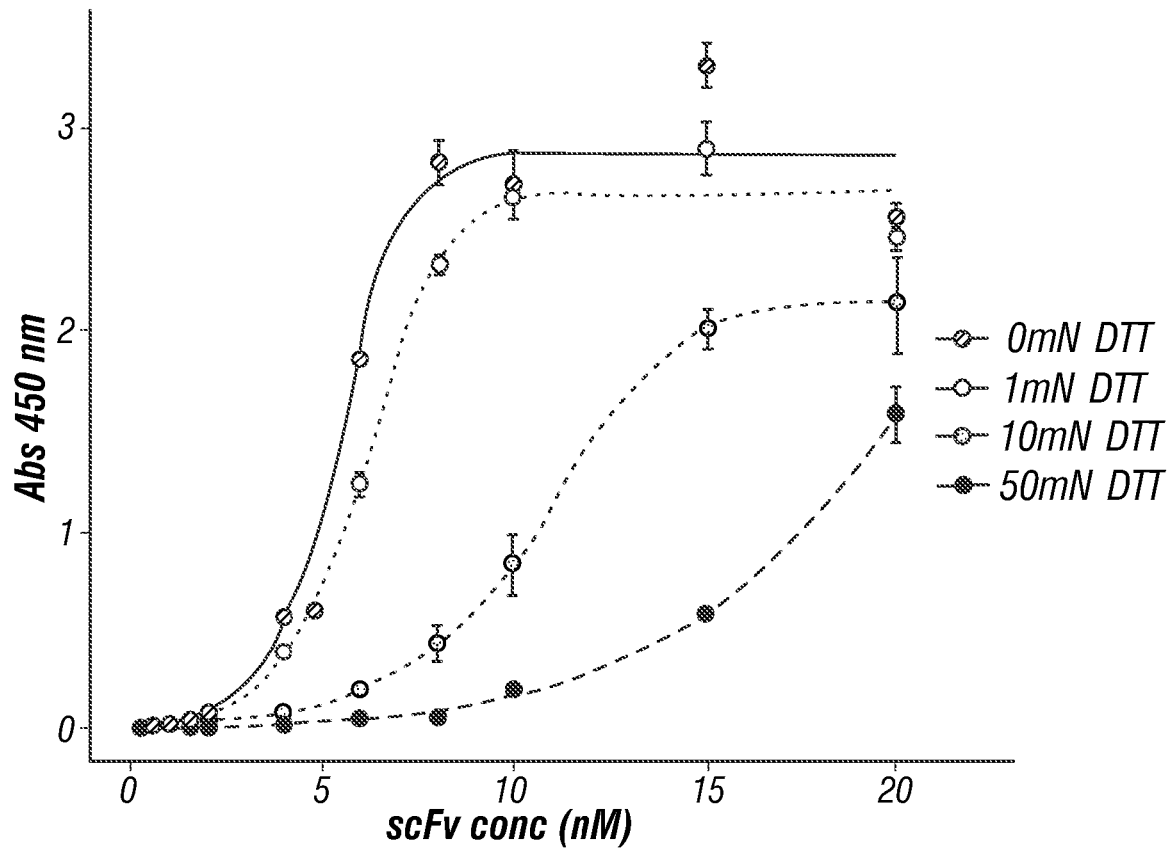
FIGS. 6A-6D: UVPD fragment maps and ELISA for wild-type anti-ricin A chain scFv (FIGS. 6A and 6B, respectively) and seleno anti-ricin A chain scFv (FIGS. 6C and 6D, respectively). For the 193 nm UVPD sequence information, covalently bonded (or potentially bonded) cysteine residues (FIG. 6A, SEQ ID NO: 28) and covalently bonded (or potentially bonded) selenocysteine residues (FIG. 6C, SEQ ID NO: 29) are shaded in gray. The gaps in sequence coverage indicate the formation of covalent disulfide bonds between the cysteine residues. The absence of fragmentation between the selenocysteine residues confirms formation of the two diselenide bonds. The bond connectivity is identical to the wild-type anti-ricin A chain scFv. Treatment of the wild-type anti-ricin A chain scFv with DTT leads to significant loss of activity (FIG. 6B). The selenocysteine containing scFv is strongly resistant to reducing conditions (FIG. 6D). Treatment with 50 mM DTT resulted in only a slight loss of affinity ($EC_{50}$ 7.95 nM to $EC_{50}$ 11.4 nM).
Figures 6C, 6D:
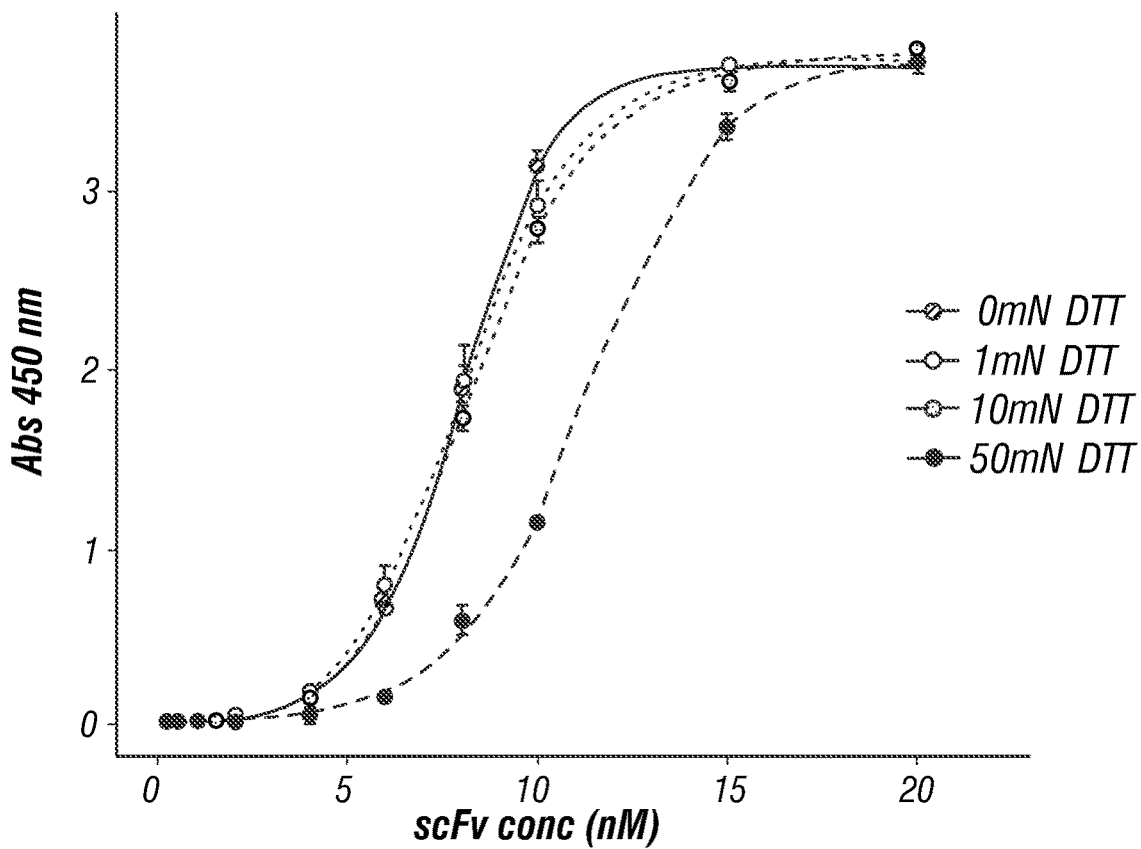

The mutant 2X310K strain was used to produce seleno anti-ricin A chain scFv. The absence of fragmentation between the selenocysteine residues in the UVPD sequence information, shown in FIG. 6C, confirms formation of the two diselenide bonds. The bond connectivity of the seleno anti-ricin A chain scFv is identical to the wild-type anti-ricin A chain scFv, shown in FIG. 6A. However, treatment of the wild-type anti-ricin A chain scFv with DTT leads to significant loss of activity (FIG. 6B), while the selenocysteine containing scFv is strongly resistant to reducing conditions (FIG. 6D).

Figures 7A, 7B:
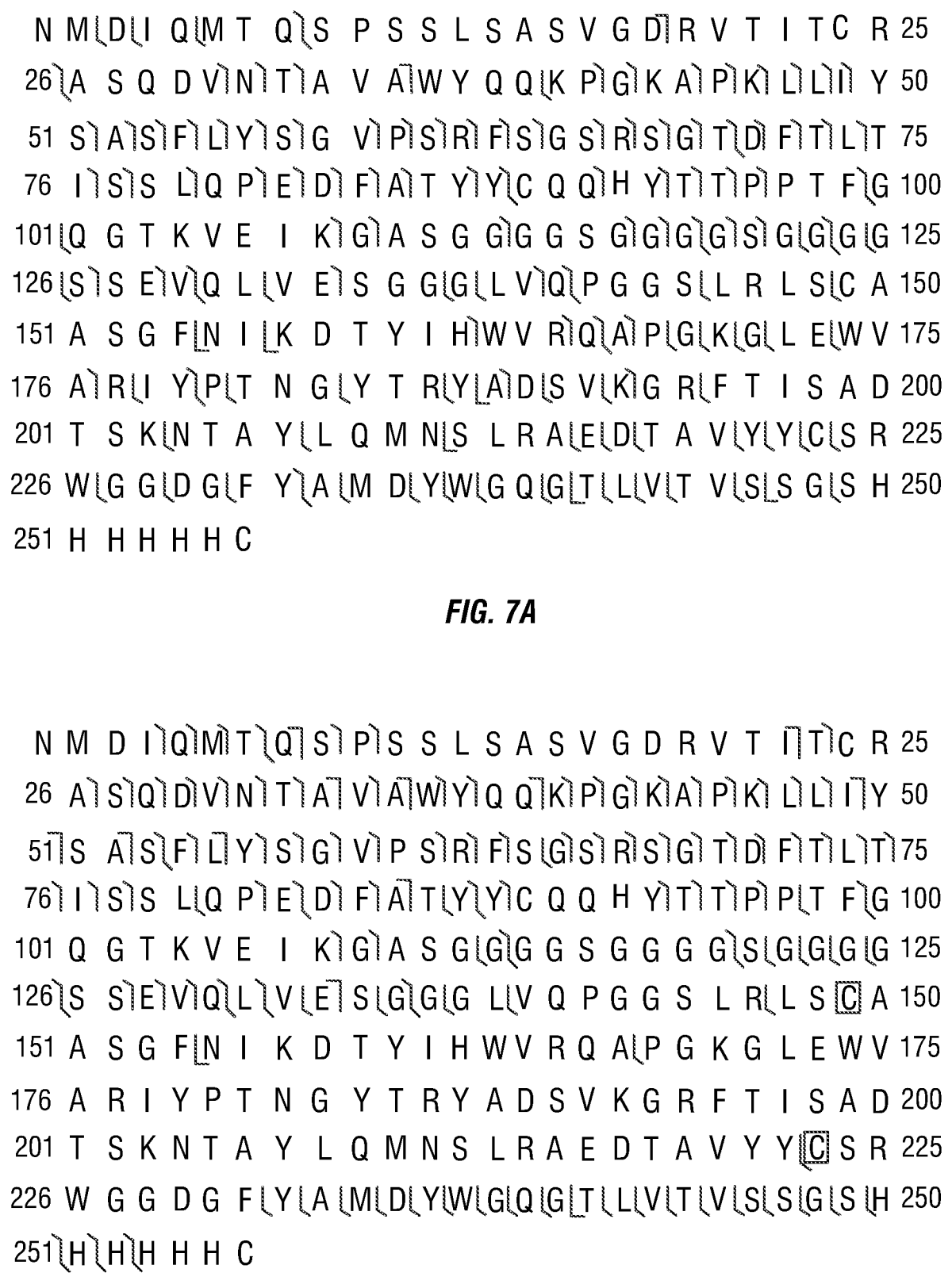
Figure 7C:
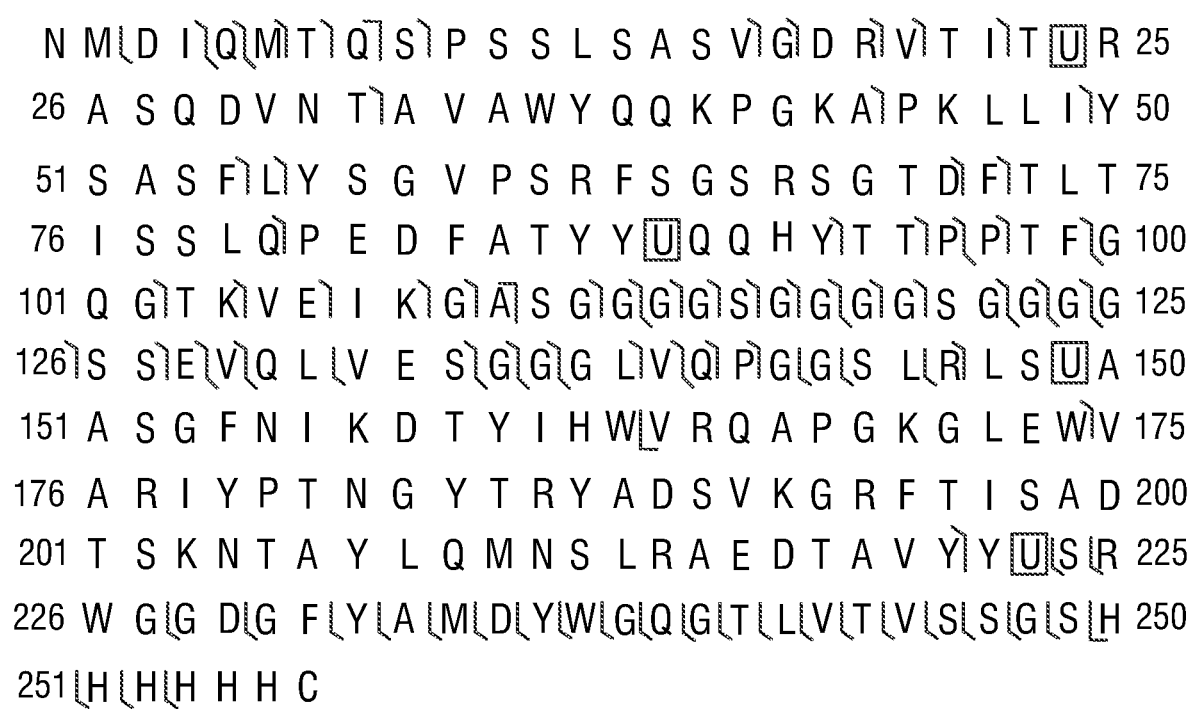

E. coli strains BL21DE3, T7 Shuffle Express, and RTΔA-2X310K were used to produce trastuzumab (Herceptin) scFvs. In the BL21DE3 strain, no disulfide bonds were formed, as can be seen by the even fragmentation through the protein sequence in FIG. 7A. In the T7 Shuffle Express strain, a disulfide bond formed in the VH region only, as can be seen by the lack of fragmentation in the second half of the sequence in FIG. 7B. However, in the RTΔA-2X310K strain, two diselenide bonds formed, as can be seen by the lack of fragmentation in both the VL and VH regions in FIG. 7C. Thus, only the diselenide scFv adopted the native and expected covalent architecture.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 5,091,513
U.S. Pat. No. 6,946,546
U.S. Pat. No. 6,881,557
U.S. Patent App. Publn. 2005/0214860
U.S. Patent App. Publn. 2017/0166945
Ausubel et al. (eds.) Current Protocols in Molecular Biology (John Wiley & Sons, New York, 1994).
Barbas et al., *Proc. Natl. Acad. Sci., USA*, 91:3809-13, 1994.
Cloning Vectors: A Laboratory Manual (P. H. Pouwels et al., 1985, Suppl. 1987).
Gram et al., *Proc. Natl. Acad. Sci., USA*, 89:3576-80, 1992.
Hu et al., *Cancer Res.*, 56:3055-61, 1996.
Kyte and Doolittle, *J. Mol. Biol.*, 157(1):105-32, 1982.
Liu et al., *Cell Mol. Biol.*, 49(2):209-16, 2003.
Marks et al., *J. Biol. Chem.*, 267:16007-10 1992.
Schier et al., *J. Mol. Biol.*, 263:551-67, 1996.
Stemmer, *Nature*, 370:389-91, 1994.
Thyer et al., *J. Am. Chem. Soc.*, 137(1):46-49, 2015.

What is claimed is:

1. A nucleic acid molecule encoding a polypeptide comprising an amino acid sequence at least 90% identical to:
   (a) SEQ ID NO:1 and having an amino acid substitution or deletion at a position corresponding to position 344 of SEQ ID NO:1;
   (b) SEQ ID NO:2 and having an amino acid substitution or deletion at a position corresponding to position 702 of SEQ ID NO:2;
   (c) SEQ ID NO:3 and having an amino acid substitution or deletion at a position corresponding to position 655 of SEQ ID NO:3;
   (d) SEQ ID NO:4 and having an amino acid substitution or deletion at a position corresponding to position 73 of SEQ ID NO:4;
   (e) SEQ ID NO:5 and having an amino acid substitution or deletion at a position corresponding to position 781 of SEQ ID NO:5;

(f) SEQ ID NO:6 and having an amino acid substitution or deletion at a position corresponding to position 136 of SEQ ID NO:6;
(g) SEQ ID NO:7 and having an amino acid substitution or deletion at a position corresponding to position 183 of SEQ ID NO:7;
(h) SEQ ID NO:8 and having an amino acid substitution or deletion at a position corresponding to position 1 of SEQ ID NO:8;
(i) SEQ ID NO:9 and having an amino acid substitution or deletion at a position corresponding to position 102 of SEQ ID NO:9;
(j) SEQ ID NO:10 and having an amino acid substitution or deletion at a position corresponding to position 105 of SEQ ID NO:10;
(k) SEQ ID NO:11 and having an amino acid substitution or deletion at a position corresponding to position 673 of SEQ ID NO:11;
(l) SEQ ID NO:12 and having an amino acid substitution or deletion at a position corresponding to position 69 of SEQ ID NO:12;
(m) SEQ ID NO:13 and having an amino acid substitution or deletion at a position corresponding to position 107 of SEQ ID NO:13;
(n) SEQ ID NO:17 and having an amino acid substitution or deletion at a position corresponding to position 246 of SEQ ID NO:17;
(o) SEQ ID NO:18 and having an amino acid substitution or deletion at a position corresponding to position 545 of SEQ ID NO:18; and/or
(p) SEQ ID NO:19 and having an amino acid substitution or deletion at a position corresponding to position 124 of SEQ ID NO:19.

2. A bacterial strain comprising at least one nucleic acid molecule selected from claim 1.

3. The bacterial strain of claim 2, wherein the bacterial strain is an *E. coli* strain.

4. The bacterial strain of claim 2, comprising a nucleic acid that encodes a tRNA that is at least 90% identical to SEQ ID NO: 20 and comprising one or more of the following features:

(i) a G or C at a position corresponding to position 7;
(ii) a T at a position corresponding to position 49;
(iii) a A or C at a position corresponding to position 50;
(iv) a T at a position corresponding to position 64;
(v) a G or A at a position corresponding to position 65; and/or
(vi) a G, T or C at a position corresponding to position 66.

5. The bacterial strain of claim 4, wherein the molecule encodes a tRNA comprising the sequence at least about 90% identical to SEQ ID NO: 20; and comprises one or more of the following features:

(i) a G at a position corresponding to position 7;
(ii) a T at a position corresponding to position 49;
(iii) a C at a position corresponding to position 50;
(iv) a T at a position corresponding to position 64;
(v) a G at a position corresponding to position 65; and/or
(vi) a C at a position corresponding to position 66.

6. The bacterial strain of claim 3, wherein the strain is the *E. coli* bacterial strain deposited at the NCIMB under deposit Accession No. 42595.

7. A culture of bacteria comprising a bacterial strain in accordance with claim 2.

8. The culture of claim 7, said culture comprising an expressed recombinant polypeptide in an amount of 1 to 100 mg/L of the culture, said expressed recombinant polypeptide comprising at least one selenocysteine residue.

9. The culture of claim 8, comprising an expressed recombinant polypeptide in an amount of 10 to 40 mg/L of the culture, said expressed recombinant polypeptide comprising at least one selenocysteine residue.

10. A method of expressing a polypeptide comprising at least one selenocysteine residue comprising:
(a) expressing a nucleic acid encoding the polypeptide in a bacterial strain according to claim 2 and in the presence of selenium source; and
(b) purifying the recombinant polypeptide from the bacteria.

* * * * *

```
SEQUENCE LISTING

<160> NUMBER OF SEQ ID NOS: 31

<210> SEQ ID NO 1
<211> LENGTH: 1049
<212> TYPE: PRT
<213> ORGANISM: Escherichia coli

<400> SEQUENCE: 1

Met Pro Asn Phe Phe Ile Asp Arg Pro Ile Phe Ala Trp Val Ile Ala
1               5                   10                  15

Ile Ile Ile Met Leu Ala Gly Gly Leu Ala Ile Leu Lys Leu Pro Val
            20                  25                  30

Ala Gln Tyr Pro Thr Ile Ala Pro Pro Ala Val Thr Ile Ser Ala Ser
        35                  40                  45

Tyr Pro Gly Ala Asp Ala Lys Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Asn Ser Asp Ser Thr Gly Thr Val Gln Ile Thr Leu Thr Phe Glu Ser
                85                  90                  95

Gly Thr Asp Ala Asp Ile Ala Gln Val Gln Val Gln Asn Lys Leu Gln
            100                 105                 110

Leu Ala Met Pro Leu Leu Pro Gln Glu Val Gln Gln Gln Gly Val Ser
        115                 120                 125

Val Glu Lys Ser Ser Ser Ser Phe Leu Met Val Val Gly Val Ile Asn
    130                 135                 140

Thr Asp Gly Thr Met Thr Gln Glu Asp Ile Ser Asp Tyr Val Ala Ala
```

```
                145                 150                 155                 160
        Asn Met Lys Asp Ala Ile Ser Arg Thr Ser Gly Val Gly Asp Val Gln
                            165                 170                 175
        Leu Phe Gly Ser Gln Tyr Ala Met Arg Ile Trp Met Asn Pro Asn Glu
                        180                 185                 190
        Leu Asn Lys Phe Gln Leu Thr Pro Val Asp Val Ile Thr Ala Ile Lys
                    195                 200                 205
        Ala Gln Asn Ala Gln Val Ala Ala Gly Gln Leu Gly Gly Thr Pro Pro
                210                 215                 220
        Val Lys Gly Gln Gln Leu Asn Ala Ser Ile Ile Ala Gln Thr Arg Leu
        225                 230                 235                 240
        Thr Ser Thr Glu Glu Phe Gly Lys Ile Leu Leu Lys Val Asn Gln Asp
                            245                 250                 255
        Gly Ser Arg Val Leu Leu Arg Asp Val Ala Lys Ile Glu Leu Gly Gly
                        260                 265                 270
        Glu Asn Tyr Asp Ile Ile Ala Glu Phe Asn Gly Gln Pro Ala Ser Gly
                    275                 280                 285
        Leu Gly Ile Lys Leu Ala Thr Gly Ala Asn Ala Leu Asp Thr Ala Ala
                290                 295                 300
        Ala Ile Arg Ala Glu Leu Ala Lys Met Glu Pro Phe Phe Pro Ser Gly
        305                 310                 315                 320
        Leu Lys Ile Val Tyr Pro Tyr Asp Thr Thr Pro Phe Val Lys Ile Ser
                            325                 330                 335
        Ile His Glu Val Val Lys Thr Leu Val Glu Ala Ile Ile Leu Val Phe
                        340                 345                 350
        Leu Val Met Tyr Leu Phe Leu Gln Asn Phe Arg Ala Thr Leu Ile Pro
                    355                 360                 365
        Thr Ile Ala Val Pro Val Val Leu Leu Gly Thr Phe Ala Val Leu Ala
                370                 375                 380
        Ala Phe Gly Phe Ser Ile Asn Thr Leu Thr Met Phe Gly Met Val Leu
        385                 390                 395                 400
        Ala Ile Gly Leu Leu Val Asp Asp Ala Ile Val Val Glu Asn Val
                            405                 410                 415
        Glu Arg Val Met Ala Glu Glu Gly Leu Pro Pro Lys Glu Ala Thr Arg
                        420                 425                 430
        Lys Ser Met Gly Gln Ile Gln Gly Ala Leu Val Gly Ile Ala Met Val
                    435                 440                 445
        Leu Ser Ala Val Phe Val Pro Met Ala Phe Phe Gly Gly Ser Thr Gly
                450                 455                 460
        Ala Ile Tyr Arg Gln Phe Ser Ile Thr Ile Val Ser Ala Met Ala Leu
        465                 470                 475                 480
        Ser Val Leu Val Ala Leu Ile Leu Thr Pro Ala Leu Cys Ala Thr Met
                            485                 490                 495
        Leu Lys Pro Ile Ala Lys Gly Asp His Gly Glu Gly Lys Lys Gly Phe
                        500                 505                 510
        Phe Gly Trp Phe Asn Arg Met Phe Glu Lys Ser Thr His His Tyr Thr
                    515                 520                 525
        Asp Ser Val Gly Gly Ile Leu Arg Ser Thr Gly Arg Tyr Leu Val Leu
                530                 535                 540
        Tyr Leu Ile Ile Val Val Gly Met Ala Tyr Leu Phe Val Arg Leu Pro
        545                 550                 555                 560
        Ser Ser Phe Leu Pro Asp Glu Asp Gln Gly Val Phe Met Thr Met Val
                            565                 570                 575
```

```
Gln Leu Pro Ala Gly Ala Thr Gln Glu Arg Thr Gln Lys Val Leu Asn
            580                 585                 590

Glu Val Thr His Tyr Tyr Leu Thr Lys Glu Lys Asn Asn Val Glu Ser
        595                 600                 605

Val Phe Ala Val Asn Gly Phe Gly Phe Ala Gly Arg Gly Gln Asn Thr
    610                 615                 620

Gly Ile Ala Phe Val Ser Leu Lys Asp Trp Ala Asp Arg Pro Gly Glu
625                 630                 635                 640

Glu Asn Lys Val Glu Ala Ile Thr Met Arg Ala Thr Arg Ala Phe Ser
                645                 650                 655

Gln Ile Lys Asp Ala Met Val Phe Ala Phe Asn Leu Pro Ala Ile Val
            660                 665                 670

Glu Leu Gly Thr Ala Thr Gly Phe Asp Phe Glu Leu Ile Asp Gln Ala
        675                 680                 685

Gly Leu Gly His Glu Lys Leu Thr Gln Ala Arg Asn Gln Leu Leu Ala
    690                 695                 700

Glu Ala Ala Lys His Pro Asp Met Leu Thr Ser Val Arg Pro Asn Gly
705                 710                 715                 720

Leu Glu Asp Thr Pro Gln Phe Lys Ile Asp Ile Asp Gly Glu Lys Ala
                725                 730                 735

Gln Ala Leu Gly Val Ser Ile Asn Asp Ile Asn Thr Thr Leu Gly Ala
            740                 745                 750

Ala Trp Gly Gly Ser Tyr Val Asn Asp Phe Ile Asp Arg Gly Arg Val
        755                 760                 765

Lys Lys Val Tyr Val Met Ser Glu Ala Lys Tyr Arg Met Leu Pro Asp
    770                 775                 780

Asp Ile Gly Asp Trp Tyr Val Arg Ala Ala Asp Gly Gln Met Val Pro
785                 790                 795                 800

Phe Ser Ala Phe Ser Ser Arg Trp Glu Tyr Gly Ser Pro Arg Leu
                805                 810                 815

Glu Arg Tyr Asn Gly Leu Pro Ser Met Glu Ile Leu Gly Gln Ala Ala
            820                 825                 830

Pro Gly Lys Ser Thr Gly Glu Ala Met Glu Leu Met Glu Gln Leu Ala
        835                 840                 845

Ser Lys Leu Pro Thr Gly Val Gly Tyr Asp Trp Thr Gly Met Ser Tyr
    850                 855                 860

Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Val Pro Leu Gly Val Ile Gly Ala
            900                 905                 910

Leu Leu Ala Ala Thr Phe Arg Gly Leu Thr Asn Asp Val Tyr Phe Gln
        915                 920                 925

Val Gly Leu Leu Thr Thr Ile Gly Leu Ser Ala Lys Asn Ala Ile Leu
    930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
            980                 985                 990
```

```
Thr Gly Ala Gly Ser Gly Ala Gln Asn Ala Val Gly Thr Gly Val Met
        995                 1000                1005

Gly Gly Met Val Thr Ala Thr Val Leu Ala Ile Phe Phe Val Pro
    1010                1015                1020

Val Phe Phe Val Val Val Arg Arg Phe Ser Arg Lys Asn Glu
    1025                1030                1035

Asp Ile Glu His Ser His Thr Val Asp His His
    1040                1045

<210> SEQ ID NO 2
<211> LENGTH: 891
<212> TYPE: PRT
<213> ORGANISM: Escherichia coli

<400> SEQUENCE: 2

Met Ala Val Thr Asn Val Ala Glu Leu Asn Ala Leu Val Glu Arg Val
  1               5                  10                  15

Lys Lys Ala Gln Arg Glu Tyr Ala Ser Phe Thr Gln Glu Gln Val Asp
             20                  25                  30

Lys Ile Phe Arg Ala Ala Ala Leu Ala Ala Asp Ala Arg Ile Pro
         35                  40                  45

Leu Ala Lys Met Ala Val Ala Glu Ser Gly Met Gly Ile Val Glu Asp
 50                  55                  60

Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Thr Phe Gly
             85                  90                  95

Thr Ile Thr Ile Ala Glu Pro Ile Gly Ile Ile Cys Gly Ile Val Pro
                100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Asp
        130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320
```

-continued

```
Gly Glu Val Thr Val Asp Glu Ser Glu Pro Phe Ala His Glu Lys
            325                 330                 335
Leu Ser Pro Thr Leu Ala Met Tyr Arg Ala Lys Asp Phe Glu Asp Ala
            340                 345                 350
Val Glu Lys Ala Glu Lys Leu Val Ala Met Gly Gly Ile Gly His Thr
            355                 360                 365
Ser Cys Leu Tyr Thr Asp Gln Asp Asn Gln Pro Ala Arg Val Ser Tyr
            370                 375                 380
Phe Gly Gln Lys Met Lys Thr Ala Arg Ile Leu Ile Asn Thr Pro Ala
385                 390                 395                 400
Ser Gln Gly Gly Ile Gly Asp Leu Tyr Asn Phe Lys Leu Ala Pro Ser
                    405                 410                 415
Leu Thr Leu Gly Cys Gly Ser Trp Gly Gly Asn Ser Ile Ser Glu Asn
                    420                 425                 430
Val Gly Pro Lys His Leu Ile Asn Lys Lys Thr Val Ala Lys Arg Ala
                    435                 440                 445
Glu Asn Met Leu Trp His Lys Leu Pro Lys Ser Ile Tyr Phe Arg Arg
            450                 455                 460
Gly Ser Leu Pro Ile Ala Leu Asp Glu Val Ile Thr Asp Gly His Lys
465                 470                 475                 480
Arg Ala Leu Ile Val Thr Asp Arg Phe Leu Phe Asn Asn Gly Tyr Ala
                    485                 490                 495
Asp Gln Ile Thr Ser Val Leu Lys Ala Ala Gly Val Glu Thr Glu Val
                    500                 505                 510
Phe Phe Glu Val Glu Ala Asp Pro Thr Leu Ser Ile Val Arg Lys Gly
                    515                 520                 525
Ala Glu Leu Ala Asn Ser Phe Lys Pro Asp Val Ile Ile Ala Leu Gly
            530                 535                 540
Gly Gly Ser Pro Met Asp Ala Ala Lys Ile Met Trp Val Met Tyr Glu
545                 550                 555                 560
His Pro Glu Thr His Phe Glu Glu Leu Ala Leu Arg Phe Met Asp Ile
                    565                 570                 575
Arg Lys Arg Ile Tyr Lys Phe Pro Lys Met Gly Val Lys Ala Lys Met
                    580                 585                 590
Ile Ala Val Thr Thr Thr Ser Gly Thr Gly Ser Glu Val Thr Pro Phe
                    595                 600                 605
Ala Val Val Thr Asp Asp Ala Thr Gly Gln Lys Tyr Pro Leu Ala Asp
            610                 615                 620
Tyr Ala Leu Thr Pro Asp Met Ala Ile Val Asp Ala Asn Leu Val Met
625                 630                 635                 640
Asp Met Pro Lys Ser Leu Cys Ala Phe Gly Gly Leu Asp Ala Val Thr
                    645                 650                 655
His Ala Met Glu Ala Tyr Val Ser Val Leu Ala Ser Glu Phe Ser Asp
                    660                 665                 670
Gly Gln Ala Leu Gln Ala Leu Lys Leu Leu Lys Glu Tyr Leu Pro Ala
                    675                 680                 685
Ser Tyr His Glu Gly Ser Lys Asn Pro Val Ala Arg Glu Arg Val His
            690                 695                 700
Ser Ala Ala Thr Ile Ala Gly Ile Ala Phe Ala Asn Ala Phe Leu Gly
705                 710                 715                 720
Val Cys His Ser Met Ala His Lys Leu Gly Ser Gln Phe His Ile Pro
                    725                 730                 735
```

-continued

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
                755                 760                 765

Pro Gln Ala Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 3
<211> LENGTH: 778
<212> TYPE: PRT
<213> ORGANISM: Escherichia coli

<400> SEQUENCE: 3

Met Lys Gln Ile Arg Leu Leu Ala Gln Tyr Tyr Val Asp Leu Met Met
1               5                   10                  15

Lys Leu Gly Leu Val Arg Phe Ser Met Leu Leu Ala Leu Ala Leu Val
                20                  25                  30

Val Leu Ala Ile Val Val Gln Met Ala Val Thr Met Val Leu His Gly
            35                  40                  45

Gln Val Glu Ser Ile Asp Val Ile Arg Ser Ile Phe Phe Gly Leu Leu
        50                  55                  60

Ile Thr Pro Trp Ala Val Tyr Phe Leu Ser Val Val Glu Gln Leu
65                  70                  75                  80

Glu Glu Ser Arg Gln Arg Leu Ser Arg Leu Val Gln Lys Leu Glu Glu
                85                  90                  95

Met Arg Glu Arg Asp Leu Ser Leu Asn Val Gln Leu Lys Asp Asn Ile
                100                 105                 110

Ala Gln Leu Asn Gln Glu Ile Ala Val Arg Glu Lys Ala Glu Ala Glu
            115                 120                 125

Leu Gln Glu Thr Phe Gly Gln Leu Lys Ile Glu Ile Lys Glu Arg Glu
        130                 135                 140

Glu Thr Gln Ile Gln Leu Glu Gln Gln Ser Ser Phe Leu Arg Ser Phe
145                 150                 155                 160

Leu Asp Ala Ser Pro Asp Leu Val Phe Tyr Arg Asn Glu Asp Lys Glu
                165                 170                 175

Phe Ser Gly Cys Asn Arg Ala Met Glu Leu Leu Thr Gly Lys Ser Glu
                180                 185                 190

Lys Gln Leu Val His Leu Lys Pro Ala Asp Val Tyr Ser Pro Glu Ala
            195                 200                 205

Ala Ala Lys Val Ile Glu Thr Asp Glu Lys Val Phe Arg His Asn Val
        210                 215                 220

```
Ser Leu Thr Tyr Glu Gln Trp Leu Asp Tyr Pro Asp Gly Arg Lys Ala
225                 230                 235                 240

Cys Phe Glu Ile Arg Lys Val Pro Tyr Tyr Asp Arg Val Gly Lys Arg
                245                 250                 255

His Gly Leu Met Gly Phe Gly Arg Asp Ile Thr Glu Arg Lys Arg Tyr
            260                 265                 270

Gln Asp Ala Leu Glu Arg Ala Ser Arg Asp Lys Thr Thr Phe Ile Ser
        275                 280                 285

Thr Ile Ser His Glu Leu Arg Thr Pro Leu Asn Gly Ile Val Gly Leu
290                 295                 300

Ser Arg Ile Leu Leu Asp Thr Glu Leu Thr Ala Glu Gln Glu Lys Tyr
305                 310                 315                 320

Leu Lys Thr Ile His Val Ser Ala Val Thr Leu Gly Asn Ile Phe Asn
                325                 330                 335

Asp Ile Ile Asp Met Asp Lys Met Glu Arg Arg Lys Val Gln Leu Asp
            340                 345                 350

Asn Gln Pro Val Asp Phe Thr Ser Phe Leu Ala Asp Leu Glu Asn Leu
        355                 360                 365

Ser Ala Leu Gln Ala Gln Gln Lys Gly Leu Arg Phe Asn Leu Glu Pro
370                 375                 380

Thr Leu Pro Leu Pro His Gln Val Ile Thr Asp Gly Thr Arg Leu Arg
385                 390                 395                 400

Gln Ile Leu Trp Asn Leu Ile Ser Asn Ala Val Lys Phe Thr Gln Gln
                405                 410                 415

Gly Gln Val Thr Val Arg Val Arg Tyr Asp Glu Gly Asp Met Leu His
            420                 425                 430

Phe Glu Val Glu Asp Ser Gly Ile Gly Ile Pro Gln Asp Glu Leu Asp
        435                 440                 445

Lys Ile Phe Ala Met Tyr Tyr Gln Val Lys Asp Ser His Gly Gly Lys
450                 455                 460

Pro Ala Thr Gly Thr Gly Ile Gly Leu Ala Val Ser Arg Arg Leu Ala
465                 470                 475                 480

Lys Asn Met Gly Gly Asp Ile Thr Val Thr Ser Glu Gln Gly Lys Gly
                485                 490                 495

Ser Thr Phe Thr Leu Thr Ile His Ala Pro Ser Val Ala Glu Glu Val
            500                 505                 510

Asp Asp Ala Phe Asp Glu Asp Met Pro Leu Pro Ala Leu Asn Val
        515                 520                 525

Leu Leu Val Glu Asp Ile Glu Leu Asn Val Ile Val Ala Arg Ser Val
530                 535                 540

Leu Glu Lys Leu Gly Asn Ser Val Asp Val Ala Met Thr Gly Lys Ala
545                 550                 555                 560

Ala Leu Glu Met Phe Lys Pro Gly Tyr Asp Leu Val Leu Leu Asp
                565                 570                 575

Ile Gln Leu Pro Asp Met Thr Gly Leu Asp Ile Ser Arg Glu Leu Thr
            580                 585                 590

Lys Arg Tyr Pro Arg Glu Asp Leu Pro Pro Leu Val Ala Leu Thr Ala
        595                 600                 605

Asn Val Leu Lys Asp Lys Gln Glu Tyr Leu Asn Ala Gly Met Asp Asp
610                 615                 620

Val Leu Ser Lys Pro Leu Ser Val Pro Ala Leu Thr Ala Met Ile Lys
625                 630                 635                 640
```

```
Lys Phe Trp Asp Thr Gln Asp Glu Glu Ser Thr Val Thr Thr Glu
            645                 650                 655

Glu Asn Ser Lys Ser Glu Ala Leu Leu Asp Ile Pro Met Leu Glu Gln
        660                 665                 670

Tyr Leu Glu Leu Val Gly Pro Lys Leu Ile Thr Asp Gly Leu Ala Val
        675                 680                 685

Phe Glu Lys Met Met Pro Gly Tyr Val Ser Val Leu Glu Ser Asn Leu
    690                 695                 700

Thr Ala Gln Asp Lys Lys Gly Ile Val Glu Gly His Lys Ile Lys
705                 710                 715                 720

Gly Ala Ala Gly Ser Val Gly Leu Arg His Leu Gln Gln Leu Gly Gln
                725                 730                 735

Gln Ile Gln Ser Pro Asp Leu Pro Ala Trp Glu Asp Asn Val Gly Glu
            740                 745                 750

Trp Ile Glu Glu Met Lys Glu Glu Trp Arg His Asp Val Glu Val Leu
        755                 760                 765

Lys Ala Trp Val Ala Lys Ala Thr Lys Lys
        770                 775

<210> SEQ ID NO 4
<211> LENGTH: 323
<212> TYPE: PRT
<213> ORGANISM: Escherichia coli

<400> SEQUENCE: 4

Met Ser Lys Ile Phe Glu Asp Asn Ser Leu Thr Ile Gly His Thr Pro
1               5                   10                  15

Leu Val Arg Leu Asn Arg Ile Gly Asn Gly Arg Ile Leu Ala Lys Val
            20                  25                  30

Glu Ser Arg Asn Pro Ser Phe Ser Val Lys Cys Arg Ile Gly Ala Asn
        35                  40                  45

Met Ile Trp Asp Ala Glu Lys Arg Gly Val Leu Lys Pro Gly Val Glu
    50                  55                  60

Leu Val Glu Pro Thr Ser Gly Asn Thr Gly Ile Ala Leu Ala Tyr Val
65                  70                  75                  80

Ala Ala Ala Arg Gly Tyr Lys Leu Thr Leu Thr Met Pro Glu Thr Met
                85                  90                  95

Ser Ile Glu Arg Arg Lys Leu Leu Lys Ala Leu Gly Ala Asn Leu Val
            100                 105                 110

Leu Thr Glu Gly Ala Lys Gly Met Lys Gly Ala Ile Gln Lys Ala Glu
        115                 120                 125

Glu Ile Val Ala Ser Asn Pro Glu Lys Tyr Leu Leu Leu Gln Gln Phe
    130                 135                 140

Ser Asn Pro Ala Asn Pro Glu Ile His Glu Lys Thr Thr Gly Pro Glu
145                 150                 155                 160

Ile Trp Glu Asp Thr Asp Gly Gln Val Asp Val Phe Ile Ala Gly Val
                165                 170                 175

Gly Thr Gly Gly Thr Leu Thr Gly Val Ser Arg Tyr Ile Lys Gly Thr
            180                 185                 190

Lys Gly Lys Thr Asp Leu Ile Ser Val Ala Val Glu Pro Thr Asp Ser
        195                 200                 205

Pro Val Ile Ala Gln Ala Leu Ala Gly Glu Glu Ile Lys Pro Gly Pro
    210                 215                 220

His Lys Ile Gln Gly Ile Gly Ala Gly Phe Ile Pro Ala Asn Leu Asp
225                 230                 235                 240
```

```
Leu Lys Leu Val Asp Lys Val Ile Gly Ile Thr Asn Glu Glu Ala Ile
                245                 250                 255

Ser Thr Ala Arg Arg Leu Met Glu Glu Gly Ile Leu Ala Gly Ile
            260                 265                 270

Ser Ser Gly Ala Ala Val Ala Ala Leu Lys Leu Gln Glu Asp Glu
        275                 280                 285

Ser Phe Thr Asn Lys Asn Ile Val Val Ile Leu Pro Ser Ser Gly Glu
    290                 295                 300

Arg Tyr Leu Ser Thr Ala Leu Phe Ala Asp Leu Phe Thr Glu Lys Glu
305                 310                 315                 320

Leu Gln Gln

<210> SEQ ID NO 5
<211> LENGTH: 1160
<212> TYPE: PRT
<213> ORGANISM: Escherichia coli

<400> SEQUENCE: 5

Met Ser Glu Pro Arg Phe Val His Leu Arg Val His Ser Asp Tyr Ser
1               5                   10                  15

Met Ile Asp Gly Leu Ala Lys Thr Ala Pro Leu Val Lys Lys Ala Ala
            20                  25                  30

Ala Leu Gly Met Pro Ala Leu Ala Ile Thr Asp Phe Thr Asn Leu Cys
        35                  40                  45

Gly Leu Val Lys Phe Tyr Gly Ala Gly His Gly Ala Gly Ile Lys Pro
    50                  55                  60

Ile Val Gly Ala Asp Phe Asn Val Gln Cys Asp Leu Leu Gly Asp Glu
65                  70                  75                  80

Leu Thr His Leu Thr Val Leu Ala Ala Asn Asn Thr Gly Tyr Gln Asn
                85                  90                  95

Leu Thr Leu Leu Ile Ser Lys Ala Tyr Gln Arg Gly Tyr Gly Ala Ala
            100                 105                 110

Gly Pro Ile Ile Asp Arg Asp Trp Leu Ile Glu Leu Asn Glu Gly Leu
        115                 120                 125

Ile Leu Leu Ser Gly Gly Arg Met Gly Asp Val Gly Arg Ser Leu Leu
    130                 135                 140

Arg Gly Asn Ser Ala Leu Val Asp Glu Cys Val Ala Phe Tyr Glu Glu
145                 150                 155                 160

His Phe Pro Asp Arg Tyr Phe Leu Glu Leu Ile Arg Thr Gly Arg Pro
                165                 170                 175

Asp Glu Glu Ser Tyr Leu His Ala Ala Val Glu Leu Ala Glu Ala Arg
            180                 185                 190

Gly Leu Pro Val Val Ala Thr Asn Asp Val Arg Phe Ile Asp Ser Ser
        195                 200                 205

Asp Phe Asp Ala His Glu Ile Arg Val Ala Ile His Asp Gly Phe Thr
    210                 215                 220

Leu Asp Asp Pro Lys Arg Pro Arg Asn Tyr Ser Pro Gln Gln Tyr Met
225                 230                 235                 240

Arg Ser Glu Glu Glu Met Cys Glu Leu Phe Ala Asp Ile Pro Glu Ala
                245                 250                 255

Leu Ala Asn Thr Val Glu Ile Ala Lys Arg Cys Asn Val Thr Val Arg
            260                 265                 270

Leu Gly Glu Tyr Phe Leu Pro Gln Phe Pro Thr Gly Asp Met Ser Thr
        275                 280                 285
```

-continued

```
Glu Asp Tyr Leu Val Lys Arg Ala Lys Glu Gly Leu Glu Glu Arg Leu
    290                 295                 300

Ala Phe Leu Phe Pro Asp Glu Glu Arg Leu Lys Arg Arg Pro Glu
305                 310                 315                 320

Tyr Asp Glu Arg Leu Glu Thr Glu Leu Gln Val Ile Asn Gln Met Gly
                325                 330                 335

Phe Pro Gly Tyr Phe Leu Ile Val Met Glu Phe Ile Gln Trp Ser Lys
                340                 345                 350

Asp Asn Gly Val Pro Val Gly Pro Arg Gly Ser Gly Ala Gly Ser
            355                 360                 365

Leu Val Ala Tyr Ala Leu Lys Ile Thr Asp Leu Asp Pro Leu Glu Phe
    370                 375                 380

Asp Leu Leu Phe Glu Arg Phe Leu Asn Pro Glu Arg Val Ser Met Pro
385                 390                 395                 400

Asp Phe Asp Val Asp Phe Cys Met Glu Lys Arg Asp Gln Val Ile Glu
                405                 410                 415

His Val Ala Asp Met Tyr Gly Arg Asp Ala Val Ser Gln Ile Ile Thr
            420                 425                 430

Phe Gly Thr Met Ala Ala Lys Ala Val Ile Arg Asp Val Gly Arg Val
    435                 440                 445

Leu Gly His Pro Tyr Gly Phe Val Asp Arg Ile Ser Lys Leu Ile Pro
    450                 455                 460

Pro Asp Pro Gly Met Thr Leu Ala Lys Ala Phe Glu Ala Glu Pro Gln
465                 470                 475                 480

Leu Pro Glu Ile Tyr Glu Ala Asp Glu Val Lys Ala Leu Ile Asp
                485                 490                 495

Met Ala Arg Lys Leu Glu Gly Val Thr Arg Asn Ala Gly Lys His Ala
            500                 505                 510

Gly Gly Val Val Ile Ala Pro Thr Lys Ile Thr Asp Phe Ala Pro Leu
    515                 520                 525

Tyr Cys Asp Glu Glu Gly Lys His Pro Val Thr Gln Phe Asp Lys Ser
    530                 535                 540

Asp Val Glu Tyr Ala Gly Leu Val Lys Phe Asp Phe Leu Gly Leu Arg
545                 550                 555                 560

Thr Leu Thr Ile Ile Asn Trp Ala Leu Glu Met Ile Asn Lys Arg Arg
                565                 570                 575

Ala Lys Asn Gly Glu Pro Pro Leu Asp Ile Ala Ile Pro Leu Asp
            580                 585                 590

Asp Lys Lys Ser Phe Asp Met Leu Gln Arg Ser Glu Thr Ala Val
    595                 600                 605

Phe Gln Leu Glu Ser Arg Gly Met Lys Asp Leu Ile Lys Arg Leu Gln
    610                 615                 620

Pro Asp Cys Phe Glu Asp Met Ile Ala Leu Val Ala Leu Phe Arg Pro
625                 630                 635                 640

Gly Pro Leu Gln Ser Gly Met Val Asp Asn Phe Ile Asp Arg Lys His
                645                 650                 655

Gly Arg Glu Glu Ile Ser Tyr Pro Asp Val Gln Trp Gln His Glu Ser
            660                 665                 670

Leu Lys Pro Val Leu Glu Pro Thr Tyr Gly Ile Ile Leu Tyr Gln Glu
    675                 680                 685

Gln Val Met Gln Ile Ala Gln Val Leu Ser Gly Tyr Thr Leu Gly Gly
    690                 695                 700
```

```
Ala Asp Met Leu Arg Arg Ala Met Gly Lys Lys Pro Glu Glu Met
705                 710                 715                 720

Ala Lys Gln Arg Ser Val Phe Ala Glu Gly Ala Glu Lys Asn Gly Ile
            725                 730                 735

Asn Ala Glu Leu Ala Met Lys Ile Phe Asp Leu Val Glu Lys Phe Ala
                740                 745                 750

Gly Tyr Gly Phe Asn Lys Ser His Ser Ala Ala Tyr Ala Leu Val Ser
            755                 760                 765

Tyr Gln Thr Leu Trp Leu Lys Ala His Tyr Pro Ala Glu Phe Met Ala
    770                 775                 780

Ala Val Met Thr Ala Asp Met Asp Asn Thr Glu Lys Val Val Gly Leu
785                 790                 795                 800

Val Asp Glu Cys Trp Arg Met Gly Leu Lys Ile Leu Pro Pro Asp Ile
                805                 810                 815

Asn Ser Gly Leu Tyr His Phe His Val Asn Asp Asp Gly Glu Ile Val
                820                 825                 830

Tyr Gly Ile Gly Ala Ile Lys Gly Val Gly Glu Gly Pro Ile Glu Ala
                835                 840                 845

Ile Ile Glu Ala Arg Asn Lys Gly Gly Tyr Phe Arg Glu Leu Phe Asp
850                 855                 860

Leu Cys Ala Arg Thr Asp Thr Lys Lys Leu Asn Arg Arg Val Leu Glu
865                 870                 875                 880

Lys Leu Ile Met Ser Gly Ala Phe Asp Arg Leu Gly Pro His Arg Ala
                885                 890                 895

Ala Leu Met Asn Ser Leu Gly Asp Ala Leu Lys Ala Ala Asp Gln His
                900                 905                 910

Ala Lys Ala Glu Ala Ile Gly Gln Ala Asp Met Phe Gly Val Leu Ala
                915                 920                 925

Glu Glu Pro Glu Gln Ile Gln Ser Tyr Ala Ser Cys Gln Pro Trp
930                 935                 940

Pro Glu Gln Val Val Leu Asp Gly Glu Arg Glu Thr Leu Gly Leu Tyr
945                 950                 955                 960

Leu Thr Gly His Pro Ile Asn Gln Tyr Leu Lys Glu Ile Glu Arg Tyr
                965                 970                 975

Val Gly Gly Val Arg Leu Lys Asp Met His Pro Thr Glu Arg Gly Lys
            980                 985                 990

Val Ile Thr Ala Ala Gly Leu Val Val Ala Ala Arg Val Met Val Thr
            995                1000                1005

Lys Arg Gly Asn Arg Ile Gly Ile Cys Thr Leu Asp Asp Arg Ser
    1010                1015                1020

Gly Arg Leu Glu Val Met Leu Phe Thr Asp Ala Leu Asp Lys Tyr
    1025                1030                1035

Gln Gln Leu Leu Glu Lys Asp Arg Ile Leu Ile Val Ser Gly Gln
    1040                1045                1050

Val Ser Phe Asp Asp Phe Ser Gly Gly Leu Lys Met Thr Ala Arg
    1055                1060                1065

Glu Val Met Asp Ile Asp Glu Ala Arg Glu Lys Tyr Ala Arg Gly
    1070                1075                1080

Leu Ala Ile Ser Leu Thr Asp Arg Gln Ile Asp Asp Gln Leu Leu
    1085                1090                1095

Asn Arg Leu Arg Gln Ser Leu Glu Pro His Arg Ser Gly Thr Ile
    1100                1105                1110

Pro Val His Leu Tyr Tyr Gln Arg Ala Asp Ala Arg Ala Arg Leu
```

-continued

```
              1115                1120                1125

Arg Phe Gly Ala Thr Trp Arg Val Ser Pro Ser Asp Arg Leu Leu
        1130                1135                1140

Asn Asp Leu Arg Gly Leu Ile Gly Ser Glu Gln Val Glu Leu Glu
    1145                1150                1155

Phe Asp
    1160

<210> SEQ ID NO 6
<211> LENGTH: 420
<212> TYPE: PRT
<213> ORGANISM: Escherichia coli

<400> SEQUENCE: 6

Met Ile Lys Ala Thr Asp Arg Lys Leu Val Val Gly Leu Glu Ile Gly
 1               5                  10                  15

Thr Ala Lys Val Ala Ala Leu Val Gly Glu Val Leu Pro Asp Gly Met
            20                  25                  30

Val Asn Ile Ile Gly Val Gly Ser Cys Pro Ser Arg Gly Met Asp Lys
        35                  40                  45

Gly Gly Val Asn Asp Leu Glu Ser Val Val Lys Cys Val Gln Arg Ala
    50                  55                  60

Ile Asp Gln Ala Glu Leu Met Ala Asp Cys Gln Ile Ser Ser Val Tyr
65                  70                  75                  80

Leu Ala Leu Ser Gly Lys His Ile Ser Cys Gln Asn Glu Ile Gly Met
                85                  90                  95

Val Pro Ile Ser Glu Glu Val Thr Gln Glu Asp Val Glu Asn Val
            100                 105                 110

Val His Thr Ala Lys Ser Val Arg Val Arg Asp Glu His Arg Val Leu
        115                 120                 125

His Val Ile Pro Gln Glu Tyr Ala Ile Asp Tyr Gln Glu Gly Ile Lys
    130                 135                 140

Asn Pro Val Gly Leu Ser Gly Val Arg Met Gln Ala Lys Val His Leu
145                 150                 155                 160

Ile Thr Cys His Asn Asp Met Ala Lys Asn Ile Val Lys Ala Val Glu
                165                 170                 175

Arg Cys Gly Leu Lys Val Asp Gln Leu Ile Phe Ala Gly Leu Ala Ser
            180                 185                 190

Ser Tyr Ser Val Leu Thr Glu Asp Glu Arg Glu Leu Gly Val Cys Val
        195                 200                 205

Val Asp Ile Gly Gly Gly Thr Met Asp Ile Ala Val Tyr Thr Gly Gly
    210                 215                 220

Ala Leu Arg His Thr Lys Val Ile Pro Tyr Ala Gly Asn Val Val Thr
225                 230                 235                 240

Ser Asp Ile Ala Tyr Ala Phe Gly Thr Pro Pro Ser Asp Ala Glu Ala
                245                 250                 255

Ile Lys Val Arg His Gly Cys Ala Leu Gly Ser Ile Val Gly Lys Asp
            260                 265                 270

Glu Ser Val Glu Val Pro Ser Val Gly Gly Arg Pro Pro Arg Ser Leu
        275                 280                 285

Gln Arg Gln Thr Leu Ala Glu Val Ile Glu Pro Arg Tyr Thr Glu Leu
    290                 295                 300

Leu Asn Leu Val Asn Glu Glu Ile Leu Gln Leu Gln Glu Lys Leu Arg
305                 310                 315                 320
```

```
Gln Gln Gly Val Lys His His Leu Ala Ala Gly Ile Val Leu Thr Gly
                325                 330                 335

Gly Ala Ala Gln Ile Glu Gly Leu Ala Ala Cys Ala Gln Arg Val Phe
            340                 345                 350

His Thr Gln Val Arg Ile Gly Ala Pro Leu Asn Ile Thr Gly Leu Thr
        355                 360                 365

Asp Tyr Ala Gln Glu Pro Tyr Tyr Ser Thr Ala Val Gly Leu Leu His
    370                 375                 380

Tyr Gly Lys Glu Ser His Leu Asn Gly Glu Ala Glu Val Glu Lys Arg
385                 390                 395                 400

Val Thr Ala Ser Val Gly Ser Trp Ile Lys Arg Leu Asn Ser Trp Leu
                405                 410                 415

Arg Lys Glu Phe
            420

<210> SEQ ID NO 7
<211> LENGTH: 418
<212> TYPE: PRT
<213> ORGANISM: Escherichia coli

<400> SEQUENCE: 7

Met Thr Leu Leu Ala Leu Gly Ile Asn His Lys Thr Ala Pro Val Ser
1               5                   10                  15

Leu Arg Glu Arg Val Ser Phe Ser Pro Asp Lys Leu Asp Gln Ala Leu
                20                  25                  30

Asp Ser Leu Leu Ala Gln Pro Met Val Gln Gly Gly Val Val Leu Ser
            35                  40                  45

Thr Cys Asn Arg Thr Glu Leu Tyr Leu Ser Val Glu Glu Gln Asp Asn
50                  55                  60

Leu Gln Glu Ala Leu Ile Arg Trp Leu Cys Asp Tyr His Asn Leu Asn
65                  70                  75                  80

Glu Glu Asp Leu Arg Lys Ser Leu Tyr Trp His Gln Asp Asn Asp Ala
                85                  90                  95

Val Ser His Leu Met Arg Val Ala Ser Gly Leu Asp Ser Leu Val Leu
                100                 105                 110

Gly Glu Pro Gln Ile Leu Gly Gln Val Lys Lys Ala Phe Ala Asp Ser
            115                 120                 125

Gln Lys Gly His Met Lys Ala Ser Glu Leu Glu Arg Met Phe Gln Lys
        130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
                165                 170                 175

Phe Glu Ser Leu Ser Thr Val Thr Val Leu Leu Val Gly Ala Gly Glu
            180                 185                 190

Thr Ile Glu Leu Val Ala Arg His Leu Arg Glu His Lys Val Gln Lys
        195                 200                 205

Met Ile Ile Ala Asn Arg Thr Arg Glu Arg Ala Gln Ile Leu Ala Asp
    210                 215                 220

Glu Val Gly Ala Glu Val Ile Ala Leu Ser Asp Ile Asp Glu Arg Leu
225                 230                 235                 240

Arg Glu Ala Asp Ile Ile Ile Ser Ser Thr Ala Ser Pro Leu Pro Ile
                245                 250                 255

Ile Gly Lys Gly Met Val Glu Arg Ala Leu Lys Ser Arg Arg Asn Gln
            260                 265                 270
```

```
Pro Met Leu Leu Val Asp Ile Ala Val Pro Arg Asp Val Glu Pro Glu
        275                 280                 285

Val Gly Lys Leu Ala Asn Ala Tyr Leu Tyr Ser Val Asp Asp Leu Gln
        290                 295                 300

Ser Ile Ile Ser His Asn Leu Ala Gln Arg Lys Ala Ala Val Glu
305                 310                 315                 320

Ala Glu Thr Ile Val Ala Gln Glu Thr Ser Glu Phe Met Ala Trp Leu
                325                 330                 335

Arg Ala Gln Ser Ala Ser Glu Thr Ile Arg Glu Tyr Arg Ser Gln Ala
            340                 345                 350

Glu Gln Val Arg Asp Glu Leu Thr Ala Lys Ala Leu Ala Leu Glu
        355                 360                 365

Gln Gly Gly Asp Ala Gln Ala Ile Met Gln Asp Leu Ala Trp Lys Leu
        370                 375                 380

Thr Asn Arg Leu Ile His Ala Pro Thr Lys Ser Leu Gln Gln Ala Ala
385                 390                 395                 400

Arg Asp Gly Asp Asn Glu Arg Leu Asn Ile Leu Arg Asp Ser Leu Gly
                405                 410                 415

Leu Glu

<210> SEQ ID NO 8
<211> LENGTH: 410
<212> TYPE: PRT
<213> ORGANISM: Escherichia coli

<400> SEQUENCE: 8

Met Gln Asn Lys Leu Ala Ser Gly Ala Arg Leu Gly Arg Gln Ala Leu
1               5                   10                  15

Leu Phe Pro Leu Cys Leu Val Leu Tyr Glu Phe Ser Thr Tyr Ile Gly
            20                  25                  30

Asn Asp Met Ile Gln Pro Gly Met Leu Ala Val Val Glu Gln Tyr Gln
        35                  40                  45

Ala Gly Ile Asp Trp Val Pro Thr Ser Met Thr Ala Tyr Leu Ala Gly
    50                  55                  60

Gly Met Phe Leu Gln Trp Leu Leu Gly Pro Leu Ser Asp Arg Ile Gly
65                  70                  75                  80

Arg Arg Pro Val Met Leu Ala Gly Val Val Trp Phe Ile Val Thr Cys
                85                  90                  95

Leu Ala Ile Leu Leu Ala Gln Asn Ile Glu Gln Phe Thr Leu Leu Arg
            100                 105                 110

Phe Leu Gln Gly Ile Ser Leu Cys Phe Ile Gly Ala Val Gly Tyr Ala
        115                 120                 125

Ala Ile Gln Glu Ser Phe Glu Glu Ala Val Cys Ile Lys Ile Thr Ala
    130                 135                 140

Leu Met Ala Asn Val Ala Leu Ile Ala Pro Leu Leu Gly Pro Leu Val
145                 150                 155                 160

Gly Ala Ala Trp Ile His Val Leu Pro Trp Glu Gly Met Phe Val Leu
                165                 170                 175

Phe Ala Ala Leu Ala Ala Ile Ser Phe Phe Gly Leu Gln Arg Ala Met
            180                 185                 190

Pro Glu Thr Ala Thr Arg Ile Gly Glu Lys Leu Ser Leu Lys Glu Leu
        195                 200                 205

Gly Arg Asp Tyr Lys Leu Val Leu Lys Asn Gly Arg Phe Val Ala Gly
    210                 215                 220
```

```
Ala Leu Ala Leu Gly Phe Val Ser Leu Pro Leu Leu Ala Trp Ile Ala
225                 230                 235                 240

Gln Ser Pro Ile Ile Ile Thr Gly Glu Gln Leu Ser Ser Tyr Glu
                245                 250                 255

Tyr Gly Leu Leu Gln Val Pro Ile Phe Gly Ala Leu Ile Ala Gly Asn
                260                 265                 270

Leu Leu Leu Ala Arg Leu Thr Ser Arg Arg Thr Val Arg Ser Leu Ile
                275                 280                 285

Ile Met Gly Gly Trp Pro Ile Met Ile Gly Leu Leu Val Ala Ala Ala
                290                 295                 300

Ala Thr Val Ile Ser Ser His Ala Tyr Leu Trp Met Thr Ala Gly Leu
305                 310                 315                 320

Ser Ile Tyr Ala Phe Gly Ile Gly Leu Ala Asn Ala Gly Leu Val Arg
                325                 330                 335

Leu Thr Leu Phe Ala Ser Asp Met Ser Lys Gly Thr Val Ser Ala Ala
                340                 345                 350

Met Gly Met Leu Gln Met Leu Ile Phe Thr Val Gly Ile Glu Ile Ser
                355                 360                 365

Lys His Ala Trp Leu Asn Gly Gly Asn Gly Leu Phe Asn Leu Phe Asn
370                 375                 380

Leu Val Asn Gly Ile Leu Trp Leu Ser Leu Met Val Ile Phe Leu Lys
385                 390                 395                 400

Asp Lys Gln Met Gly Asn Ser His Glu Gly
                405                 410

<210> SEQ ID NO 9
<211> LENGTH: 239
<212> TYPE: PRT
<213> ORGANISM: Escherichia coli

<400> SEQUENCE: 9

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
                20                  25                  30

Ser Val Ala Asn Ala Glu Gln Met Asp Arg Leu Leu Thr Arg Glu Ser
                35                  40                  45

Phe His Leu Met Val Leu Asp Leu Met Leu Pro Gly Glu Asp Gly Leu
        50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
                100                 105                 110

Leu Ala Arg Ile Arg Ala Val Leu Arg Arg Gln Ala Asn Glu Leu Pro
                115                 120                 125

Gly Ala Pro Ser Gln Glu Glu Ala Val Ile Ala Phe Gly Lys Phe Lys
                130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
                165                 170                 175

Arg Glu Pro Leu Ser Arg Asp Lys Leu Met Asn Leu Ala Arg Gly Arg
```

```
            180                 185                 190
Glu Tyr Ser Ala Met Glu Arg Ser Ile Asp Val Gln Ile Ser Arg Leu
        195                 200                 205

Arg Arg Met Val Glu Glu Asp Pro Ala His Pro Arg Tyr Ile Gln Thr
    210                 215                 220

Val Trp Gly Leu Gly Tyr Val Phe Val Pro Asp Gly Ser Lys Ala
225                 230                 235

<210> SEQ ID NO 10
<211> LENGTH: 465
<212> TYPE: PRT
<213> ORGANISM: Escherichia coli

<400> SEQUENCE: 10

Met Phe Thr Arg Val Ala Asn Phe Cys Arg Lys Val Leu Ser Arg Glu
1               5                   10                  15

Glu Ser Glu Ala Glu Gln Ala Val Ala Arg Pro Gln Val Thr Val Ile
            20                  25                  30

Pro Arg Glu Gln His Ala Ile Ser Arg Lys Asp Ile Ser Glu Asn Ala
        35                  40                  45

Leu Lys Val Met Tyr Arg Leu Asn Lys Ala Gly Tyr Glu Ala Trp Leu
    50                  55                  60

Val Gly Gly Gly Val Arg Asp Leu Leu Leu Gly Lys Lys Pro Lys Asp
65                  70                  75                  80

Phe Asp Val Thr Thr Asn Ala Thr Pro Glu Gln Val Arg Lys Leu Phe
                85                  90                  95

Arg Asn Cys Arg Leu Val Gly Arg Arg Phe Arg Leu Ala His Val Met
            100                 105                 110

Phe Gly Pro Glu Ile Ile Glu Val Ala Thr Phe Arg Gly His His Glu
        115                 120                 125

Gly Asn Val Ser Asp Arg Thr Thr Ser Gln Arg Gly Gln Asn Gly Met
    130                 135                 140

Leu Leu Arg Asp Asn Ile Phe Gly Ser Ile Glu Glu Asp Ala Gln Arg
145                 150                 155                 160

Arg Asp Phe Thr Ile Asn Ser Leu Tyr Tyr Ser Val Ala Asp Phe Thr
                165                 170                 175

Val Arg Asp Tyr Val Gly Gly Met Lys Asp Leu Lys Asp Gly Val Ile
            180                 185                 190

Arg Leu Ile Gly Asn Pro Glu Thr Arg Tyr Arg Glu Asp Pro Val Arg
        195                 200                 205

Met Leu Arg Ala Val Arg Phe Ala Ala Lys Leu Gly Met Arg Ile Ser
    210                 215                 220

Pro Glu Thr Ala Glu Pro Ile Pro Arg Leu Ala Thr Leu Leu Asn Asp
225                 230                 235                 240

Ile Pro Pro Ala Arg Leu Phe Glu Glu Ser Leu Lys Leu Leu Gln Ala
                245                 250                 255

Gly Tyr Gly Tyr Glu Thr Tyr Lys Leu Leu Cys Glu Tyr His Leu Phe
            260                 265                 270

Gln Pro Leu Phe Pro Thr Ile Thr Arg Tyr Phe Thr Glu Asn Gly Asp
        275                 280                 285

Ser Pro Met Glu Arg Ile Ile Glu Gln Val Leu Lys Asn Thr Asp Thr
    290                 295                 300

Arg Ile His Asn Asp Met Arg Val Asn Pro Ala Phe Leu Phe Ala Ala
305                 310                 315                 320
```

```
Met Phe Trp Tyr Pro Leu Leu Glu Thr Ala Gln Lys Ile Ala Gln Glu
                325                 330                 335

Ser Gly Leu Thr Tyr His Asp Ala Phe Ala Leu Ala Met Asn Asp Val
            340                 345                 350

Leu Asp Glu Ala Cys Arg Ser Leu Ala Ile Pro Lys Arg Leu Thr Thr
        355                 360                 365

Leu Thr Arg Asp Ile Trp Gln Leu Gln Leu Arg Met Ser Arg Arg Gln
    370                 375                 380

Gly Lys Arg Ala Trp Lys Leu Leu Glu His Pro Lys Phe Arg Ala Ala
385                 390                 395                 400

Tyr Asp Leu Leu Ala Leu Arg Ala Glu Val Glu Arg Asn Ala Glu Leu
                405                 410                 415

Gln Arg Leu Val Lys Trp Trp Gly Glu Phe Gln Val Ser Ala Pro Pro
            420                 425                 430

Asp Gln Lys Gly Met Leu Asn Glu Leu Asp Glu Glu Pro Ser Pro Arg
        435                 440                 445

Arg Arg Thr Arg Arg Pro Arg Lys Arg Ala Pro Arg Arg Glu Gly Thr
    450                 455                 460

Ala
465

<210> SEQ ID NO 11
<211> LENGTH: 714
<212> TYPE: PRT
<213> ORGANISM: Escherichia coli

<400> SEQUENCE: 11

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220
```

-continued

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
            245                 250                 255

Val Thr Phe Cys Ala Arg Ser Ile Pro His Met Leu Glu His Phe Arg
        260                 265                 270

Ala Gly Ser Leu Leu Val Thr Ser Ala Asp Arg Pro Asp Val Leu Val
            275                 280                 285

Ala Ala Cys Leu Ala Ala Met Asn Gly Val Glu Ile Gly Ala Leu Leu
        290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
                435                 440                 445

Gly Val Glu Leu Gly Ala Gly Ile Glu Ile Val Asp Pro Glu Val Val
        450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
        610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
            645                 650                 655

Leu Asn Thr Gly Asn Thr Thr Tyr Lys Ala Val Gln Arg Ser Ala Asp
        660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
    690                 695                 700

Leu Thr Ala Ile Gln Ser Ala Gln Gln Gln
705                 710

<210> SEQ ID NO 12
<211> LENGTH: 223
<212> TYPE: PRT
<213> ORGANISM: Escherichia coli

<400> SEQUENCE: 12

Met Gln Tyr Pro Ile Asn Glu Met Phe Gln Thr Leu Gln Gly Glu Gly
1               5                   10                  15

Tyr Phe Thr Gly Val Pro Ala Ile Phe Ile Arg Leu Gln Gly Cys Pro
            20                  25                  30

Val Gly Cys Ala Trp Cys Asp Thr Lys His Thr Trp Glu Lys Leu Glu
        35                  40                  45

Asp Arg Glu Val Ser Leu Phe Ser Ile Leu Ala Lys Thr Lys Glu Ser
    50                  55                  60

Asp Lys Trp Gly Ala Ala Ser Ser Glu Asp Leu Leu Ala Val Ile Gly
65                  70                  75                  80

Arg Gln Gly Tyr Thr Ala Arg His Val Val Ile Thr Gly Gly Glu Pro
                85                  90                  95

Cys Ile His Asp Leu Leu Pro Leu Thr Asp Leu Leu Glu Lys Asn Gly
            100                 105                 110

Phe Ser Cys Gln Ile Glu Thr Ser Gly Thr His Glu Val Arg Cys Thr
        115                 120                 125

Pro Asn Thr Trp Val Thr Val Ser Pro Lys Leu Asn Met Arg Gly Gly
    130                 135                 140

Tyr Glu Val Leu Ser Gln Ala Leu Glu Arg Ala Asn Glu Ile Lys His
145                 150                 155                 160

Pro Val Gly Arg Val Arg Asp Ile Glu Ala Leu Asp Glu Leu Leu Ala
                165                 170                 175

Thr Leu Thr Asp Asp Lys Pro Arg Val Ile Ala Leu Gln Pro Ile Ser
            180                 185                 190

Gln Lys Asp Asp Ala Thr Arg Leu Cys Ile Glu Thr Cys Ile Ala Arg
        195                 200                 205

Asn Trp Arg Leu Ser Met Gln Thr His Lys Tyr Leu Asn Ile Ala
    210                 215                 220

<210> SEQ ID NO 13
<211> LENGTH: 370
<212> TYPE: PRT
<213> ORGANISM: Escherichia coli

<400> SEQUENCE: 13

Met Val Asn Val Arg Gln Pro Arg Asp Val Ala Gln Ile Leu Leu Ser
1               5                   10                  15

Val Leu Phe Leu Ala Ile Met Ile Val Ala Cys Leu Trp Ile Val Gln
            20                  25                  30

Pro Phe Ile Leu Gly Phe Ala Trp Ala Gly Thr Val Val Ile Ala Thr
            35                  40                  45

Trp Pro Val Leu Leu Arg Leu Gln Lys Ile Met Phe Gly Arg Arg Ser
 50                  55                  60

Leu Ala Val Leu Val Met Thr Leu Leu Val Met Val Phe Ile Ile
 65                  70                  75                  80

Pro Ile Ala Leu Leu Val Asn Ser Ile Val Asp Gly Ser Gly Pro Leu
                 85                  90                  95

Ile Lys Ala Ile Ser Ser Gly Asp Met Thr Leu Pro Asp Leu Ala Trp
            100                 105                 110

Leu Asn Thr Ile Pro Val Ile Gly Ala Lys Leu Tyr Ala Gly Trp His
            115                 120                 125

Asn Leu Leu Asp Met Gly Gly Thr Ala Ile Met Ala Lys Val Arg Pro
130                 135                 140

Tyr Ile Gly Thr Thr Thr Thr Trp Phe Val Gly Gln Ala Ala His Ile
145                 150                 155                 160

Gly Arg Phe Met Val His Cys Ala Leu Met Leu Leu Phe Ser Ala Leu
                165                 170                 175

Leu Tyr Trp Arg Gly Glu Gln Val Ala Gln Gly Ile Arg His Phe Ala
            180                 185                 190

Thr Arg Leu Ala Gly Val Arg Gly Asp Ala Ala Val Leu Leu Ala Ala
            195                 200                 205

Gln Ala Ile Arg Ala Val Ala Leu Gly Val Val Thr Ala Leu Val
            210                 215                 220

Gln Ala Val Leu Gly Gly Ile Gly Leu Ala Val Ser Gly Val Pro Tyr
225                 230                 235                 240

Ala Thr Leu Leu Thr Val Leu Met Ile Leu Ser Cys Leu Val Gln Leu
                245                 250                 255

Gly Pro Leu Pro Val Leu Ile Pro Ala Ile Ile Trp Leu Tyr Trp Thr
            260                 265                 270

Gly Asp Thr Thr Trp Gly Thr Val Leu Leu Val Trp Ser Gly Val Val
            275                 280                 285

Gly Thr Leu Asp Asn Val Ile Arg Pro Met Leu Ile Arg Met Gly Ala
290                 295                 300

Asp Leu Pro Leu Ile Leu Ile Leu Ser Gly Val Ile Gly Gly Leu Ile
305                 310                 315                 320

Ala Phe Gly Met Ile Gly Leu Phe Ile Gly Pro Val Leu Leu Ala Val
                325                 330                 335

Ser Trp Arg Leu Phe Ala Ala Trp Val Glu Glu Val Pro Pro Pro Thr
            340                 345                 350

Asp Gln Pro Glu Glu Ile Leu Glu Glu Leu Gly Glu Ile Glu Lys Pro
            355                 360                 365

Asn Lys
370

<210> SEQ ID NO 14
<211> LENGTH: 378
<212> TYPE: PRT
<213> ORGANISM: Escherichia coli

<400> SEQUENCE: 14

Met Lys Ile Leu Val Asp Glu Asn Met Pro Tyr Ala Arg Asp Leu Phe
 1               5                  10                  15

Ser Arg Leu Gly Glu Val Thr Ala Val Pro Gly Arg Pro Ile Pro Val
            20                  25                  30

Ala Gln Leu Ala Asp Ala Asp Ala Leu Met Val Arg Ser Val Thr Lys
             35                  40                  45

Val Asn Glu Ser Leu Leu Ala Gly Lys Pro Ile Lys Phe Val Gly Thr
 50                  55                  60

Ala Thr Ala Gly Thr Asp His Val Asp Glu Ala Trp Leu Lys Gln Ala
 65                  70                  75                  80

Gly Ile Gly Phe Ser Ala Ala Pro Gly Cys Asn Ala Ile Ala Val Val
                 85                  90                  95

Glu Tyr Val Phe Ser Ser Leu Leu Met Leu Ala Glu Arg Asp Gly Phe
                100                 105                 110

Ser Leu Tyr Asp Arg Thr Val Gly Ile Val Gly Val Gly Asn Val Gly
            115                 120                 125

Arg Arg Leu Gln Ala Arg Leu Glu Ala Leu Gly Ile Lys Thr Leu Leu
130                 135                 140

Cys Asp Pro Pro Arg Ala Asp Arg Gly Asp Glu Gly Asp Phe Arg Ser
145                 150                 155                 160

Leu Asp Glu Leu Val Gln Arg Ala Asp Ile Leu Thr Phe His Thr Pro
                165                 170                 175

Leu Phe Lys Asp Gly Pro Tyr Lys Thr Leu His Leu Ala Asp Glu Lys
            180                 185                 190

Leu Ile Arg Ser Leu Lys Pro Gly Ala Ile Leu Ile Asn Ala Cys Arg
            195                 200                 205

Gly Ala Val Val Asp Asn Thr Ala Leu Leu Thr Cys Leu Asn Glu Gly
210                 215                 220

Gln Lys Leu Ser Val Val Leu Asp Val Trp Glu Gly Glu Pro Glu Leu
225                 230                 235                 240

Asn Val Glu Leu Leu Lys Lys Val Asp Ile Gly Thr Ser His Ile Ala
                245                 250                 255

Gly Tyr Thr Leu Glu Gly Lys Ala Arg Gly Thr Thr Gln Val Phe Glu
            260                 265                 270

Ala Tyr Ser Lys Phe Ile Gly His Glu Gln His Val Ala Leu Asp Thr
            275                 280                 285

Leu Leu Pro Ala Pro Glu Phe Gly Arg Ile Thr Leu His Gly Pro Leu
290                 295                 300

Asp Gln Pro Thr Leu Lys Arg Leu Val His Leu Val Tyr Asp Val Arg
305                 310                 315                 320

Arg Asp Asp Ala Pro Leu Arg Lys Val Ala Gly Ile Pro Gly Glu Phe
                325                 330                 335

Asp Lys Leu Arg Lys Asn Tyr Leu Glu Arg Arg Glu Trp Ser Ser Leu
            340                 345                 350

Tyr Val Ile Cys Asp Asp Ala Ser Ala Ala Ser Leu Leu Cys Lys Leu
            355                 360                 365

Gly Phe Asn Ala Val His His Pro Ala Arg
370                 375

<210> SEQ ID NO 15
<211> LENGTH: 2367
<212> TYPE: PRT
<213> ORGANISM: Escherichia coli

<400> SEQUENCE: 15

Met Leu Ala Arg Ser Gly Lys Val Ser Met Ala Thr Lys Lys Arg Ser
1               5                   10                  15

Gly Glu Glu Ile Asn Asp Arg Gln Ile Leu Cys Gly Met Gly Ile Lys

```
                    20                  25                  30
Leu Arg Arg Leu Thr Ala Gly Ile Cys Leu Ile Thr Gln Leu Ala Phe
                35                  40                  45
Pro Met Ala Ala Ala Gln Gly Val Val Asn Ala Ala Thr Gln Gln
         50                  55                  60
Pro Val Pro Ala Gln Ile Ala Ile Ala Asn Ala Asn Thr Val Pro Tyr
 65                  70                  75                  80
Thr Leu Gly Ala Leu Glu Ser Ala Gln Ser Val Ala Glu Arg Phe Gly
                 85                  90                  95
Ile Ser Val Ala Glu Leu Arg Lys Leu Asn Gln Phe Arg Thr Phe Ala
                100                 105                 110
Arg Gly Phe Asp Asn Val Arg Gln Gly Asp Glu Leu Asp Val Pro Ala
                115                 120                 125
Gln Val Ser Glu Lys Lys Leu Thr Pro Pro Gly Asn Ser Ser Asp
            130                 135                 140
Asn Leu Glu Gln Gln Ile Ala Ser Thr Ser Gln Gln Ile Gly Ser Leu
145                 150                 155                 160
Leu Ala Glu Asp Met Asn Ser Glu Gln Ala Ala Asn Met Ala Arg Gly
                165                 170                 175
Trp Ala Ser Ser Gln Ala Ser Gly Ala Met Thr Asp Trp Leu Ser Arg
                180                 185                 190
Phe Gly Thr Ala Arg Ile Thr Leu Gly Val Asp Glu Asp Phe Ser Leu
                195                 200                 205
Lys Asn Ser Gln Phe Asp Phe Leu His Pro Trp Tyr Glu Thr Pro Asp
                210                 215                 220
Asn Leu Phe Phe Ser Gln His Thr Leu His Arg Thr Asp Glu Arg Thr
225                 230                 235                 240
Gln Ile Asn Asn Gly Leu Gly Trp Arg His Phe Thr Pro Thr Trp Met
                245                 250                 255
Ser Gly Ile Asn Phe Phe Asp His Asp Leu Ser Arg Tyr His Ser
            260                 265                 270
Arg Ala Gly Ile Gly Ala Glu Tyr Trp Arg Asp Tyr Leu Lys Leu Ser
                275                 280                 285
Ser Asn Gly Tyr Leu Arg Leu Thr Asn Trp Arg Ser Ala Pro Glu Leu
                290                 295                 300
Asp Asn Asp Tyr Glu Ala Arg Pro Ala Asn Gly Trp Asp Val Arg Ala
305                 310                 315                 320
Glu Ser Trp Leu Pro Ala Trp Pro His Leu Gly Gly Lys Leu Val Tyr
                325                 330                 335
Glu Gln Tyr Tyr Gly Asp Glu Val Ala Leu Phe Asp Lys Asp Asp Arg
                340                 345                 350
Gln Ser Asn Pro His Ala Ile Thr Ala Gly Leu Asn Tyr Thr Pro Phe
                355                 360                 365
Pro Leu Met Thr Phe Ser Ala Glu Gln Arg Gln Gly Lys Gln Gly Glu
                370                 375                 380
Asn Asp Thr Arg Phe Ala Val Asp Phe Thr Trp Gln Pro Gly Ser Ala
385                 390                 395                 400
Met Gln Lys Gln Leu Asp Pro Asn Glu Val Ala Ala Arg Arg Ser Leu
                405                 410                 415
Ala Gly Ser Arg Tyr Asp Leu Val Asp Arg Asn Asn Asn Ile Val Leu
                420                 425                 430
Glu Tyr Arg Lys Lys Glu Leu Val Arg Leu Thr Leu Thr Asp Pro Val
                435                 440                 445
```

```
Thr Gly Lys Ser Gly Glu Val Lys Ser Leu Val Ser Leu Gln Thr
    450                 455                 460
Lys Tyr Ala Leu Lys Gly Tyr Asn Val Glu Ala Thr Ala Leu Glu Ala
465                 470                 475                 480
Ala Gly Gly Lys Val Val Thr Gly Lys Asp Ile Leu Val Thr Leu
                    485                 490                 495
Pro Ala Tyr Arg Phe Thr Ser Thr Pro Glu Thr Asp Asn Thr Trp Pro
                500                 505                 510
Ile Glu Val Thr Ala Glu Asp Val Lys Gly Asn Leu Ser Asn Arg Glu
                515                 520                 525
Gln Ser Met Val Val Gln Ala Pro Thr Leu Ser Gln Lys Asp Ser
530                 535                 540
Ser Val Ser Leu Ser Thr Gln Thr Leu Asn Ala Asp Ser His Ser Thr
545                 550                 555                 560
Ala Thr Leu Thr Phe Ile Ala His Asp Ala Ala Gly Asn Pro Val Val
                565                 570                 575
Gly Leu Val Leu Ser Thr Arg His Glu Gly Val Gln Asp Ile Thr Leu
                580                 585                 590
Ser Asp Trp Lys Asp Asn Gly Asp Gly Ser Tyr Thr Gln Ile Leu Thr
        595                 600                 605
Thr Gly Ala Met Ser Gly Thr Leu Thr Leu Met Pro Gln Leu Asn Gly
    610                 615                 620
Val Asp Ala Ala Lys Ala Pro Ala Val Val Asn Ile Ile Ser Val Ser
625                 630                 635                 640
Ser Ser Arg Thr His Ser Ser Ile Lys Ile Asp Lys Asp Arg Tyr Leu
                645                 650                 655
Ser Gly Asn Pro Ile Glu Val Thr Val Glu Leu Arg Asp Glu Asn Asp
                660                 665                 670
Lys Pro Val Lys Glu Gln Lys Gln Gln Leu Asn Asn Ala Val Ser Ile
                675                 680                 685
Asp Asn Val Lys Pro Gly Val Thr Thr Asp Trp Lys Glu Thr Ala Asp
        690                 695                 700
Gly Val Tyr Lys Ala Thr Tyr Thr Ala Tyr Thr Lys Gly Ser Gly Leu
705                 710                 715                 720
Thr Ala Lys Leu Leu Met Gln Asn Trp Asn Glu Asp Leu His Thr Ala
                725                 730                 735
Gly Phe Ile Ile Asp Ala Asn Pro Gln Ser Ala Lys Ile Ala Thr Leu
                740                 745                 750
Ser Ala Ser Asn Asn Gly Val Leu Ala Asn Glu Asn Ala Ala Asn Thr
                755                 760                 765
Val Ser Val Asn Val Ala Asp Glu Gly Ser Asn Pro Ile Asn Asp His
770                 775                 780
Thr Val Thr Phe Ala Val Leu Ser Gly Ser Ala Thr Ser Phe Asn Asn
785                 790                 795                 800
Gln Asn Thr Ala Lys Thr Asp Val Asn Gly Leu Ala Thr Phe Asp Leu
                805                 810                 815
Lys Ser Ser Lys Gln Glu Asp Asn Thr Val Glu Val Thr Leu Glu Asn
                820                 825                 830
Gly Val Lys Gln Thr Leu Ile Val Ser Phe Val Gly Asp Ser Ser Thr
            835                 840                 845
Ala Gln Val Asp Leu Gln Lys Ser Lys Asn Glu Val Val Ala Asp Gly
    850                 855                 860
```

```
Asn Asp Ser Val Thr Met Thr Ala Thr Val Arg Asp Ala Lys Gly Asn
865                 870                 875                 880

Leu Leu Asn Asp Val Met Val Thr Phe Asn Val Asn Ser Ala Glu Ala
            885                 890                 895

Lys Leu Ser Gln Thr Glu Val Asn Ser His Asp Gly Ile Ala Thr Ala
                900                 905                 910

Thr Leu Thr Ser Leu Lys Asn Gly Asp Tyr Arg Val Thr Ala Ser Val
            915                 920                 925

Ser Gly Ser Gln Ala Asn Gln Gln Val Asn Phe Ile Gly Asp Gln
    930                 935                 940

Ser Thr Ala Ala Leu Thr Leu Ser Val Pro Ser Gly Asp Ile Thr Val
945                 950                 955                 960

Thr Asn Thr Ala Pro Gln Tyr Met Thr Ala Thr Leu Gln Asp Lys Asn
                965                 970                 975

Gly Asn Pro Leu Lys Asp Lys Glu Ile Thr Phe Ser Val Pro Asn Asp
            980                 985                 990

Val Ala Ser Lys Phe Ser Ile Ser Asn Gly Gly Lys Gly Met Thr Asp
                995                 1000                1005

Ser Asn Gly Val Ala Ile Ala Ser Leu Thr Gly Thr Leu Ala Gly
    1010                1015                1020

Thr His Met Ile Met Ala Arg Leu Ala Asn Ser Asn Val Ser Asp
    1025                1030                1035

Ala Gln Pro Met Thr Phe Val Ala Asp Lys Asp Arg Ala Val Val
    1040                1045                1050

Val Leu Gln Thr Ser Lys Ala Glu Ile Ile Gly Asn Gly Val Asp
    1055                1060                1065

Glu Thr Thr Leu Thr Ala Thr Val Lys Asp Pro Ser Asn His Pro
    1070                1075                1080

Val Ala Gly Ile Thr Val Asn Phe Thr Met Pro Gln Asp Val Ala
    1085                1090                1095

Ala Asn Phe Thr Leu Glu Asn Asn Gly Ile Ala Ile Thr Gln Ala
    1100                1105                1110

Asn Gly Glu Ala His Val Thr Leu Lys Gly Lys Lys Ala Gly Thr
    1115                1120                1125

His Thr Val Thr Ala Thr Leu Gly Asn Asn Asn Thr Ser Asp Ser
    1130                1135                1140

Gln Pro Val Thr Phe Val Ala Asp Lys Ala Ser Ala Gln Val Val
    1145                1150                1155

Leu Gln Ile Ser Lys Asp Glu Ile Thr Gly Asn Gly Val Asp Ser
    1160                1165                1170

Ala Thr Leu Thr Ala Thr Val Lys Asp Gln Phe Asp Asn Glu Val
    1175                1180                1185

Asn Asn Leu Pro Val Thr Phe Ser Ser Ala Ser Ser Gly Leu Thr
    1190                1195                1200

Leu Thr Pro Gly Val Ser Asn Thr Asn Glu Ser Gly Ile Ala Gln
    1205                1210                1215

Ala Thr Leu Ala Gly Val Ala Phe Gly Glu Lys Thr Val Thr Ala
    1220                1225                1230

Ser Leu Ala Asn Asn Gly Ala Ser Asp Asn Lys Thr Val His Phe
    1235                1240                1245

Ile Gly Asp Thr Ala Ala Ala Lys Ile Ile Glu Leu Ala Pro Val
    1250                1255                1260

Pro Asp Ser Ile Ile Ala Gly Thr Pro Gln Asn Ser Ser Gly Ser
```

```
                1265                1270                1275
Val Ile Thr Ala Thr Val Val Asp Asn Asn Gly Phe Pro Val Lys
            1280                1285                1290
Gly Val Thr Val Asn Phe Thr Ser Asn Ala Ala Thr Ala Glu Met
            1295                1300                1305
Thr Asn Gly Gly Gln Ala Val Thr Asn Glu Gln Gly Lys Ala Thr
            1310                1315                1320
Val Thr Tyr Thr Asn Thr Arg Ser Ser Ile Glu Ser Gly Ala Arg
            1325                1330                1335
Pro Asp Thr Val Glu Ala Ser Leu Glu Asn Gly Ser Ser Thr Leu
            1340                1345                1350
Ser Thr Ser Ile Asn Val Asn Ala Asp Ala Ser Thr Ala His Leu
            1355                1360                1365
Thr Leu Leu Gln Ala Leu Phe Asp Thr Val Ser Ala Gly Glu Thr
            1370                1375                1380
Thr Ser Leu Tyr Ile Glu Val Lys Asp Asn Tyr Gly Asn Gly Val
            1385                1390                1395
Pro Gln Gln Glu Val Thr Leu Ser Val Ser Pro Ser Glu Gly Val
            1400                1405                1410
Thr Pro Ser Asn Asn Ala Ile Tyr Thr Thr Asn His Asp Gly Asn
            1415                1420                1425
Phe Tyr Ala Ser Phe Thr Ala Thr Lys Ala Gly Val Tyr Gln Leu
            1430                1435                1440
Thr Ala Thr Leu Glu Asn Gly Asp Ser Met Gln Gln Thr Val Thr
            1445                1450                1455
Tyr Val Pro Asn Val Ala Asn Ala Glu Ile Thr Leu Ala Ala Ser
            1460                1465                1470
Lys Asp Pro Val Ile Ala Asp Asn Asn Asp Leu Thr Thr Leu Thr
            1475                1480                1485
Ala Thr Val Ala Asp Thr Glu Gly Asn Ala Ile Ala Asn Thr Glu
            1490                1495                1500
Val Thr Phe Thr Leu Pro Glu Asp Val Lys Ala Asn Phe Thr Leu
            1505                1510                1515
Ser Asp Gly Gly Lys Val Ile Thr Asp Ala Glu Gly Lys Ala Lys
            1520                1525                1530
Val Thr Leu Lys Gly Thr Lys Ala Gly Ala His Thr Val Thr Ala
            1535                1540                1545
Ser Met Thr Gly Gly Lys Ser Glu Gln Leu Val Val Asn Phe Ile
            1550                1555                1560
Ala Asp Thr Leu Thr Ala Gln Val Asn Leu Asn Val Thr Glu Asp
            1565                1570                1575
Asn Phe Ile Ala Asn Asn Val Gly Met Thr Arg Leu Gln Ala Thr
            1580                1585                1590
Val Thr Asp Gly Asn Gly Asn Pro Leu Ala Asn Glu Ala Val Thr
            1595                1600                1605
Phe Thr Leu Pro Ala Asp Val Ser Ala Ser Phe Thr Leu Gly Gln
            1610                1615                1620
Gly Gly Ser Ala Ile Thr Asp Ile Asn Gly Lys Ala Glu Val Thr
            1625                1630                1635
Leu Ser Gly Thr Lys Ser Gly Thr Tyr Pro Val Thr Val Ser Val
            1640                1645                1650
Asn Asn Tyr Gly Val Ser Asp Thr Lys Gln Val Thr Leu Ile Ala
            1655                1660                1665
```

-continued

```
Asp Ala Gly Thr Ala Lys Leu Ala Ser Leu Thr Ser Val Tyr Ser
    1670            1675            1680

Phe Val Val Ser Thr Thr Glu Gly Ala Thr Met Thr Ala Ser Val
    1685            1690            1695

Thr Asp Ala Asn Gly Asn Pro Val Glu Gly Ile Lys Val Asn Phe
    1700            1705            1710

Arg Gly Thr Ser Val Thr Leu Ser Ser Thr Ser Val Glu Thr Asp
    1715            1720            1725

Asp Arg Gly Phe Ala Glu Ile Leu Val Thr Ser Thr Glu Val Gly
    1730            1735            1740

Leu Lys Thr Val Ser Ala Ser Leu Ala Asp Lys Pro Thr Glu Val
    1745            1750            1755

Ile Ser Arg Leu Leu Asn Ala Ser Ala Asp Val Asn Ser Ala Thr
    1760            1765            1770

Ile Thr Ser Leu Glu Ile Pro Glu Gly Gln Val Met Val Ala Gln
    1775            1780            1785

Asp Val Ala Val Lys Ala His Val Asn Asp Gln Phe Gly Asn Pro
    1790            1795            1800

Val Ala His Gln Pro Val Thr Phe Ser Ala Glu Pro Ser Ser Gln
    1805            1810            1815

Met Ile Ile Ser Gln Asn Thr Val Ser Thr Asn Thr Gln Gly Val
    1820            1825            1830

Ala Glu Val Thr Met Thr Pro Glu Arg Asn Gly Ser Tyr Met Val
    1835            1840            1845

Lys Ala Ser Leu Pro Asn Gly Ala Ser Leu Glu Lys Gln Leu Glu
    1850            1855            1860

Ala Ile Asp Glu Lys Leu Thr Leu Thr Ala Ser Ser Pro Leu Ile
    1865            1870            1875

Gly Val Tyr Ala Pro Thr Gly Ala Thr Leu Thr Ala Thr Leu Thr
    1880            1885            1890

Ser Ala Asn Gly Thr Pro Val Glu Gly Gln Val Ile Asn Phe Ser
    1895            1900            1905

Val Thr Pro Glu Gly Ala Thr Leu Ser Gly Gly Lys Val Arg Thr
    1910            1915            1920

Asn Ser Ser Gly Gln Ala Pro Val Val Leu Thr Ser Asn Lys Val
    1925            1930            1935

Gly Thr Tyr Thr Val Thr Ala Ser Phe His Asn Gly Val Thr Ile
    1940            1945            1950

Gln Thr Gln Thr Thr Val Lys Val Thr Gly Asn Ser Ser Thr Ala
    1955            1960            1965

His Val Ala Ser Phe Ile Ala Asp Pro Ser Thr Ile Ala Ala Thr
    1970            1975            1980

Asn Thr Asp Leu Ser Thr Leu Lys Ala Thr Val Glu Asp Gly Ser
    1985            1990            1995

Gly Asn Leu Ile Glu Gly Leu Thr Val Tyr Phe Ala Leu Lys Ser
    2000            2005            2010

Gly Ser Ala Thr Leu Thr Ser Leu Thr Ala Val Thr Asp Gln Asn
    2015            2020            2025

Gly Ile Ala Thr Thr Ser Val Lys Gly Ala Met Thr Gly Ser Val
    2030            2035            2040

Thr Val Ser Ala Val Thr Thr Ala Gly Gly Met Gln Thr Val Asp
    2045            2050            2055
```

```
Ile Thr Leu Val Ala Gly Pro Ala Asp Thr Ser Gln Ser Val Leu
    2060                2065                2070

Lys Ser Asn Arg Ser Ser Leu Lys Gly Asp Tyr Thr Asp Ser Ala
    2075                2080                2085

Glu Leu Arg Leu Val Leu His Asp Ile Ser Gly Asn Pro Ile Lys
    2090                2095                2100

Val Ser Glu Gly Met Glu Phe Val Gln Ser Gly Thr Asn Val Pro
    2105                2110                2115

Tyr Ile Lys Ile Ser Ala Ile Asp Tyr Ser Leu Asn Ile Asn Gly
    2120                2125                2130

Asp Tyr Lys Ala Thr Val Thr Gly Gly Gly Glu Gly Ile Ala Thr
    2135                2140                2145

Leu Ile Pro Val Leu Asn Gly Val His Gln Ala Gly Leu Ser Thr
    2150                2155                2160

Thr Ile Gln Phe Thr Arg Ala Glu Asp Lys Ile Met Ser Gly Thr
    2165                2170                2175

Val Ser Val Asn Gly Thr Asp Leu Pro Thr Thr Thr Phe Pro Ser
    2180                2185                2190

Gln Gly Phe Thr Gly Ala Tyr Tyr Gln Leu Asn Asn Asp Asn Phe
    2195                2200                2205

Ala Pro Gly Lys Thr Ala Ala Asp Tyr Glu Phe Ser Ser Ser Ala
    2210                2215                2220

Ser Trp Val Asp Val Asp Ala Thr Gly Lys Val Thr Phe Lys Asn
    2225                2230                2235

Val Gly Ser Asn Ser Glu Arg Ile Thr Ala Thr Pro Lys Ser Gly
    2240                2245                2250

Gly Pro Ser Tyr Val Tyr Glu Ile Arg Val Lys Ser Trp Trp Val
    2255                2260                2265

Asn Ala Gly Glu Ala Phe Met Ile Tyr Ser Leu Ala Glu Asn Phe
    2270                2275                2280

Cys Ser Ser Asn Gly Tyr Thr Leu Pro Arg Ala Asn Tyr Leu Asn
    2285                2290                2295

His Cys Ser Ser Arg Gly Ile Gly Ser Leu Tyr Ser Glu Trp Gly
    2300                2305                2310

Asp Met Gly His Tyr Thr Thr Asp Ala Gly Phe Gln Ser Asn Met
    2315                2320                2325

Tyr Trp Ser Ser Ser Pro Ala Asn Ser Ser Glu Gln Tyr Val Val
    2330                2335                2340

Ser Leu Ala Thr Gly Asp Gln Ser Val Phe Glu Lys Leu Gly Phe
    2345                2350                2355

Ala Tyr Ala Thr Cys Tyr Lys Asn Leu
    2360                2365

<210> SEQ ID NO 16
<211> LENGTH: 1093
<212> TYPE: PRT
<213> ORGANISM: Escherichia coli

<400> SEQUENCE: 16

Met Thr Pro Val Lys Val Trp Gln Glu Arg Val Glu Ile Pro Thr Tyr
1               5                   10                  15

Glu Thr Gly Pro Gln Asp Ile His Pro Met Phe Leu Glu Asn Arg Val
                20                  25                  30

Tyr Gln Gly Ser Ser Gly Ala Val Tyr Pro Tyr Gly Val Thr Asp Thr
            35                  40                  45
```

-continued

```
Leu Ser Glu Gln Lys Thr Leu Lys Ser Trp Gln Ala Val Trp Leu Glu
 50                  55                  60
Asn Asp Tyr Ile Lys Val Met Ile Leu Pro Glu Leu Gly Gly Arg Val
 65                  70                  75                  80
His Arg Ala Trp Asp Lys Val Lys Gln Arg Asp Phe Val Tyr His Asn
                 85                  90                  95
Glu Val Ile Lys Pro Ala Leu Val Gly Leu Gly Pro Trp Ile Ser
                100                 105                 110
Gly Gly Ile Glu Phe Asn Trp Pro Gln His His Arg Pro Thr Thr Phe
            115                 120                 125
Met Pro Val Asp Phe Thr Leu Glu Ala His Glu Asp Gly Ala Gln Thr
130                 135                 140
Val Trp Val Gly Glu Thr Glu Pro Met His Gly Leu Gln Val Met Thr
145                 150                 155                 160
Gly Phe Thr Leu Arg Pro Asp Arg Ala Ala Leu Glu Ile Ala Ser Arg
                165                 170                 175
Val Tyr Asn Gly Asn Ala Thr Pro Arg His Phe Leu Trp Trp Ala Asn
            180                 185                 190
Pro Ala Val Lys Gly Gly Glu Gly His Gln Ser Val Phe Pro Pro Asp
            195                 200                 205
Val Thr Ala Val Phe Asp His Gly Lys Arg Ala Val Ser Ala Phe Pro
210                 215                 220
Ile Ala Thr Gly Thr Tyr Tyr Lys Val Asp Tyr Ser Ala Gly Val Asp
225                 230                 235                 240
Ile Ser Arg Tyr Lys Asn Val Pro Val Pro Thr Ser Tyr Met Ala Glu
                245                 250                 255
Lys Ser Gln Tyr Asp Phe Val Gly Ala Trp Cys His Asp Glu Asp Gly
            260                 265                 270
Gly Leu Leu His Val Ala Asn His His Ile Ala Pro Gly Lys Lys Gln
            275                 280                 285
Trp Ser Trp Gly His Ser Glu Phe Gly Gln Ala Trp Asp Lys Ser Leu
290                 295                 300
Thr Asp Asn Asn Gly Pro Tyr Ile Glu Leu Met Thr Gly Ile Phe Ala
305                 310                 315                 320
Asp Asn Gln Pro Asp Phe Thr Trp Leu Asp Ala Tyr Glu Glu Lys Arg
                325                 330                 335
Phe Glu Gln Tyr Phe Leu Pro Tyr His Ser Leu Gly Met Val Gln Asn
            340                 345                 350
Ala Ser Arg Asp Ala Val Ile Lys Leu Gln Arg Ser Lys Arg Gly Ile
            355                 360                 365
Glu Trp Gly Leu Tyr Ala Ile Ser Pro Leu Asn Gly Tyr Arg Leu Ala
370                 375                 380
Ile Arg Glu Ile Gly Lys Cys Asn Ala Leu Leu Asp Asp Ala Val Ala
385                 390                 395                 400
Leu Met Pro Ala Thr Ala Ile Gln Gly Val Leu His Gly Ile Asn Pro
                405                 410                 415
Glu Arg Leu Thr Ile Glu Leu Ser Asp Ala Asp Gly Asn Ile Val Leu
            420                 425                 430
Ser Tyr Gln Glu His Gln Pro Gln Ala Leu Pro Leu Pro Asp Val Ala
            435                 440                 445
Lys Ala Pro Leu Ala Ala Gln Asp Ile Thr Ser Thr Asp Glu Ala Trp
450                 455                 460
```

```
Phe Ile Gly Gln His Leu Glu Gln Tyr His Ala Ser Arg Ser Pro
465                 470                 475                 480

Phe Asp Tyr Tyr Leu Arg Gly Val Ala Leu Asp Pro Leu Asp Tyr Arg
            485                 490                 495

Cys Asn Leu Ala Leu Ala Met Leu Glu Tyr Asn Arg Ala Asp Phe Pro
                500                 505                 510

Gln Ala Val Ala Tyr Ala Thr Gln Ala Leu Lys Arg Ala His Ala Leu
            515                 520                 525

Asn Lys Asn Pro Gln Cys Gln Ala Ser Leu Ile Arg Ala Ser Ala
530                 535                 540

Tyr Glu Arg Gln Gly Gln Tyr Gln Gln Ala Glu Glu Asp Phe Trp Arg
545                 550                 555                 560

Ala Val Trp Ser Gly Asn Ser Lys Ala Gly Gly Tyr Tyr Gly Leu Ala
                565                 570                 575

Arg Leu Ala Ala Arg Asn Gly Asn Phe Asp Ala Gly Leu Asp Phe Cys
                580                 585                 590

Gln Gln Ser Leu Arg Ala Cys Pro Thr Asn Gln Glu Val Leu Cys Leu
            595                 600                 605

His Asn Leu Leu Leu Val Leu Ser Gly Arg Gln Asp Asn Ala Arg Val
610                 615                 620

Gln Arg Glu Lys Leu Leu Arg Asp Tyr Pro Leu Asn Ala Thr Leu Trp
625                 630                 635                 640

Trp Leu Asn Trp Phe Asp Gly Arg Ser Glu Ser Ala Leu Ala Gln Trp
                645                 650                 655

Arg Gly Leu Cys Gln Gly Arg Asp Val Asn Ala Leu Met Thr Ala Gly
                660                 665                 670

Gln Leu Ile Asn Trp Gly Met Pro Thr Leu Ala Ala Glu Met Leu Asn
            675                 680                 685

Ala Leu Asp Cys Gln Arg Thr Leu Pro Leu Tyr Leu Gln Ala Ser Leu
690                 695                 700

Leu Pro Lys Ala Glu Arg Gly Glu Leu Val Ala Lys Ala Ile Asp Val
705                 710                 715                 720

Phe Pro Gln Phe Val Arg Phe Pro Asn Thr Leu Glu Glu Val Ala Ala
                725                 730                 735

Leu Glu Ser Ile Glu Glu Cys Trp Phe Ala Arg His Leu Leu Ala Cys
            740                 745                 750

Phe Tyr Tyr Asn Lys Arg Ser Tyr Asn Lys Ala Ile Ala Phe Trp Gln
            755                 760                 765

Arg Cys Val Glu Met Ser Pro Glu Phe Ala Asp Gly Trp Arg Gly Leu
770                 775                 780

Ala Ile His Ala Trp Asn Lys Gln His Asp Tyr Glu Leu Ala Ala Arg
785                 790                 795                 800

Tyr Leu Asp Asn Ala Tyr Gln Leu Ala Pro Gln Asp Ala Arg Leu Leu
            805                 810                 815

Phe Glu Arg Asp Leu Leu Asp Lys Leu Ser Gly Ala Thr Pro Glu Lys
            820                 825                 830

Arg Leu Ala Arg Leu Glu Asn Asn Leu Glu Ile Ala Leu Lys Arg Asp
            835                 840                 845

Asp Met Thr Ala Glu Leu Leu Asn Leu Trp His Leu Thr Gly Gln Ala
            850                 855                 860

Asp Lys Ala Ala Asp Ile Leu Ala Thr Arg Lys Phe His Pro Trp Glu
865                 870                 875                 880

Gly Gly Glu Gly Lys Val Thr Ser Gln Phe Ile Leu Asn Gln Leu Leu
```

```
                    885             890             895
Arg Ala Trp Gln His Leu Asp Ala Arg Gln Pro Gln Gln Ala Cys Glu
                900             905             910

Leu Leu His Ala Ala Leu His Tyr Pro Glu Asn Leu Ser Glu Gly Arg
            915             920             925

Leu Pro Gly Gln Thr Asp Asn Asp Ile Trp Phe Trp Gln Ala Ile Cys
        930             935             940

Ala Asn Ala Gln Gly Asp Glu Thr Glu Ala Thr Arg Cys Leu Arg Leu
945             950             955             960

Ala Ala Thr Gly Asp Arg Thr Ile Asn Ile His Ser Tyr Tyr Asn Asp
            965             970             975

Gln Pro Val Asp Tyr Leu Phe Trp Gln Gly Met Ala Leu Arg Leu Leu
        980             985             990

Gly Glu Gln Gln Thr Ala Gln Gln Leu Phe Ser Glu Met Lys Gln Trp
    995             1000            1005

Ala Gln Glu Met Ala Lys Thr Ser Ile Glu Ala Asp Phe Phe Ala
    1010            1015            1020

Val Ser Gln Pro Asp Leu Leu Ser Leu Tyr Gly Asp Leu Gln Gln
    1025            1030            1035

Gln His Lys Glu Lys Cys Leu Met Val Ala Met Leu Ala Ser Ala
    1040            1045            1050

Gly Leu Gly Glu Val Ala Gln Tyr Glu Ser Ala Arg Ala Glu Leu
    1055            1060            1065

Thr Ala Ile Asn Pro Ala Trp Pro Lys Ala Ala Leu Phe Thr Thr
    1070            1075            1080

Val Met Pro Phe Ile Phe Asn Arg Val His
    1085            1090

<210> SEQ ID NO 17
<211> LENGTH: 365
<212> TYPE: PRT
<213> ORGANISM: Escherichia coli

<400> SEQUENCE: 17

Met Phe Glu Ile Asn Pro Val Asn Asn Arg Ile Gln Asp Leu Thr Glu
1               5                   10                  15

Arg Ser Asp Val Leu Arg Gly Tyr Leu Asp Tyr Asp Ala Lys Lys Glu
            20                  25                  30

Arg Leu Glu Glu Val Asn Ala Glu Leu Glu Gln Pro Asp Val Trp Asn
        35                  40                  45

Glu Pro Glu Arg Ala Gln Ala Leu Gly Lys Glu Arg Ser Ser Leu Glu
    50                  55                  60

Ala Val Val Asp Thr Leu Asp Gln Met Lys Gln Gly Leu Glu Asp Val
65                  70                  75                  80

Ser Gly Leu Leu Glu Leu Ala Val Glu Ala Asp Asp Glu Glu Thr Phe
                85                  90                  95

Asn Glu Ala Val Ala Glu Leu Asp Ala Leu Glu Glu Lys Leu Ala Gln
            100                 105                 110

Leu Glu Phe Arg Arg Met Phe Ser Gly Glu Tyr Asp Ser Ala Asp Cys
        115                 120                 125

Tyr Leu Asp Ile Gln Ala Gly Ser Gly Gly Thr Glu Ala Gln Asp Trp
    130                 135                 140

Ala Ser Met Leu Glu Arg Met Tyr Leu Arg Trp Ala Glu Ser Arg Gly
145                 150                 155                 160
```

Phe Lys Thr Glu Ile Ile Glu Ser Glu Gly Val Ala Gly Ile
                165                 170                 175

Lys Ser Val Thr Ile Lys Ile Ser Gly Asp Tyr Ala Tyr Gly Trp Leu
            180                 185                 190

Arg Thr Glu Thr Gly Val His Arg Leu Val Arg Lys Ser Pro Phe Asp
            195                 200                 205

Ser Gly Gly Arg Arg His Thr Ser Phe Ser Ser Ala Phe Val Tyr Pro
        210                 215                 220

Glu Val Asp Asp Asp Ile Asp Ile Glu Ile Asn Pro Ala Asp Leu Arg
225                 230                 235                 240

Ile Asp Val Tyr Arg Thr Ser Gly Ala Gly Gly Gln His Val Asn Arg
                245                 250                 255

Thr Glu Ser Ala Val Arg Ile Thr His Ile Pro Thr Gly Ile Val Thr
            260                 265                 270

Gln Cys Gln Asn Asp Arg Ser Gln His Lys Asn Lys Asp Gln Ala Met
        275                 280                 285

Lys Gln Met Lys Ala Lys Leu Tyr Glu Leu Glu Met Gln Lys Lys Asn
290                 295                 300

Ala Glu Lys Gln Ala Met Glu Asp Asn Lys Ser Asp Ile Gly Trp Gly
305                 310                 315                 320

Ser Gln Ile Arg Ser Tyr Val Leu Asp Asp Ser Arg Ile Lys Asp Leu
                325                 330                 335

Arg Thr Gly Val Glu Thr Arg Asn Thr Gln Ala Val Leu Asp Gly Ser
            340                 345                 350

Leu Asp Gln Phe Ile Glu Ala Ser Leu Lys Ala Gly Leu
        355                 360                 365

<210> SEQ ID NO 18
<211> LENGTH: 121
<212> TYPE: PRT
<213> ORGANISM: Escherichia coli

<400> SEQUENCE: 18

Met Ile Ser Arg Val Thr Glu Ala Leu Ser Lys Val Lys Gly Ser Met
1               5                   10                  15

Gly Ser His Glu Arg His Ala Leu Pro Gly Val Ile Gly Asp Asp Leu
            20                  25                  30

Leu Arg Phe Gly Lys Leu Pro Leu Cys Leu Phe Ile Cys Ile Ile Leu
        35                  40                  45

Thr Ala Val Thr Val Val Thr Thr Ala His His Thr Arg Leu Leu Thr
    50                  55                  60

Ala Gln Arg Glu Gln Leu Val Leu Glu Arg Asp Ala Leu Asp Ile Glu
65                  70                  75                  80

Trp Arg Asn Leu Ile Leu Glu Glu Asn Ala Leu Gly Asp His Ser Arg
                85                  90                  95

Val Glu Arg Ile Ala Thr Glu Lys Leu Gln Met Gln His Val Asp Pro
            100                 105                 110

Ser Gln Glu Asn Ile Val Val Gln Lys
        115                 120

<210> SEQ ID NO 19
<211> LENGTH: 305
<212> TYPE: PRT
<213> ORGANISM: Escherichia coli

<400> SEQUENCE: 19

```
Met Asn Ile Arg Asp Leu Glu Tyr Leu Val Ala Leu Ala Glu His Arg
1               5                   10                  15

His Phe Arg Arg Ala Ala Asp Ser Cys His Val Ser Gln Pro Thr Leu
            20                  25                  30

Ser Gly Gln Ile Arg Lys Leu Glu Asp Glu Leu Gly Val Met Leu Leu
        35                  40                  45

Glu Arg Thr Ser Arg Lys Val Leu Phe Thr Gln Ala Gly Met Leu Leu
50                  55                  60

Val Asp Gln Ala Arg Thr Val Leu Arg Glu Val Lys Val Leu Lys Glu
65                  70                  75                  80

Met Ala Ser Gln Gln Gly Glu Thr Met Ser Gly Pro Leu His Ile Gly
                85                  90                  95

Leu Ile Pro Thr Val Gly Pro Tyr Leu Leu Pro His Ile Ile Pro Met
            100                 105                 110

Leu His Gln Thr Phe Pro Lys Leu Glu Met Tyr Leu His Glu Ala Gln
        115                 120                 125

Thr His Gln Leu Leu Ala Gln Leu Asp Ser Gly Lys Leu Asp Cys Val
    130                 135                 140

Ile Leu Ala Leu Val Lys Glu Ser Glu Ala Phe Ile Glu Val Pro Leu
145                 150                 155                 160

Phe Asp Glu Pro Met Leu Leu Ala Ile Tyr Glu Asp His Pro Trp Ala
                165                 170                 175

Asn Arg Glu Cys Val Pro Met Ala Asp Leu Ala Gly Glu Lys Leu Leu
            180                 185                 190

Met Leu Glu Asp Gly His Cys Leu Arg Asp Gln Ala Met Gly Phe Cys
        195                 200                 205

Phe Glu Ala Gly Ala Asp Glu Asp Thr His Phe Arg Ala Thr Ser Leu
    210                 215                 220

Glu Thr Leu Arg Asn Met Val Ala Ala Gly Ser Gly Ile Thr Leu Leu
225                 230                 235                 240

Pro Ala Leu Ala Val Pro Pro Glu Arg Lys Arg Asp Gly Val Val Tyr
                245                 250                 255

Leu Pro Cys Ile Lys Pro Glu Pro Arg Arg Thr Ile Gly Leu Val Tyr
            260                 265                 270

Arg Pro Gly Ser Pro Leu Arg Ser Arg Tyr Glu Gln Leu Ala Glu Ala
        275                 280                 285

Ile Arg Ala Arg Met Asp Gly His Phe Asp Lys Val Leu Lys Gln Ala
    290                 295                 300

Val
305

<210> SEQ ID NO 20
<211> LENGTH: 95
<212> TYPE: DNA
<213> ORGANISM: Artificial sequence
<220> FEATURE:
<223> OTHER INFORMATION: Synthetic oligonucletide

<400> SEQUENCE: 20
ggaagatggt cgtctccggt gaggcggctg gactctaaat ccagttgggg ccgccagcgg     60
tcccggtcag gttcgactcc ttgcatcttc cgcca                                95

<210> SEQ ID NO 21
<211> LENGTH: 95
<212> TYPE: DNA
<213> ORGANISM: Artificial sequence
```

```
<220> FEATURE:
<223> OTHER INFORMATION: Synthetic oligonucletide

<400> SEQUENCE: 21
ggaagatcgt cgtctccggt gaggcggctg gactctaaat ccagttgggg ccgccagcgg    60
tcccggtcag gttcgactcc ttggatcttc cgcca                              95

<210> SEQ ID NO 22
<211> LENGTH: 94
<212> TYPE: DNA
<213> ORGANISM: Artificial sequence
<220> FEATURE:
<223> OTHER INFORMATION: Synthetic oligonucletide

<400> SEQUENCE: 22
ggaagatcgt cgtctccggt gaggcggctg gactctaaat ccagttgggg ccgccagcgg    60
tcccggtaag gttcgactcc tatatcttcc gcca                               94

<210> SEQ ID NO 23
<211> LENGTH: 90
<212> TYPE: DNA
<213> ORGANISM: Artificial sequence
<220> FEATURE:
<223> OTHER INFORMATION: Synthetic oligonucletide

<400> SEQUENCE: 23
ggaagatgtg gccgagcggt tgaaggcacc ggtctctaaa accggcgacc cgaaagggtt    60
ccagagttcg aatctctgca tcttccgcca                                    90

<210> SEQ ID NO 24
<211> LENGTH: 292
<212> TYPE: PRT
<213> ORGANISM: Artificial sequence
<220> FEATURE:
<223> OTHER INFORMATION: Synthetic polypeptide

<400> SEQUENCE: 24

Met Ser Leu Asn Val Lys Gln Ser Arg Ile Ala Ile Leu Phe Ser Ser
1               5                   10                  15

Cys Leu Ile Ser Ile Ser Phe Phe Ser Gln Ala Asn Thr Lys Gly Ile
            20                  25                  30

Asp Glu Ile Lys Asn Leu Glu Thr Asp Phe Asn Gly Arg Ile Gly Val
        35                  40                  45

Tyr Ala Leu Asp Thr Gly Ser Gly Lys Ser Phe Ser Tyr Arg Ala Asn
    50                  55                  60

Glu Arg Phe Pro Leu Cys Ser Ser Phe Lys Gly Phe Leu Ala Ala Ala
65                  70                  75                  80

Val Leu Lys Gly Ser Gln Asp Asn Arg Leu Asn Leu Asn Gln Ile Val
                85                  90                  95

Asn Tyr Asn Thr Arg Ser Leu Glu Phe His Ser Pro Ile Thr Thr Lys
            100                 105                 110

Tyr Lys Asp Asn Gly Met Ser Leu Gly Asp Met Ala Ala Ala Ala Leu
        115                 120                 125

Gln Tyr Ser Asp Asn Gly Ala Thr Asn Ile Ile Leu Glu Arg Tyr Ile
    130                 135                 140

Gly Gly Pro Glu Gly Met Thr Lys Phe Met Arg Ser Ile Gly Asp Glu
145                 150                 155                 160

Asp Phe Arg Leu Asp Arg Trp Glu Leu Asp Leu Asn Thr Ala Ile Pro
                165                 170                 175
```

Gly Asp Glu Arg Asp Thr Ser Thr Pro Ala Ala Val Ala Lys Ser Leu
            180                 185                 190

Lys Thr Leu Ala Leu Gly Asn Ile Leu Ser Glu His Glu Lys Glu Thr
        195                 200                 205

Tyr Gln Thr Trp Leu Lys Gly Asn Thr Thr Gly Ala Ala Arg Ile Arg
    210                 215                 220

Ala Ser Val Pro Ser Asp Trp Val Val Gly Asp Lys Thr Gly Ser Cys
225                 230                 235                 240

Gly Ala Tyr Gly Thr Ala Asn Asp Tyr Ala Val Val Trp Pro Lys Asn
                245                 250                 255

Arg Ala Pro Leu Ile Ile Ser Val Tyr Thr Thr Lys Asn Glu Lys Glu
                260                 265                 270

Ala Lys His Glu Asp Lys Val Ile Ala Glu Ala Ser Arg Ile Ala Ile
            275                 280                 285

Asp Asn Leu Lys
    290

<210> SEQ ID NO 25
<211> LENGTH: 879
<212> TYPE: DNA
<213> ORGANISM: Artificial sequence
<220> FEATURE:
<223> OTHER INFORMATION: Synthetic oligonucletide

<400> SEQUENCE: 25

```
atgtcactta atgtaaagca aagtagaata gccatcttgt ttagctcttg tttaatttca      60
atatcatttt tctcacaggc caatacgaag ggcattgatg agattaaaaa ccttgaaaca     120
gatttcaatg gcaggattgg tgtctacgct ttagacactg gctcgggtaa atcattttcg     180
tacagagcaa atgaacgatt tccattatag agttctttta aaggtttttt agctgctgct     240
gtattaaaag gctctcaaga taatcgactt aatcttaatc agattgtgaa ttataataca     300
agaagtttag agttccattc acccatcaca actaaatata aagataatgg aatgtcatta     360
ggtgatatgg ctgctgctgc tttacaatat agcgacaatg gtgctactaa tattattctt     420
gaacgttata tcggtggtcc agagggtatg actaaattca tgcggtcgat tggagatgaa     480
gattttagac tcgatcgttg ggagttagat ctaaacacag ctattccagg cgatgagcgt     540
gacacatcta cacctgcagc agtagccaag agtctgaaaa cccttgctct gggtaacata     600
cttagtgaac atgaaaagga aacctatcag acatggttaa agggtaacac aaccggtgca     660
gcgcgtattc gtgctagcgt accaagcgat tgggtagttg gcgataaaac tggtagttag     720
ggagcatacg gtacggcaaa tgattatgcg gtagtctggc caaagaaccg ggctcctctt     780
ataatttctg tatacacaac aaaaaacgaa aaagaagcca agcatgagga taaagtaatc     840
gcagaagctt caagaattgc aattgataac cttaaataa                            879
```

<210> SEQ ID NO 26
<211> LENGTH: 167
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (39)..(39)
<223> OTHER INFORMATION: Xaa = Selenocysteine
<220> FEATURE:
<221> NAME/KEY: MISC_FEATURE
<222> LOCATION: (85)..(85)

<223> OTHER INFORMATION: Xaa = Selenocysteine

<400> SEQUENCE: 26

Met Ile Ser Leu Ile Ala Ala Leu Ala Val Asp Arg Val Ile Gly Asn
1               5                   10                  15

Glu Met Ala Met Pro Trp Asn Leu Pro Ala Asp Leu Ala Trp Phe Lys
            20                  25                  30

Arg Asn Thr Leu Asn Lys Xaa Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Gly Thr Asp Asp Arg Val Thr Trp Val Lys Ser Val Asp Glu
65                  70                  75                  80

Ala Ile Ala Ala Xaa Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg Gly
145                 150                 155                 160

Ser His His His His His His
                165

<210> SEQ ID NO 27
<211> LENGTH: 294
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (42)..(42)
<223> OTHER INFORMATION: Xaa = Selenocysteine
<220> FEATURE:
<221> NAME/KEY: MISC_FEATURE
<222> LOCATION: (116)..(116)
<223> OTHER INFORMATION: Xaa = Selenocysteine
<220> FEATURE:
<221> NAME/KEY: MISC_FEATURE
<222> LOCATION: (179)..(179)
<223> OTHER INFORMATION: Xaa = Selenocysteine
<220> FEATURE:
<221> NAME/KEY: MISC_FEATURE
<222> LOCATION: (249)..(249)
<223> OTHER INFORMATION: Xaa = Selenocysteine

<400> SEQUENCE: 27

Met His His His His His His Leu Val Pro Arg Gly Ser Gly Lys Ser
1               5                   10                  15

Ala Met Ala Ala Glu Val Lys Leu Val Glu Ser Gly Gly Gly Leu Val
            20                  25                  30

Lys Pro Gly Gly Ser Leu Lys Leu Ser Xaa Ala Ala Ser Gly Phe Thr
        35                  40                  45

Phe Ser Ser Tyr Ala Met Ser Trp Val Arg Gln Thr Pro Glu Lys Arg
    50                  55                  60

Leu Glu Trp Val Ala Thr Ile Ser Thr Gly Gly Gly Tyr Thr Tyr Phe
65                  70                  75                  80

Pro Asp Ser Val Lys Gly Arg Phe Thr Ile Ser Arg Asp Asn Ala Lys

```
                    85                  90                  95
Asn Ala Leu Tyr Leu Gln Met Lys Ser Leu Arg Ser Glu Asp Thr Ala
                100                 105                 110
Met Tyr Tyr Xaa Ala Arg Gln Gly Asp Phe Gly Asp Trp Tyr Phe Asp
                115                 120                 125
Val Trp Gly Ala Gly Thr Thr Val Thr Val Ser Ser Gly Gly Gly Gly
            130                 135                 140
Ser Gly Gly Gly Gly Ser Gly Gly Gly Gly Ser Thr Asp Val Leu Met
145                 150                 155                 160
Thr Gln Thr Pro Leu Ser Leu Pro Val Ser Leu Gly Asp Gln Ala Ser
                165                 170                 175
Ile Ser Xaa Arg Ser Ser Gln Ser Leu Val His Ser Asn Gly Asn Thr
            180                 185                 190
Tyr Leu His Trp Tyr Leu Gln Lys Pro Gly Gln Ser Pro Lys Leu Leu
        195                 200                 205
Ile Tyr Lys Val Ser Asn Arg Phe Ser Gly Val Pro Asp Arg Phe Ser
    210                 215                 220
Gly Ser Gly Ser Gly Thr Asp Phe Thr Leu Lys Ile Ser Arg Val Glu
225                 230                 235                 240
Ala Glu Asp Leu Gly Val Tyr Phe Xaa Ser Gln Ser Thr His Val Pro
                245                 250                 255
Trp Thr Phe Gly Gly Gly Thr Lys Leu Glu Ile Lys Arg Ala Ala Ala
            260                 265                 270
Asp Tyr Lys Asp His Asp Gly Asp Tyr Lys Asp His Asp Ile Asp Tyr
        275                 280                 285
Lys Asp Asp Asp Asp Lys
        290

<210> SEQ ID NO 28
<211> LENGTH: 252
<212> TYPE: PRT
<213> ORGANISM: Artificial sequence
<220> FEATURE:
<223> OTHER INFORMATION: Synthetic polypeptide

<400> SEQUENCE: 28

Met Glu Val Gln Leu Leu Glu Ser Gly Gly Gly Leu Ala Lys Pro Gly
1               5                   10                  15
Gly Ser Leu Arg Leu Ser Cys Ala Ala Ser Gly Phe Thr Phe Thr Asp
                20                  25                  30
Tyr Tyr Met Asp Trp Val Arg Gln Ala Pro Gly Lys Gly Leu Glu Trp
            35                  40                  45
Val Ser Arg Ile Ser Pro Gly Gly Asp Val Thr Trp Tyr Ala Asp Ser
        50                  55                  60
Val Lys Gly Arg Phe Thr Ile Ser Arg Asp Asn Ala Gln Asn Thr Leu
65                  70                  75                  80
Tyr Leu Gln Met Asn Ser Leu Arg Ala Glu Asp Thr Ala Val Tyr Phe
                85                  90                  95
Cys Ala Arg Asp Asp Ile Val Val Ser Arg Ile Phe Asp Asp Trp Gly
                100                 105                 110
Gln Gly Val Leu Leu Thr Val Ser Ser Gly Gly Gly Gly Ser Gly Gly
            115                 120                 125
Gly Gly Ser Gly Gly Gly Gly Ser Glu Leu Gln Met Thr Gln Ser Pro
        130                 135                 140
Ser Ser Leu Ser Ala Ser Val Gly Asp Arg Val Thr Ile Thr Cys Arg
```

```
                145                 150                 155                 160
Ala Ser Gln Ser Ile Arg Ser Tyr Leu Ala Trp Tyr Gln Gln Lys Pro
                    165                 170                 175

Gly Lys Ala Pro Lys Leu Leu Ile Tyr Asp Ala Ala His Leu Gln Ser
                180                 185                 190

Gly Val Pro Ser Arg Phe Ser Gly Ser Gly Ser Gly Thr Glu Phe Ser
                195                 200                 205

Leu Thr Ile Ser Ser Leu Gln Pro Glu Asp Phe Ala Val Tyr Tyr Cys
            210                 215                 220

Gln Gln Arg Asn Ser Tyr Pro Leu Thr Phe Gly Gly Gly Thr Lys Val
225                 230                 235                 240

Glu Ile Lys Arg Gly Ser His His His His His His
                245                 250

<210> SEQ ID NO 29
<211> LENGTH: 252
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (23)..(23)
<223> OTHER INFORMATION: Xaa = Selenocysteine
<220> FEATURE:
<221> NAME/KEY: MISC_FEATURE
<222> LOCATION: (97)..(97)
<223> OTHER INFORMATION: Xaa = Selenocysteine
<220> FEATURE:
<221> NAME/KEY: MISC_FEATURE
<222> LOCATION: (159)..(159)
<223> OTHER INFORMATION: Xaa = Selenocysteine
<220> FEATURE:
<221> NAME/KEY: MISC_FEATURE
<222> LOCATION: (224)..(224)
<223> OTHER INFORMATION: Xaa = Selenocysteine

<400> SEQUENCE: 29

Met Glu Val Gln Leu Leu Glu Ser Gly Gly Gly Leu Ala Lys Pro Gly
1               5                   10                  15

Gly Ser Leu Arg Leu Ser Xaa Ala Ala Ser Gly Phe Thr Phe Thr Asp
                20                  25                  30

Tyr Tyr Met Asp Trp Val Arg Gln Ala Pro Gly Lys Gly Leu Glu Trp
            35                  40                  45

Val Ser Arg Ile Ser Pro Gly Gly Asp Val Thr Trp Tyr Ala Asp Ser
    50                  55                  60

Val Lys Gly Arg Phe Thr Ile Ser Arg Asp Asn Ala Gln Asn Thr Leu
65                  70                  75                  80

Tyr Leu Gln Met Asn Ser Leu Arg Ala Glu Asp Thr Ala Val Tyr Phe
                85                  90                  95

Xaa Ala Arg Asp Asp Ile Val Val Ser Arg Ile Phe Asp Asp Trp Gly
                100                 105                 110

Gln Gly Val Leu Leu Thr Val Ser Gly Gly Gly Gly Ser Gly Gly
                115                 120                 125

Gly Gly Ser Gly Gly Gly Ser Glu Leu Gln Met Thr Gln Ser Pro
            130                 135                 140

Ser Ser Leu Ser Ala Ser Val Gly Asp Arg Val Thr Ile Thr Xaa Arg
145                 150                 155                 160

Ala Ser Gln Ser Ile Arg Ser Tyr Leu Ala Trp Tyr Gln Gln Lys Pro
                165                 170                 175
```

```
Gly Lys Ala Pro Lys Leu Leu Ile Tyr Asp Ala Ala His Leu Gln Ser
            180                 185                 190

Gly Val Pro Ser Arg Phe Ser Gly Ser Gly Ser Gly Thr Glu Phe Ser
            195                 200                 205

Leu Thr Ile Ser Ser Leu Gln Pro Glu Asp Phe Ala Val Tyr Tyr Xaa
210                 215                 220

Gln Gln Arg Asn Ser Tyr Pro Leu Thr Phe Gly Gly Gly Thr Lys Val
225                 230                 235                 240

Glu Ile Lys Arg Gly Ser His His His His His
            245                 250
```

<210> SEQ ID NO 30
<211> LENGTH: 255
<212> TYPE: PRT
<213> ORGANISM: Artificial sequence
<220> FEATURE:
<223> OTHER INFORMATION: Synthetic polypeptide

<400> SEQUENCE: 30

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Tyr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Ala Ser Gly
            100                 105                 110

Gly Gly Gly Ser Gly Gly Gly Ser Gly Gly Gly Ser Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Thr Tyr Ala Met Asp Tyr Trp Gly Gln Gly
225                 230                 235                 240

Thr Leu Val Thr Val Ser Ser Gly Ser His His His His His
                245                 250                 255
```

<210> SEQ ID NO 31
<211> LENGTH: 255
<212> TYPE: PRT
<213> ORGANISM: Artificial sequence
<220> FEATURE:

```
<223> OTHER INFORMATION: Synthetic polypeptide
<220> FEATURE:
<221> NAME/KEY: MISC_FEATURE
<222> LOCATION: (24)..(24)
<223> OTHER INFORMATION: Xaa = Selenocysteine
<220> FEATURE:
<221> NAME/KEY: MISC_FEATURE
<222> LOCATION: (89)..(89)
<223> OTHER INFORMATION: Xaa = Selenocysteine
<220> FEATURE:
<221> NAME/KEY: MISC_FEATURE
<222> LOCATION: (149)..(149)
<223> OTHER INFORMATION: Xaa = Selenocysteine
<220> FEATURE:
<221> NAME/KEY: MISC_FEATURE
<222> LOCATION: (223)..(223)
<223> OTHER INFORMATION: Xaa = Selenocysteine

<400> SEQUENCE: 31

Met Asp Ile Gln Met Thr Gln Ser Pro Ser Ser Leu Ser Ala Ser Val
  1               5                  10                  15

Gly Asp Arg Val Thr Ile Thr Xaa Arg Ala Ser Gln Asp Val Asn Thr
             20                  25                  30

Ala Val Ala Trp Tyr Gln Gln Lys Pro Gly Lys Ala Pro Lys Leu Leu
         35                  40                  45

Ile Tyr Ser Ala Ser Phe Leu Tyr Ser Gly Val Pro Ser Arg Phe Ser
 50                  55                  60

Gly Ser Arg Ser Gly Thr Asp Phe Thr Leu Tyr Ile Ser Ser Leu Gln
 65                  70                  75                  80

Pro Glu Asp Phe Ala Thr Tyr Tyr Xaa Gln Gln His Tyr Thr Thr Pro
             85                  90                  95

Pro Thr Phe Gly Gln Gly Thr Lys Val Glu Ile Lys Gly Ala Ser Gly
            100                 105                 110

Gly Gly Gly Ser Gly Gly Gly Ser Gly Gly Gly Ser Ser Glu
            115                 120                 125

Val Gln Leu Val Glu Ser Gly Gly Leu Val Gln Pro Gly Gly Ser
        130                 135                 140

Leu Arg Leu Ser Xaa Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Xaa Ser
210                 215                 220

Arg Trp Gly Gly Asp Gly Thr Tyr Ala Met Asp Tyr Trp Gly Gln Gly
225                 230                 235                 240

Thr Leu Val Thr Val Ser Ser Gly Ser His His His His His
                245                 250                 255
```